United States Patent [19]
Klunk et al.

[11] Patent Number: 6,133,259
[45] Date of Patent: Oct. 17, 2000

[54] ALKYL, ALKENYL AND ALKYNYL CHRYSAMINE G DERIVATIVES FOR INHIBITION OF CELL DEGENERATION AND TOXICITY ASSOCIATED WITH AMYLOID DEPOSITION

[75] Inventors: William E. Klunk; Jay W. Pettegrew; Chester A. Mathis, Jr., all of Pittsburgh, Pa.

[73] Assignee: University of Pittsburgh, Pittsburgh, Pa.

[21] Appl. No.: 09/188,200

[22] Filed: Nov. 9, 1998

Related U.S. Application Data

[60] Division of application No. 08/837,494, Apr. 18, 1997, which is a continuation-in-part of application No. 08/640,704, May 1, 1996, abandoned, and a continuation of application No. PCT/US96/05918, May 1, 1996, which is a continuation-in-part of application No. 08/432,019, May 1, 1995, abandoned, which is a continuation-in-part of application No. 08/282,289, Jul. 29, 1994, abandoned.

[51] Int. Cl.$^7$ ...................................................... A61N 25/28
[52] U.S. Cl. ........................ 514/230.5; 514/248; 514/296; 514/309; 514/364; 514/371; 514/381; 514/417; 514/493; 514/534; 514/568; 424/1.11; 544/64; 544/94; 544/225; 544/237; 546/100; 546/103; 546/123; 546/241; 546/478; 546/480; 548/101; 548/143; 562/475; 556/87
[58] Field of Search ............................ 424/1, 110; 536/63, 536/811; 514/534, 230.5, 248, 296, 309, 364, 379, 381, 417, 493, 568

[56] References Cited

U.S. PATENT DOCUMENTS

| | | | |
|---|---|---|---|
| 329,638 | 11/1885 | Frank | 534/670 |
| 394,841 | 12/1888 | Duisberg | 534/670 |
| 401,024 | 9/1889 | Frank | 534/670 |
| 622,961 | 4/1899 | Levinstein et al. | 534/670 |
| 1,979,534 | 11/1934 | Ebert | 534/670 |
| 4,933,156 | 6/1990 | Quay et al. | 534/670 X |
| 5,008,099 | 4/1991 | Quay et al. | 424/1.1 |
| 5,039,511 | 8/1991 | Quay et al. | 424/1.1 |
| 5,231,000 | 7/1993 | Majocha et al. | 435/7.1 |
| 5,276,059 | 1/1994 | Caughey et al. | 514/647 |
| 5,358,712 | 10/1994 | Etange et al. | 424/1.65 |

FOREIGN PATENT DOCUMENTS

| | | |
|---|---|---|
| 0 287 909 | 10/1988 | European Pat. Off. |
| WO 92/17152 | 10/1992 | WIPO |
| WO 93/04194 | 3/1993 | WIPO |

OTHER PUBLICATIONS

Greenbaum, "Improved Method for the Preparation of Calcium or Ammonium", *Chemical Abstracts*, vol. 30, p. 2559 (1936).
Tubis et al., "The Preparation and Use of Radioiodinated Congo Red in Detecting Amyloidosis", *Journal of the Amer. Pharma. Assoc.*, vol. 49, pp. 422–425 (Jul. 1960).
Böshagen, "Method of Synthesis of 3–Hydroxy–1,2–Benzisoxazoles", *Chem. Ber.*, vol. 100, pp. 954–960 (1967).
Effenberger et al., "A Method for the Synthesis of 1,3–Benzoxazines", *Chem. Ber.*, vol. 105, pp. 1926–1942 (1972).
Wisniewski et al., "Neuritic (Senile) Plaques and Filamentous Changes in Aged Rhesus Monkeys", *J. Neuropathol. & Exp. Neurol.*, vol. 32, pp. 566–584 (1973).
Coenen et al., "No–Carrier–Added Radiohalogenation Methods with Heavy Halogens", *Radiochimica Acta*, vol. 34, p. 47–68 (1983).
Satyamurthy et al., "Cation Exchange Resin (Hydrogen Form) Assisted Decomposition . . . A Mild and Efficient Method for the Synthesis of Aryl Iodides", *J. Org. Chem.*, vol. 48, No. 23, pp. 4394–4396 (1983).
Goodman et al., "New Myocardial Imaging Agents: Synthesis of 15–(p–Iodophenyl)–3(R,S)–Methylpentadecanoic Acid by Decomposition of a 3,3–(1,5–Pentanediyl)triazene Precursor", *J. Org. Chem.*, 49:2322–2325 (1984).
Fowler et al., "Positron Emitter–Labeled Compounds: Priorities and Problems", *Positron Emission Tomography and Autoradiography: Principles and Applications for the Brain and Heart*, pp. 391–450 (1986).
Young et al., "Receptor Assays: In Viro and In Vivo", *Positron Emission Tomography and Autoradiography: Principles and Applications for the Brain and Heart*, pp. 73–111 (1986).
Warner, "Diagnosis of Alzheimer's Disease", *Analytical Chemistry*, vol. 59, No. 20, pp. 12105A–1204A (Oct. 1987).
Klunk et al., "Beta–Amyloid Probes which Cross the Blood–rain Barrier and Distinguish Homogenates of Alzheimer's and Control Brain", *Society for Neuroscience Abstracts*, Abstract 182.1, vol. 19, p. 430 (1989).
Kulkarni, "Recent Developments in $^{99m}$Tc and $^{123}$I–Radiopharmaceuticals for SPECT Imaging", *Nucl. Med. Biol.*, vol. 18, No. 6, pp. 647–654 (1991).
Majocha et al., "Development of a Monoclonal Antibody Specific for β/A4 Amyloid . . . for Application to In Vivo Imaging of Amyloid Angiopathy", *The Journal of Nuclear Medicine*, vol. 33, No. 12, pp. 2184–2189 (Dec. 1992).
"Definitive Rules for Nomenclature of Organic Chemistry", *Handbook of Chemistry and Physics*, 45th Ed., pp. C33–C39 (1964).

(List continued on next page.)

*Primary Examiner*—Floyd D. Higel
*Attorney, Agent, or Firm*—Foley & Lardner

[57] ABSTRACT

Amyloid binding compounds which are non-azo derivatives of Chrysamine G, pharmaceutical compositions containing, and methods using such compounds to identify Alzheimer's brain in vivo and to diagnose other pathological conditions characterized by amyloidosis, such as Down's Syndrome are described. Pharmaceutical compositions containing non-azo derivatives of Chrysamine G and methods using such compositions to prevent cell degeneration and amyloid-induced toxicity in amyloidosis associated conditions are also described. Methods using non-azo Chrysamine G derivatives to stain or detect amyloid deposits in biopsy or post-mortem tissue are also described. Methods using non-azo Chrysamine G derivatives to quantify amyloid deposits in homogenates of biopsy and post-mortem tissue are also described.

2 Claims, 15 Drawing Sheets

OTHER PUBLICATIONS

"Chrysamine G", *Conn's Biological Stains*, 9th Ed., p. 150 (1977).

Masters et al., "Amyloid Plaque Core Protein in Alzheimer Disease and Down Syndrome", *Proc. Natl. Acad. Sci. USA*, vol. 82, pp. 4245–4249 (Jun. 1985).

Kirschner et al., "Synthetic Peptide Homologous to β Protein from Alzheimer Disease Forms Amyloid–Like Fibrils in vitro", *Proc. Natl. Acad. Sci. USA*, vol. 84, pp. 6953–6957 (Oct. 1987).

Zain et al., "Molecular Cloning of Amyloid cDNA Derived from mRNA of the Alzheimer Disease Brain: Coding and Noncoding Regions of the Fetal Precursor mRNA are Expressed in the Cortex", *Proc. Natl. Acad. Sci. USA*, vol. 85, pp. 929–933 (Feb. 1988).

Goate et al., "Segregation of Missense Mutation in the Amyloid Precursor Protein Gene with Familial Alzheimer's Disease", *Nature*, vol. 349, pp. 704–706 (Feb. 1991).

Honda et al., "Arginine Specific Endopeptidases Modify the Aggregation Properties of a Synthetic Peptide Derived from Alzheimer β/A4 Amyloid", *Neurochemical Research*, vol. 17, No. 4, pp. 367–374 (1992).

Salim et al., "Molecular Cloning of Amyloid cDNA from Alzheimer's Brain Messenger RNA: Correlative Neuroimmunological and in Situ Hybridization Studies", pp. 153–165.

"Aromatic Diazo Compounds", *Chemical Abstracts*, vo. 49, p. 7855.

Pollack et al., "Sulfated Glycosaminoglycans and Dyes Attentuate the Neurotoxic Effects of β–Amyloid in Rat PC12 Cells," *Neurosci. lett.*, 184: 113–116 (1995).

Lorenzo and Yankner, "β–Amyloid Neurotoxicity Requires Fibril Formation and is Inhibited by Congo Red," *PNAS (USA)* 91: 12243–12247 (1994).

Klunk et al., "Development of Small Molecule Probes for the Beta–Amyloid Protein of Alzheimer's Disease," *Neurobiology of Aging*, 15(6): 691–698 (1994).

Klunk et al., "Chrysamine–G Binding to Alzheimer and Control Brain: Autopsy Study of a New Amyloid Probe" *Neurobiology of Aging*, 16(4): 541–548 (1995).

Klunk et al., "Design of Diagnostic Probes for Alzheimer's Beta/A4 Peptide," 20th Annual Meeting of Soc. Neuroscience 1990.

Klunk et al., "Beta–Amyloid Probes Which Cross the Blood–Brain Barrier and Distinguish Homogenates of Alzheimer's and Control Brain," 23rd Annual Meeting of Soc. Neuroscience 1993.

Han et al, J. Am. Chem. Soc., 1996, 118, pp. 4506–4507, "Technetium Complexes for the Quantitation of Brain Amyloid".

Ashby et al, "Evaluation of two suggested methods of deactivating organic carcinogens by molecular modification", Carcinogenesis, vol. 3, No. 11, pp. 1277–1282, 1982.

Josephy et al, "Azo Dyes Based on 3,5,3',5'–Tetramethylbenzidine: Potential Substitutes for Carcinogenic Azo Dyes", Chem.–Biol. Interactions, 49 (1984) pp. 375–382.

Cerniglia et al, Biochemical and Biophysical Research Communications, pp. 1224–1229, vol. 107, No.4, 1982, "Metabolism of Benzidine and Benzidine Congener Based Dyes by Human, Monkey and Rat Intestinal Bacteria".

Mahapatra, Bipin. B. et al., "Polymetallic Complexes. Part–XXX. Complexes Of Cobalt–, Nickel–, Copper–, Zinc–, Cadmium– and Mercury (II) With Doubly–tridentate Chelating Azo–Dye Ligand", Chem. Abstr. vol. 114, No. 26, Jul. 1, 1991.

Hirao, Akiko et al., "Positively charged laminated electrophotographic photoconductor with charge–generating layer containing disazo compound", Chem. Abstr. vol. 110, No. 24, Jun. 12, 1989.

Enomoto, Kazuhiro et al., "Electrophotographic photoreceptors", Chem. Abstr. vol. 104, No. 20, May 19, 1986.

Harada, Kouzou, "Azo dyes. XXVIII. Azo dyes from 1–amino–2–hydroxy–3–naphthoic acid and 5–sulfo–3–hydroxy–2–naphthoic acid", Chem. Abstr. vol. 69, No. 2, Jul. 8, 1968.

Kazuya, Murata et al., "Phenanthrene dyes" Chem. Abstr. vol. 56, No. 2, Jan. 22, 1962.

Tomohiko, Kawei et al., "3,7–Diaminodibenzothiophene 5,5,–dioxide. I. Syntheses of 3.7–bisazo compounds of dibenzothiophene 5,5,–dioxide" Chem. Abstr. vol. 55, No. 8, Apr. 17, 1961.

Kazuya, Murata et al., "Azo dyes from 2–amino–5–anilinophenylthioglycolic acid", Chem. Abstr. vol. 53, No. 12, Jun. 25, 1959.

Mitsubishi Paper Mills, Ltd., "Electrophotographic sensitive material", Chem. Abstr. vol. 102, No. 6, Feb. 11, 1985.

Canon K. K., "Inks for ink–jet printing", Chem. Abstr. vol. 100, No. 16, Apr. 16, 1984.

Hishiki, Yasushi et al., "Effects of chemical structure of azo dyes upon absorption spectra, redox potential and photographic response of silver halide emulsion", Chem. Abstr. vol. 94, No. 6, Feb. 9, 1981.

Baiulescu, George E., et al., "Spectrophotometric study of the beryllium (II) reaction with two bisazoic derivatives", Chem. Abstr. vol. 84, No. 16, Apr. 19, 1976.

FIG. 2A
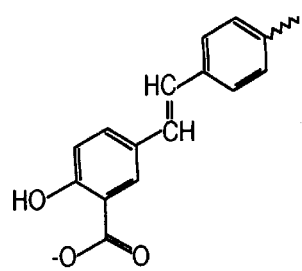
SALICYLIC ACID ALKENYL BIPHENYL DERIVATIVE.

FIG. 2B
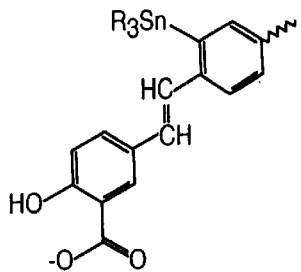
SALICYLIC ACID ALKENYL DERIVATIVE WITH GENERAL TRI-ALKYL TIN.

FIG. 2C
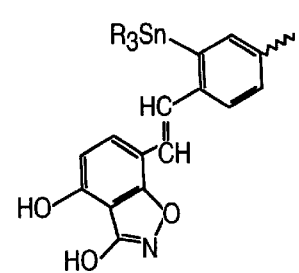
3-HYDROXY-1,2-BENZISOXAZOLE DERIVATIVE.

FIG. 2D
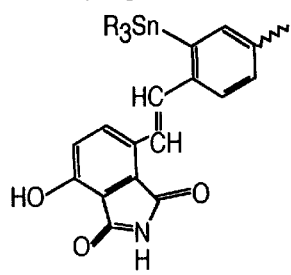
PHTHALIMIDE OR ISOINDOLE-1,3(2H)-DIONE DERIVATIVE..

FIG. 2E
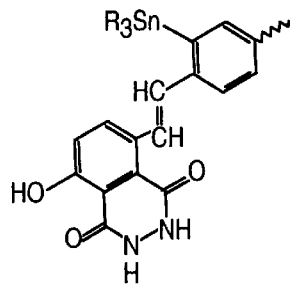
PHTHALHYDRAZIDE OR 2,3 BENZODIAZINE- 1,4 (2H,3H)-DIONE.

FIG. 2F
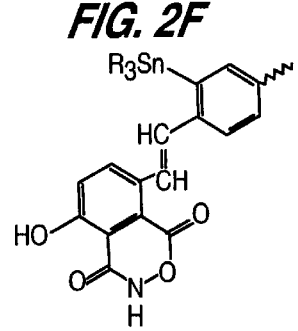
BENZOXAZINE-1,4(3H)-DIONE DERIVATIVE.

FIG. 2G
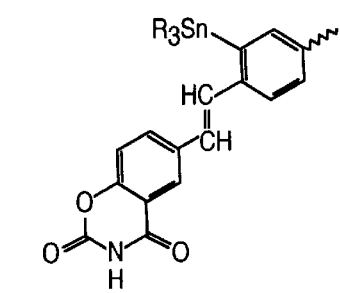
(2H)1,3-BENZOXAZINE-2,4(3H)-DIONE DERIVATIVE.

FIG. 2H
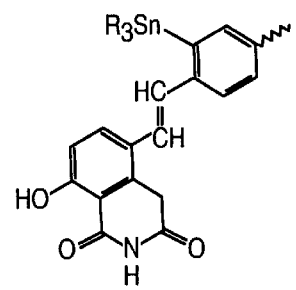
(3H)-2-BENZAZINE-1,3(2H)-DIONE DERIVATIVE.

FIG. 2I
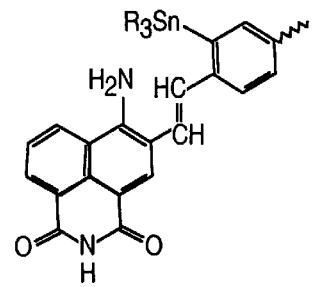
1,8-NAPHTHALIMIDE DERIVATIVE

FIG. 2J
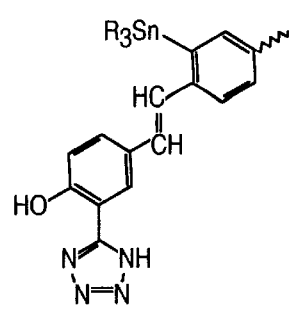
TETRAZOLE DERIVATIVE.

FIG. 2K
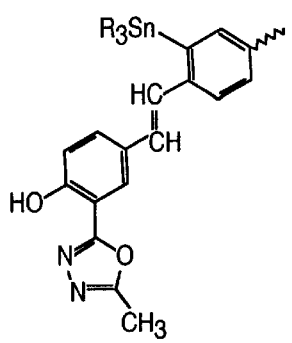
OXADIAZOLE DERIVATIVE.

FIG. 4
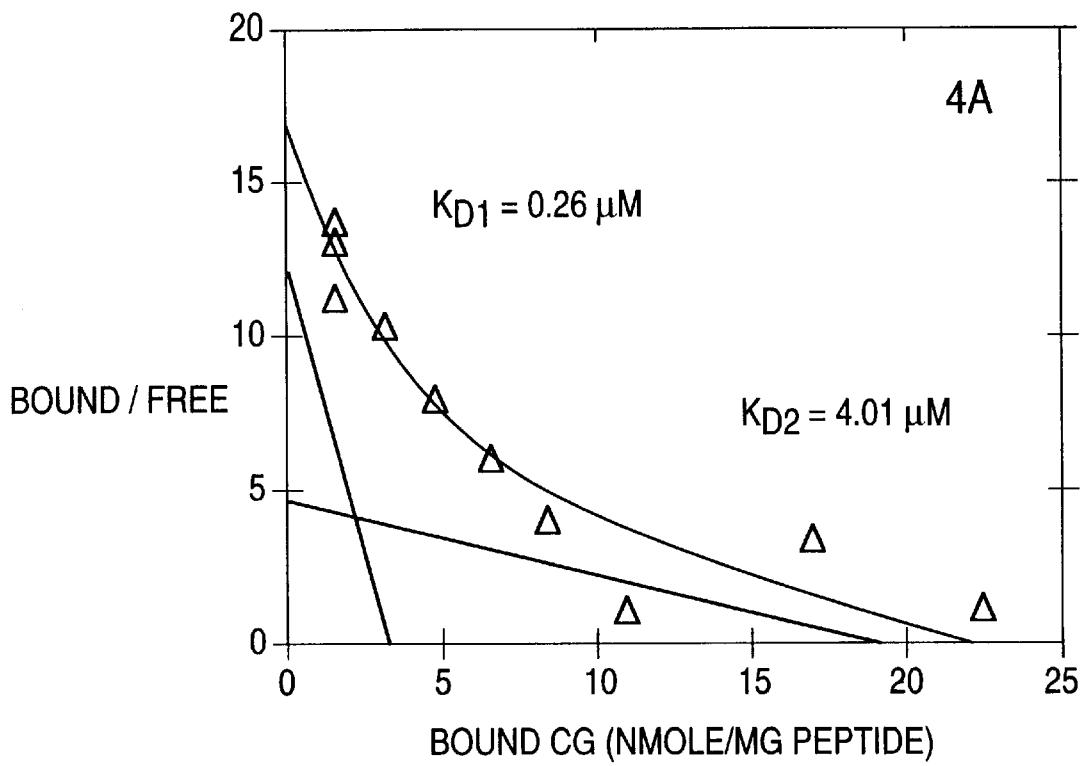
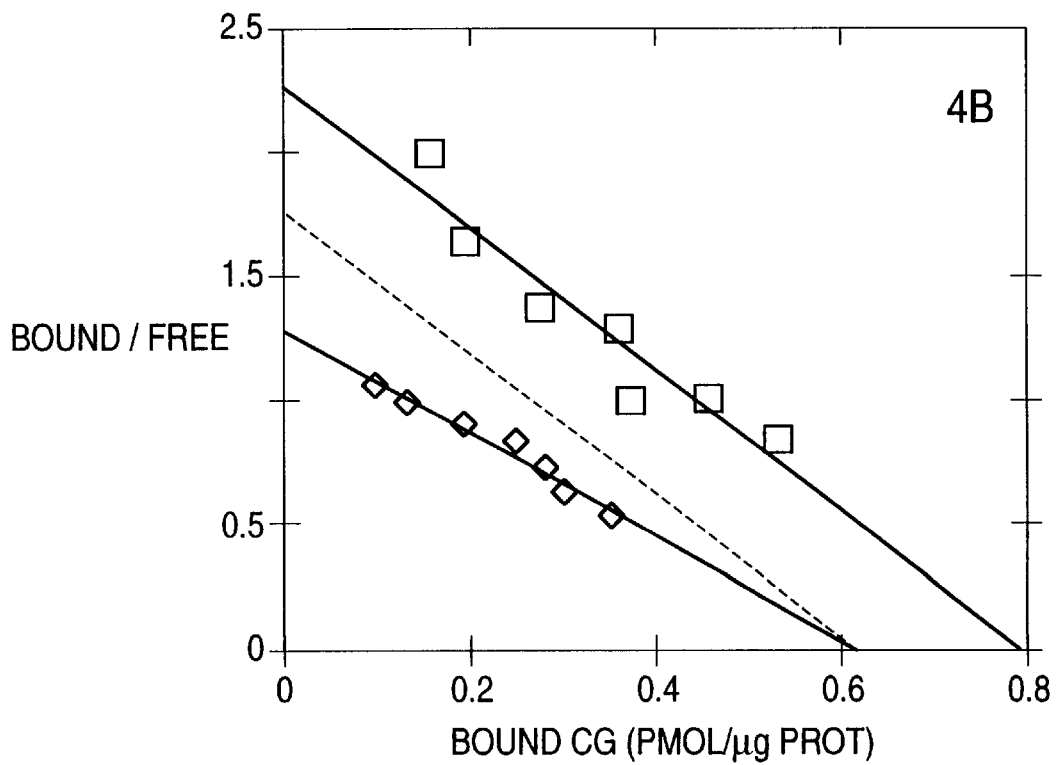

ously filed on this or any such later date.
ALKYL, ALKENYL AND ALKYNYL CHRYSAMINE G DERIVATIVES FOR INHIBITION OF CELL DEGENERATION AND TOXICITY ASSOCIATED WITH AMYLOID DEPOSITION This application is a divisional of application Ser. No. 08/837,494, filed Apr. 18, 1997, which is in turn a continuation-in-part of U.S. patent application Ser. No. 08/640,704, now abandoned, and also a continuation-in-part of International Patent application, PCT/US96/05918, both filed May 1, 1996, which is in turn a continuation-in-part of U.S. patent application Ser. No. 08/432,019, now abandoned, filed May 1, 1995, which is in turn a continuation-in-part of U.S. patent application Ser. No. 08/282,289, now abandoned, filed Jul. 19, 1994.

The present invention was made utilizing funds from the National Institute of Ageing, grant numbers AG-05443, AG-05133 and AG-08974. This application is a continuation-in-part of U.S. patent application Ser. No. 08/640,704, now abandoned, and also a continuation-in-part of International Patent application, PCT/US96/05918, both filed May 1, 1996, which is a continuation-in-part of U.S. patent application Ser. No. 08/432,019, now abandoned, filed May 1, 1995, which is a continuation-in-part of U.S. patent application Ser. No. 08/282,289, now abandoned, filed Jul. 19, 1994.

BACKGROUND OF THE INVENTION

The present invention relates to the identification of compounds that are suitable for imaging amyloid deposits in living patients. More specifically, the present invention relates to a method of imaging amyloid deposits in brain in vivo to allow antemortem diagnosis of Alzheimer's Disease. The present invention also relates to therapeutic uses for such compounds.

Alzheimer's Disease ("AD") is a neurodegenerative illness characterized by memory loss and other cognitive deficits. McKhann et al., *Neurology* 34: 939 (1984). It is the most common cause of dementia in the United States. AD can strike persons as young as 40–50 years of age. Yet, because the presence of the disease is difficult to determine without dangerous brain biopsy, the time of onset is unknown. The prevalence of AD increases with age, with estimates of the affected population reaching as high as 40–50% by ages 85–90. Evans et al., *JAMA* 262: 2551 (1989); Katzman, *Neurology* 43: 13 (1993).

By definition, AD is definitively diagnosed through examination of brain tissue, usually at autopsy. Khachaturian, *Arch. Neurol.* 42: 1097 (1985); McKhann et al., *Neurology* 34: 939 (1984). Neuropathologically, this disease is characterized by the presence of neuritic plaques (NP), neurofibrillary tangles (NFT), and neuronal loss, along with a variety of other findings. Mann, *Mech. Ageing Dev.* 31: 213 (1985). Post-mortem slices of brain tissue of victims of Alzheimer's disease exhibit the presence of amyloid in the form of proteinaceous extracellular cores of the neuritic plaques that are characteristic of AD.

The amyloid cores of these neuritic plaques are composed of a protein called the β-amyloid (Aβ) that is arranged in a predominately beta-pleated sheet configuration. Mori et al., *Journal of Biological Chemistry* 267: 17082 (1992); Kirschner et al., *PNAS* 83: 503 (1986). Neuritic plaques are an early and invariant aspect of the disease. Mann et al., *J. Neurol. Sci.* 89: 169; Mann, *Mech. Ageing Dev.* 31: 213 (1985); Terry et al., *J. Neuropathol. Exp. Neurol* 46: 262 (1987).

The initial deposition of Aβ probably occurs long before clinical symptoms are noticeable. The currently recommended "minimum microscopic criteria" for the diagnosis of AD is based on the number of neuritic plaques found in brain. Khachaturian, *Arch. Neurol.*, supra (1985). Unfortunately, assessment of neuritic plaque counts must be delayed until after death.

Amyloid-containing neuritic plaques are a prominent feature of selective areas of the brain in AD as well as Downs Syndrome and in persons homozygous for the apolipoprotein E4 allele who are very likely to develop AD. Corder et al., *Science* 261: 921 (1993); Divry, P., *J. Neurol. Psych.* 27: 643–657 (1927); Wisniewski et al., in Zimmerman, H. M. (ed.): PROGRESS IN NEUROPATHOLOGY, (Grune and Stratton, N.Y. 1973) pp. 1–26. Brain amyloid is readily demonstrated by staining brain sections with thioflavin S or Congo red. Puchtler et al., *J. Histochem. Cytochem.* 10: 35 (1962). Congo red stained amyloid is characterized by a dichroic appearance, exhibiting a yellow-green polarization color. The dichroic binding is the result of the beta-pleated sheet structure of the amyloid proteins. Glenner, G. *N. Eng. J. Med.* 302: 1283 (1980). A detailed discussion of the biochemistry and histochemistry of amyloid can be found in Glenner, *N. Eng. J. Med.*, 302: 1333 (1980).

Thus far, diagnosis of AD has been achieved mostly through clinical criteria evaluation, brain biopsies and post mortem tissue studies. Research efforts to develop methods for diagnosing Alzheimer's disease in vivo include (1) genetic testing, (2) immunoassay methods and (3) imaging techniques.

Evidence that abnormalities in Aβ metabolism are necessary and sufficient for the development of AD is based on the discovery of point mutations in the Aβ precursor protein in several rare families with an autosomal dominant form of AD. Hardy, *Nature Genetics* 1: 233 (1992); Hardy et al., *Science* 256: 184 (1992). These mutations occur near the N- and C-terminal cleavage points necessary for the generation of Aβ from its precursor protein. St. George-Hyslop et al., *Science* 235: 885 (1987); Kang et al., *Nature* 325: 733 (1987); Potter WO 92/17152. Genetic analysis of a large number of AD families has demonstrated, however, that AD is genetically heterogeneous. St. George-Hyslop et al., *Nature* 347: 194 (1990). Linkage to chromosome 21 markers is shown in only some families with early-onset AD and in no families with late-onset AD. More recently a gene on chromosome 14 whose product is predicted to contain multiple transmembrane domains and resembles an integral membrane protein has been identified by Sherrington et al., *Nature* 375: 754–760 (1995). This gene may account for up to 70% of early-onset autosomal dominant AD. Preliminary data suggests that this chromosome 14 mutation causes an increase in the production of Aβ. Scheuner et al., *Soc. Neurosci. Abstr.* 21: 1500 (1995). A mutation on a very similar gene has been identified on chromosome 1 in Volga German kindreds with early-onset AD. Levy-Lahad et al., *Science* 269: 973–977 (1995).

Screening for apolipoprotein E genotype has been suggested as an aid in the diagnosis of AD. Scott, *Nature* 366: 502 (1993); Roses, *Ann. Neurol.* 38: 6–14 (1995). Difficulties arise with this technology, however, because the apolipoprotein E4 allele is only a risk factor for AD, not a disease marker. It is absent in many AD patients and present in many non-demented elderly people. Bird, *Ann. Neurol.* 38: 2–4 (1995).

Immunoassay methods have been developed for detecting the presence of neurochemical markers in AD patients and to detect an AD related amyloid protein in cerebral spinal fluid. Warner, *Anal. Chem.* 59: 1203A (1987); World Patent No. 92/17152 by Potter; Glenner et al., U.S. Pat. No. 4,666,829. These methods for diagnosing AD have not been proven to detect AD in all patients, particularly at early stages of the disease and are relatively invasive, requiring a spinal tap. Also, attempts have been made to develop monoclonal antibodies as probes for imaging of Aβ. Majocha et al., *J. Nucl. Med.*, 33: 2184 (1992); Majocha et al., WO 89/06242 and Majocha et al., U.S. Pat. No. 5,231,000. The major disadvantage of antibody probes is the difficulty in getting these large molecules across the blood-brain barrier. Using antibodies for in vivo diagnosis of AD would require marked abnormalities in the blood-brain barrier in order to gain access into the brain. There is no convincing functional evidence that abnormalities in the blood-brain barrier reliably exist in AD. Kalaria, *Cerebrovascular & Brain Metabolism Reviews* 4: 226 (1992).

Aβ antibodies are also disadvantageous for use in AD diagnostics because they typically stain deposits of Aβ containing non-β-sheet (non-fibrillar) Aβ in addition to the neuritic plaques. Yamaguchi et al., *Acta Neuropathol.*, 77: 314 (1989). These deposits may be a separate type of lesion, not necessarily involved in the dementing process of AD. The latter is suggested by findings of nonfibrillar amyloid deposits in cognitively normal controls and aged dogs. Moran et al., *Medicina Clinica* 98: 19 (1992); Shimada et al., *Journal of Veterinary Medical Science* 54: 137 (1992); Ishihara et al., *Brain Res.* 548: 196 (1991); Giaccone et al., *Neurosci. Lett.* 114: 178 (1990). Even if non-fibrillar amyloid deposits are forerunners of neuritic plaques, the key pathological event in AD may be the process that turns the apparently benign non-fibrillar amyloid deposit into the neuritic plaque with its associated halo of degeneration. Therefore, a probe is needed that is specific for the fibrillar Aβ deposits and NFTs as a more specific marker for AD pathophysiology than antibodies that would also label non-fibrillar amyloid deposits.

Recently, radiolabeled Aβ peptide has been used to label diffuse, compact and neuritic type plaques in sections of AD brain. Maggio et al., WO 93/04194. However, these peptides share all of the disadvantages of antibodies. Specifically, peptides do not normally cross the blood-brain barrier in amounts necessary for imaging.

Congo red may be used for diagnosing amyloidosis in vivo in non-brain parenchymal tissues. However, Congo red is probably not suitable for in vivo diagnosis of Aβ deposits in brain because only 0.03% of an injected dose of iodinated Congo red can enter the brain parenchyma. Tubis et al., *J. Amer. Pharm. Assn.* 49: 422 (1960). Radioiodinated bisdiazobenzidine compounds related to Congo red, such as Benzo Orange R and Direct Blue 4, have been proposed to be useful in vitro and in vivo to detect the presence and location of amyloid deposits in an organ of a patient. Quay et al., U.S. Pat. Nos. 5,039,511 and 4,933,156. However, like Congo red, all of the compounds proposed by Quay contain strongly acidic sulfonic acid groups which severely limit entry of these compounds into the brain making it extremely difficult to attain an imaging effective quantity or detectable quantity in the brain parenchyma.

The inability to assess amyloid deposition in AD until after death impedes the study of this devastating illness. A method of quantifying amyloid deposition before death is needed both as a diagnostic tool in mild or clinically confusing cases as well as in monitoring the effectiveness of therapies targeted at preventing Aβ deposition. Therefore, it remains of utmost importance to develop a safe and specific method for diagnosing AD before death by imaging amyloid in brain parenchyma in vivo. Even though various attempts have been made to diagnose AD in vivo, currently, there are no antemortem probes for brain amyloid. No method has utilized a high affinity probe for amyloid that has low toxicity, can cross the blood-brain barrier, and binds more effectively to AD brain than to normal brain in order to identify AD amyloid deposits in brain before a patient's death. Thus, no in vivo method for AD diagnosis has been demonstrated to meet these criteria.

Very recent data suggest that amyloid-binding compounds will have therapeutic potential in AD and type 2 diabetes mellitus. As mentioned above, there are two broad categories of plaques in AD brain, diffuse and neuritic (classical). Diffuse plaques do not appear to induce morphological reactions such as the reactive astrocytes, dystrophic neurites, microglia cells, synapse loss, and full complement activation found in neuritic plaques. Joachim et al., *Am. J. Pathol.* 135: 309 (1989); Masliah et al., loc. cit. 137: 1293 (1990); Lue and Rogers, *Dementia* 3: 308 (1992). These morphological reactions all signify that neurotoxic and cell degenerative processes are occurring in the areas adjacent to the fibrillar Aβ deposits of neuritic plaques. Aβ-induced neurotoxicity and cell degeneration has been reported in a number of cell types in vitro. Yankner et al., *Science* 250: 279 (1990); Roher et al., *BBRC* 174: 572 (1991); Frautschy et al., *Proc. Natl. Acad. Sci.* 88: 83362 (1991); Shearman et al., loc. cit. 91: 1470 (1994). It has been shown that aggregation of the Aβ peptide is necessary for in vitro neurotoxicity. Yankner, *Neurobiol. Aging* 13: 615 (1992). Differences in the state of aggregation of Aβ in diffuse and neuritic plaques may explain the lack of neurotoxic response surrounding the diffuse plaque. Lorenzo and Yankner, *Proc. Natl. Acad. Sci.*, 91: 12243 (1994). Recently, three laboratories have reported results which suggest that Congo red inhibits Aβ-induced neurotoxicity and cell degeneration in vitro. Burgevin et al., *NeuroReport* 5: 2429 (1994); Lorenzo and Yankner, *Proc. Natl. Acad. Sci.* 91: 12243 (1994); Pollack et al., *Neuroscience Letters* 184: 113 (1995); Pollack et al., *Neuroscience Letters* 197: 211 (1995). The mechanism appears to involve both inhibition of fibril formation and prevention of the neurotoxic properties of formed fibrils. Lorenzo and Yankner, *Proc. Natl. Acad. Sci.* 91: 12243 (1994). Congo red also has been shown to protect pancreatic islet cells from the toxicity caused by amylin. Lorenzo and Yankner, *Proc. Natl. Acad. Sci.* 91: 12243 (1994). Amylin is a fibrillar peptide similar to Aβ which accumulates in the pancreas in type 2 diabetes mellitus.

It is known in the art that certain azo dyes may be carcinogenic. Morgan et al. *Environmental Health Perspectives*, 102 (supp.) 2: 63–78, (1994). This potential carcinogenicity appears to be based largely on the fact that azo dyes are extensively metabolized to the free parent amine by intestinal bacteria. Cerniglia et al., *Biochem. Biophys. Res. Com.*, 107: 1224–1229, (1982). In the case of benzidine dyes (and many other substituted benzidines), it is the free amine which is the carcinogen. These facts have little implication for amyloid imaging studies in which an extremely minute amount of the high specific activity radio-labelled dye would be directly injected into the blood stream. In this case, the amount administered would be negligible and the dye would by-pass the intestinal bacteria.

In the case of therapeutic usage, these facts have critical importance. Release of a known carcinogen from a therapeutic compound is unacceptable. A second problem with diazo dye metabolism is that much of the administered drug is metabolized by intestinal bacteria prior to absorption. This lowered bioavailability remains a disadvantage even if the metabolites released are innocuous.

Thus, a need exists for amyloid binding compounds which are similar to Congo red but which enter the brain (Congo Red does not). Such compounds could be used in preventing cell degeneration associated with fibril formation and thereby treat pathological conditions in amyloid associated diseases, such as AD and Downs Syndrome and in treating pancreatic islet cell toxicity in type 2 diabetes mellitus.

A further need exists for amyloid binding compounds that are non-toxic and bioavailable and, consequently, can be used in therapeutics.

SUMMARY OF THE INVENTION

It therefore is an object of the present invention to provide a safe, specific method for diagnosing AD before death by in vivo imaging of amyloid in brain parenchyma. It is another object of the present invention to provide an approach for identifying AD amyloid deposits in brain before a patient's death, using a high-affinity probe for amyloid which has low toxicity, can cross the blood-brain barrier, and can distinguish AD brain from normal brain. It is another object to provide a treatment for AD which will prevent the deposition or toxicity of Aβ. It is another object to provide a technique for staining and detecting amyloid deposits in biopsy or post-mortem tissue specimens. It is another object to provide a method for quantifying amyloid deposition in homogenates of biopsy or post-mortem tissue specimens.

In accomplishing these and other objects, there has been provided, in accordance with one aspect of the present invention, an amyloid binding compound of Formula I or a water soluble, non-toxic salt thereof:

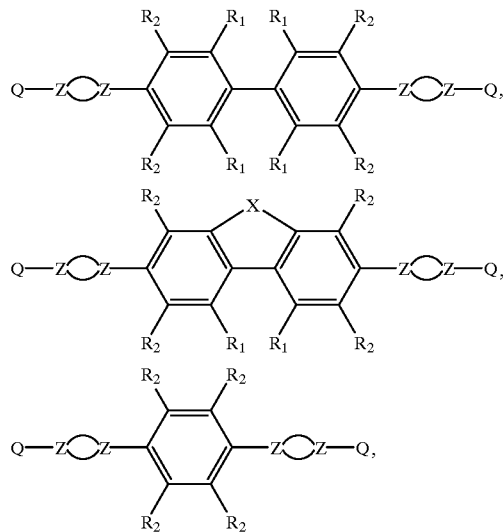

(I)

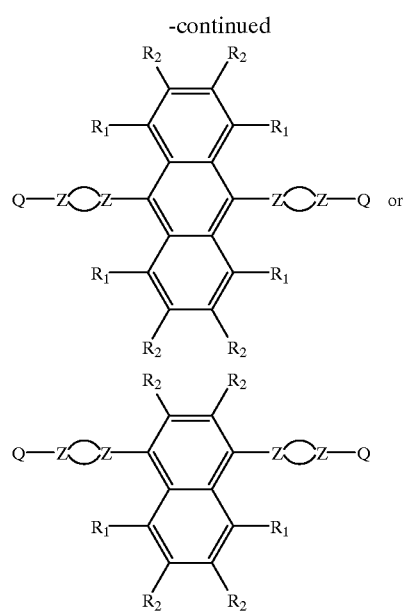

wherein:

is either C≡C, CR'=CR', or CR'$_2$—CR'$_2$ (where R' represents H or a lower alkyl group);

X is C(R")$_2$
(wherein each R" independently is H, F, Cl, Br, I, a lower alkyl group, (CH$_2$)$_n$OR' where n=1, 2, or 3, CF$_3$, CH$_2$—CH$_2$F, O—CH$_2$—CH$_2$F, CH$_2$—CH$_2$—CH$_2$F, O—CH$_2$—CH$_2$—CH$_2$F, CN, (C=O)—R', N(R')$_2$, NO$_2$, (C=O)N(R')$_2$O(CO)R', OR', SR', COOR', R$_{Ph}$, CR'=CR'—R$_{Ph}$, CR'$_2$—CR'$_2$—R$_{Ph}$ (where R$_{ph}$ represents an unsubstituted or substituted phenyl group with the phenyl substituents being chosen from any of the non-phenyl substituents defined for R", a tri-alkyl tin, a tetrazole or oxadiazole of the form:

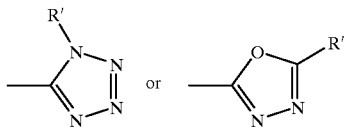

(wherein R' is H or a lower alkyl group)
or X is CR'=CR', N=N, C=O, O, NR' (where R' represents H or a lower alkyl group), S, or SO$_2$;
each R$_1$ and R$_2$ independently is H, F, Cl, Br, I, a lower alkyl group, (CH$_2$)$_n$OR' where n=1, 2, or 3, CF$_3$, CH$_2$—CH$_2$F, O—CH$_2$—CH$_2$F, CH$_2$—CH$_2$—CH$_2$F, O—CH$_2$—CH$_2$—CH$_2$F, CN, (C=O)—R', N(R')$_2$, NO$_2$, (C=O)N(R')$_2$O(CO)R', OR', SR', COOR', a tri-alkyl tin, R$_{Ph}$, CR'=CR'R$_{Ph}$, CR'$_2$—CR'$_2$—R$_{Ph}$ (where R$_{ph}$ represents an unsubstituted or substituted phenyl group with the phenyl substituents being chosen from any of the non-phenyl substituents defined for R$_1$ and R$_2$, a tetrazole or oxadiazole of the form:

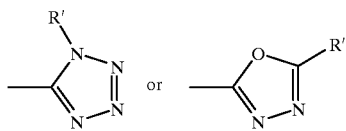 or (wherein R' is H or a lower alkyl group), or a triazene of the form:

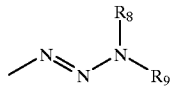

wherein $R_8$ and $R_9$ are lower alkyl groups) or

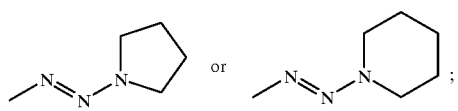 ;

each Q is independently selected from one of the following structures:
IA, IB, IC, ID, IE, IF and IG, wherein
IA has the following structure:

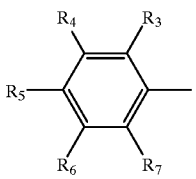

(IA)

wherein:
each of $R_3$, $R_4$, $R_5$, $R_6$, or $R_7$ independently is defined the same as $R_1$ above;
IB has the following structure:

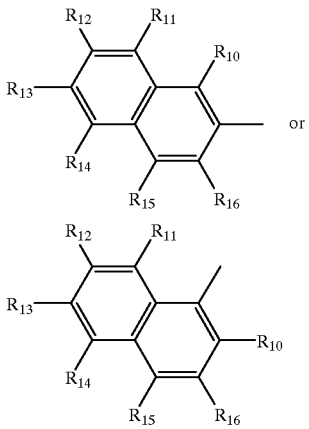

(IB)

wherein:
each of $R_{10}$, $R_{11}$, $R_{12}$, $R_{13}$, $R_{14}$, $R_{15}$, or $R_{16}$ independently is defined the same as $R_1$, above;

IC has the following structure:

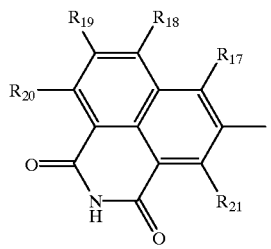

(IC)

wherein:
each of $R_{17}$, $R_{18}$, $R_{19}$, $R_{20}$, or $R_{21}$ independently is defined the same as $R_1$ above;
ID has the following structure:

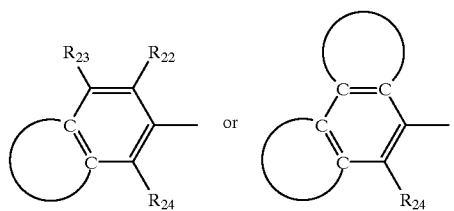

(ID)

wherein:
each of $R_{22}$, $R_{23}$, or $R_{24}$ independently is defined the same as $R_1$ above and 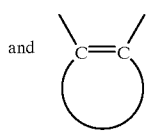

represents a heterocyclic ring of one of the six following formulas:

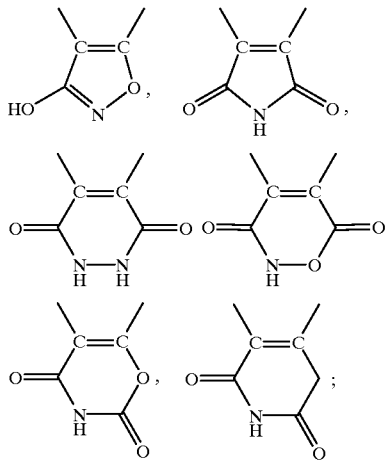 ;

IE has the following structure:

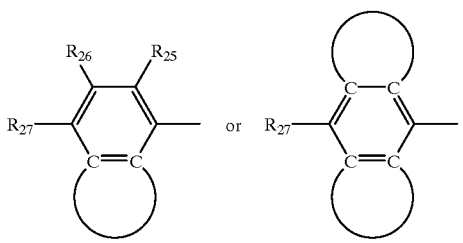

(IE)

wherein:

each of $R_{25}$, $R_{26}$, or $R_{27}$ independently is defined the same as $R_1$ above and 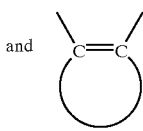

represents a heterocyclic ring of one of the six following formulas:

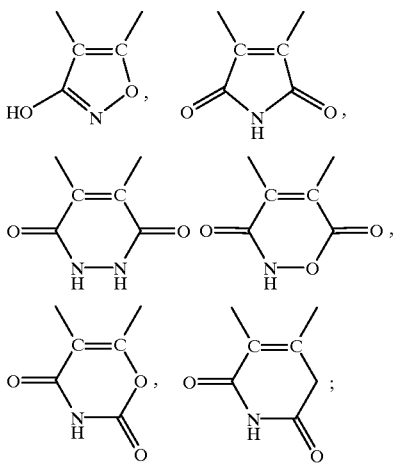

IF has the following structure:

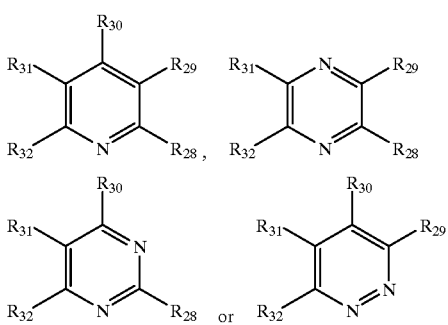

(IF)

wherein:

exactly one of $R_{28}$, $R_{29}$, $R_{30}$, $R_{31}$ or $R_{32}$ is the

link defined for Formula I above and each other $R_{28}$, $R_{29}$, $R_{30}$, $R_{31}$ or $R_{32}$ independently is defined the same as $R_1$ above;

IG has the following structure:

(IG)

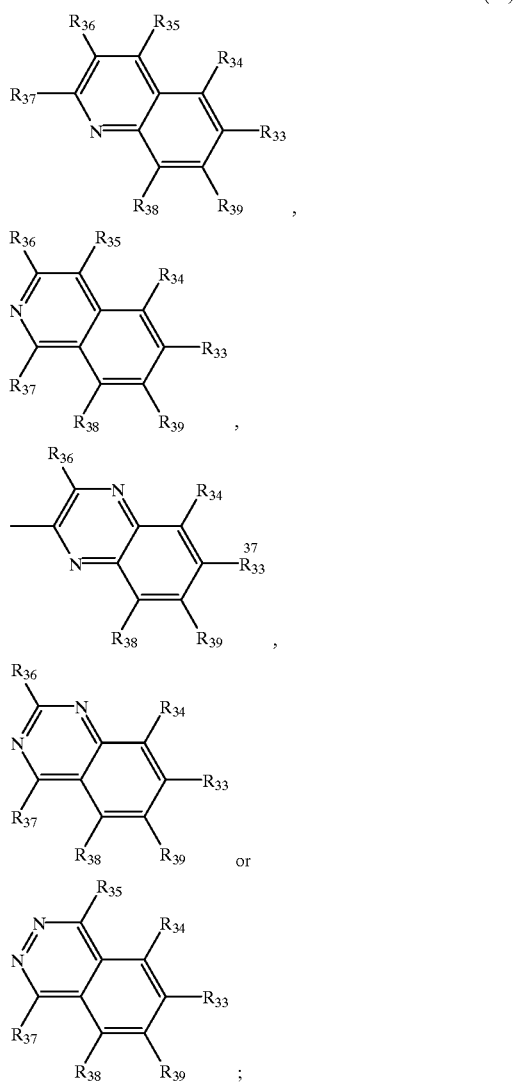

wherein:

exactly one of $R_{33}$, $R_{34}$, $R_{35}$, $R_{36}$, $R_{37}$, $R_{38}$, or $R_{39}$ is the

link defined for Formula I above and each other $R_{33}$, $R_{34}$, $R_{35}$, $R_{36}$, $R_{37}$, $R_{38}$, or $R_{39}$ independently is defined the same as $R_1$ above.

It is another object of the present invention to provide an amyloid binding compound of Formula I, as defined above, or a water soluble, non-toxic salt thereof, wherein at least one of the substituents $R_1$–$R_7$ and $R_{10}$–$R_{39}$ is selected from the group consisting of $^{131}I$, $^{123}I$, $^{76}Br$, $^{75}Br$, $^{18}F$, $^{19}F$, $^{125}I$, $CH_2$—$CH_2$—$^{18}F$, O—$CH_2$—$CH_2$—$^{18}F$, $CH_2$—$CH_2$—$CH_2$—$^{18}F$, O—$CH_2$—$CH_2$—$CH_2$—$^{18}F$ and a carbon-containing substituent as specified in Formula I wherein at least one carbon is $^{11}C$ or $^{13}C$.

It is a further object of the invention to provide an amyloid binding compound of Formula I, as defined above, or a water-soluble, non-toxic salt thereof, wherein the compound binds to Aβ with a dissociation constant ($K_D$) between 0.0001 and 10.0 μM when measured by binding to synthetic Aβ peptide or Alzheimer's Disease brain tissue.

Still another object of the present invention is to provide a method for synthesizing an amyloid binding compound of Formula I, as defined above, or a water soluble, non-toxic salt thereof, wherein at least one of the substituents $R_1$–$R_7$ and $R_{10}$–$R_{39}$ is selected from the group consisting of $^{131}I$, $^{123}I$, $^{76}Br$, $^{75}Br$, $^{18}F$ and $^{19}F$, comprising the step of reacting an amyloid binding compound of Formula I, as defined above, or a water soluble, non-toxic salt thereof wherein at least one of the substituents $R_1$–$R_7$ and $R_{10}$–$R_{39}$ is a tri-alkyl tin, with a halogenating agent containing $^{131}I$, $^{123}I$, $^{76}Br$, $^{75}Br$, $^{18}F$ or $^{19}F$.

An additional object of the present invention is a pharmaceutical composition for in vivo imaging of amyloid deposits, comprising (a) an amyloid binding compound of Formula I, as defined above, or a water soluble, non-toxic salt thereof, wherein at least one of the substituents $R_1$–$R_7$ and $R_{10}$–$R_{39}$ is selected from the group consisting of $^{131}I$, $^{123}I$, $^{76}Br$, $^{75}Br$, $^{18}F$, $^{19}F$ and a carbon-containing substituent as specified in Formula I wherein at least one carbon is $^{11}C$ or $^{13}C$, and (b) a pharmaceutically acceptable carrier.

Yet another object of the present invention is an in vivo method for detecting amyloid deposits in a subject, comprising the steps of: (a) administering a detectable quantity of the above pharmaceutical composition, and (b) detecting the binding of the compound to amyloid deposit in said subject. It is also an object of the present invention to provide an in vivo method for detecting amyloid deposits in a subject wherein the amyloid deposit is located in the brain of a subject. This method of the invention may be used in a subject who is suspected of having an amyloidosis associated disease or syndrome selected from the group consisting of Alzheimer's Disease, Down's Syndrome, and homozygotes for the apolipoprotein E4 allele.

Another object of the invention relates to pharmaceutical compositions and methods of preventing cell degeneration and toxicity associated with fibril formation in amyloidosis associated conditions such as AD and Type 2 diabetes mellitus. Such pharmaceutical compositions comprise alkyl, alkenyl and alkynyl derivatives of Chrysamine G and a pharmaceutically acceptable carrier. Such compounds would be non-toxic.

Another object of the invention relates to the use of the probes as a stain for the visualization and detection of amyloid deposits in biopsy or post-mortem tissue specimens.

Another object of this invention relates to the use of radiolabeled probes for the quantitation of amyloid deposits in biopsy or postmortem tissue specimens.

Another object relates to a method of distinguishing Alzheimer's disease brain from normal brain.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2A–2K illustrate the chemical structures of the alkenyl derivative of Chrysamine G and alkenyl tri-alkyl tin derivatives of analogues of Chrysamine G, in particular heterocyclic analogues. Note that these structures represent one-half of a molecule which is symmetric around the wavy bond shown in the upper right, except that the tri-alkyl tin moiety may only be on one side of the biphenyl group. The tri-alkyl tin derivatives are stable intermediate and immediate precursors for the preparation of high specific activity halogenated radioactive derivatives. The heterocyclic analogues represent alternative means of placing weakly acidic moieties in the same structural position as the moderately acidic carboxylic acid group of Chrysamine G. These tri-alkyl tin precursor compounds are shown in their protonated form, yet those of skill in the art recognize that their deprotonated forms and tautomers also are embraced by these drawings.

2A) alkenyl derivative of Chrysamine G.

2B) alkenyl tri-alkyl tin derivative of Chrysamine G;

2C) alkenyl tri-alkyl tin derivative of the 3-Hydroxy-1,2-benzisoxazole analogue;

2D) alkenyl tri-alkyl tin derivative of the phthalimide or isoindole-1,3(2H)-dione analogue;

2E) alkenyl tri-alkyl tin derivative of the phthalhydrazide or 2,3-benzodiazine-1,4(2H,3H)-dione analogue;

2F) alkenyl tri-alkyl tin derivative of the 2,3-benzoxazine-1,4(3H)-dione analogue;

2G) alkenyl tri-alkyl tin derivative of the (2H)1,3-benzoxazine-2,4(3H)-dione analogue;

2H) alkenyl tri-alkyl tin derivative of the (3H)2-benzazine-1,3(2H)-dione analogue;

2I) alkenyl tri-alkyl tin derivative of the 1,8-Naphthalimide analogue.

2J) alkenyl tri-alkyl tin derivative of the tetrazole analogue.

2K) alkenyl tri-alkyl tin derivative of the oxadiazole analogue.

Figure 3:
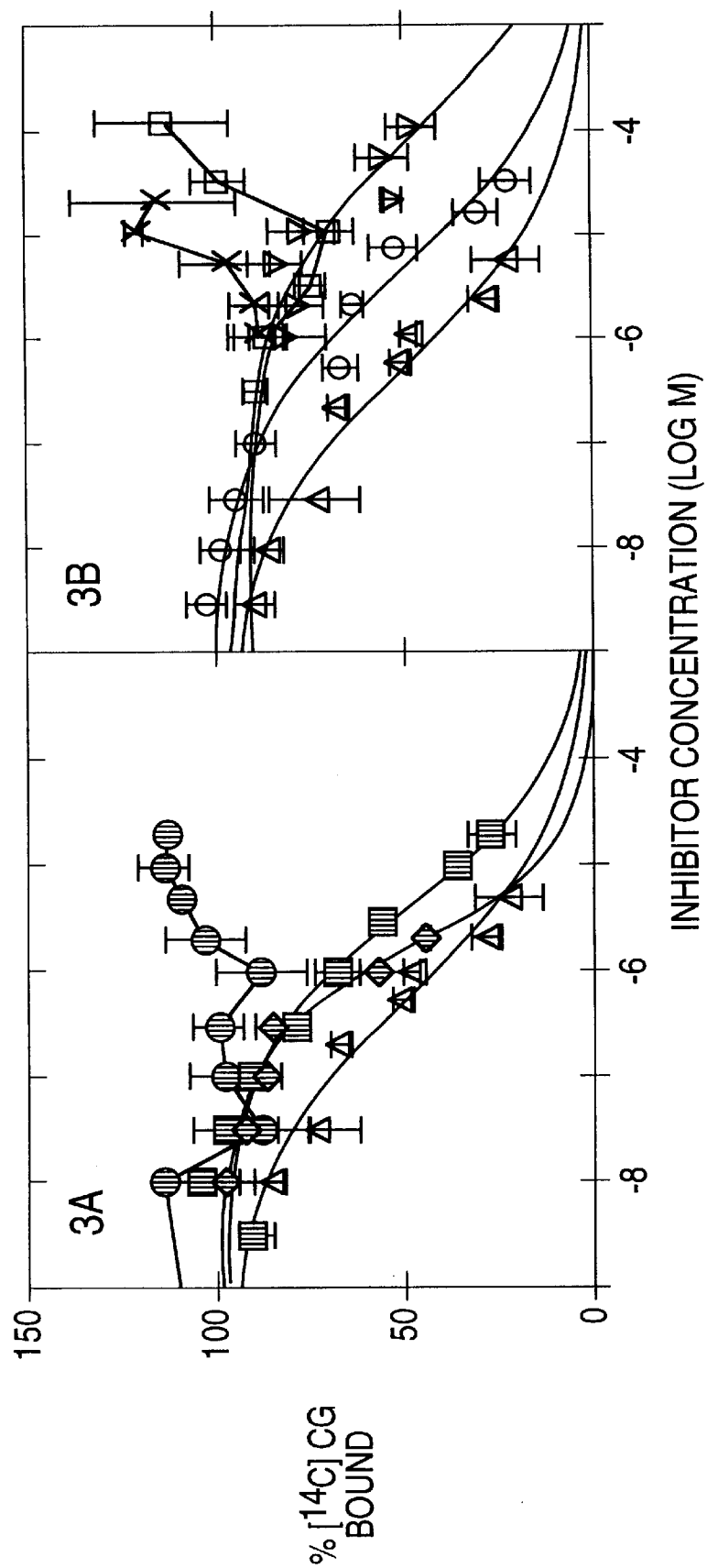

FIG. 3 Displacement curves of [$^{14}$C] Chrysamine G binding to Aβ (10–43) by several structural analogues of Chrysamine G. Abbreviations refer to those used in FIG. 1. FIG. 3A) Chrysamine G (open triangles); (5-FSA)CG (filled diamonds); 3,3'-(COOH)$_2$CG (filled squares); 2,2'-(SO$_3$)$_2$CG (filled circles). FIG. 3B) Chrysamine G (open triangles); Congo red (open circles); aniline derivative (open inverted triangles); phenol derivative (open squares); salicylic acid (X's). Curves which show increased binding at higher concentrations do so because of the formation of micelles. Bedaux, F. et al., *Pharm. Weekblad* 98: 189 (1963).

FIG. 4A is a Scatchard plot of Chrysamine G binding to Aβ (10–43). The curved line represents a nonlinear least-squares fit to a two, independent binding site model. The straight lines represent the individual components.

FIG. 4B is a Scatchard analysis of [$^{14}$C] CG binding to typical control (diamonds) and AD brain samples (squares). The dashed line has the same slope as the AD line and is meant to aid in the comparison with the control slope. This AD brain sample had 48 NP/xx200 magnification, a $K_D$ of 0.35 μM, and a $B_{max}$ of 790 fmol/μg protein. The control had a $K_D$ Of 0.48 μM, and a $B_{max}$ of 614 fmol/μg protein.

Figure 5:
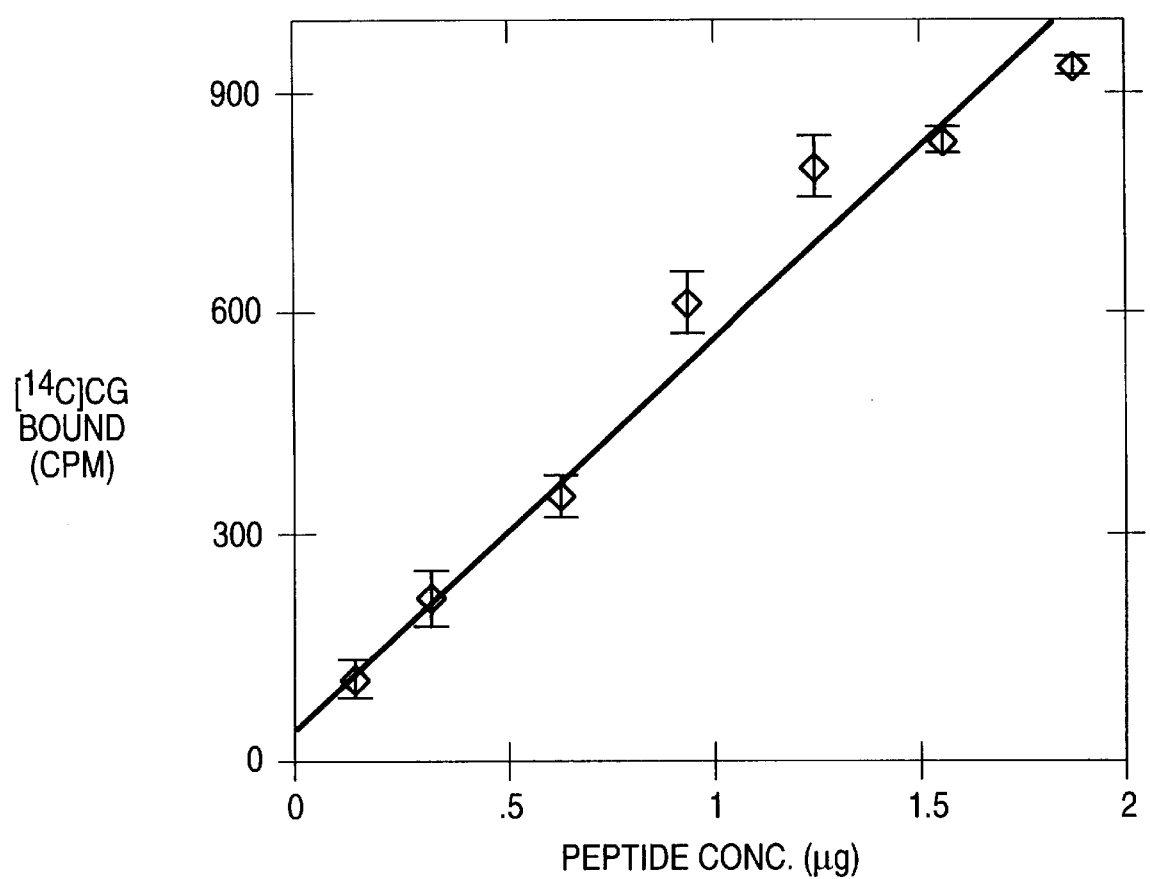

FIG. 5 is a graph illustrating the linearity of the binding assay with respect to peptide concentration. Approximately 0.9 μg of Aβ(10–43) was used in the typical assay.

Figure 6:
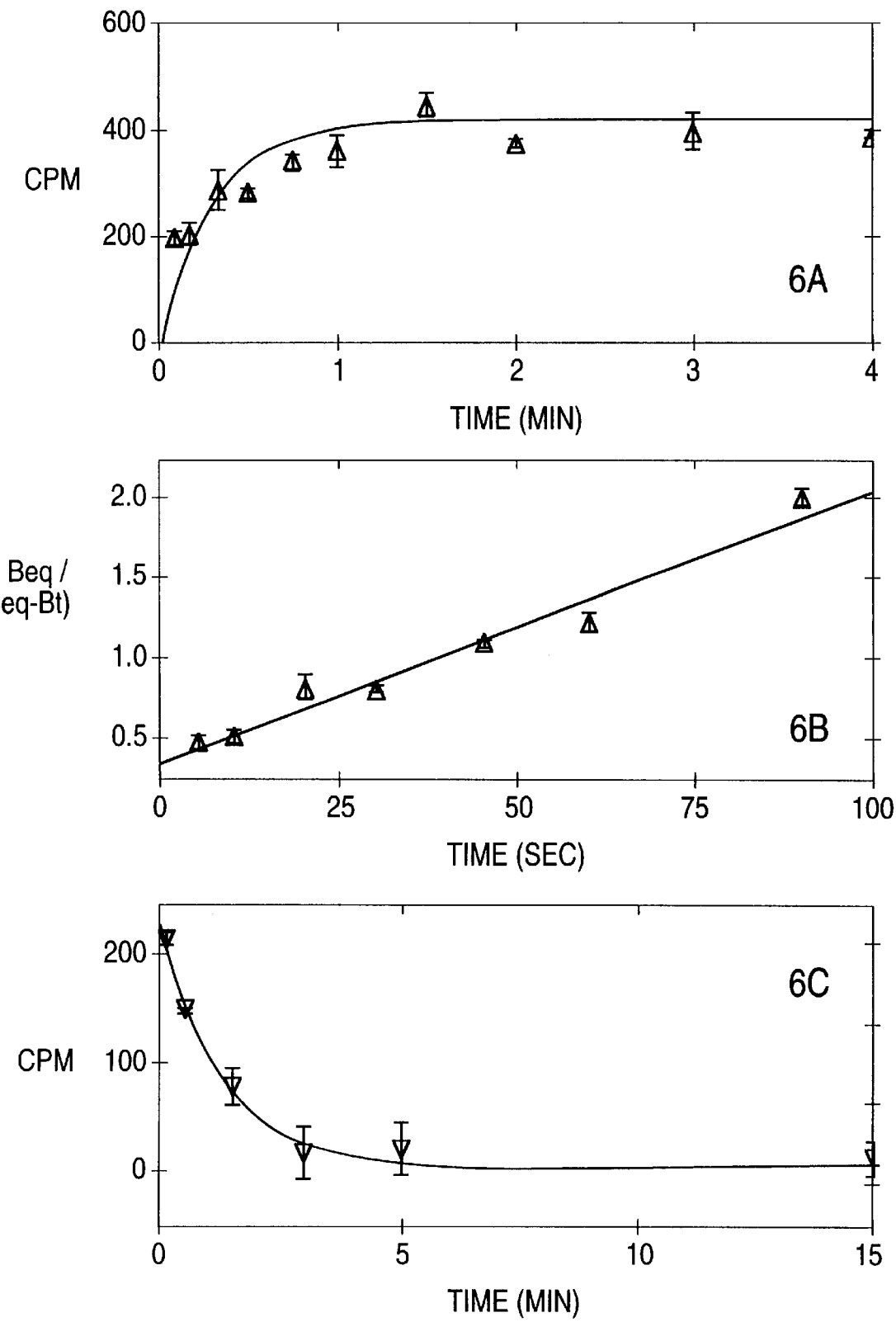

FIG. 6A is a graph illustrating the time course of association of Chrysamine G and Aβ(10–43).

FIG. 6B is the graphic illustration of the determination of the association rate constant ($k_1$).

FIG. 6C is a graph of the time course of dissociation of Chrysamine G from Aβ(10–43).

Figure 7:
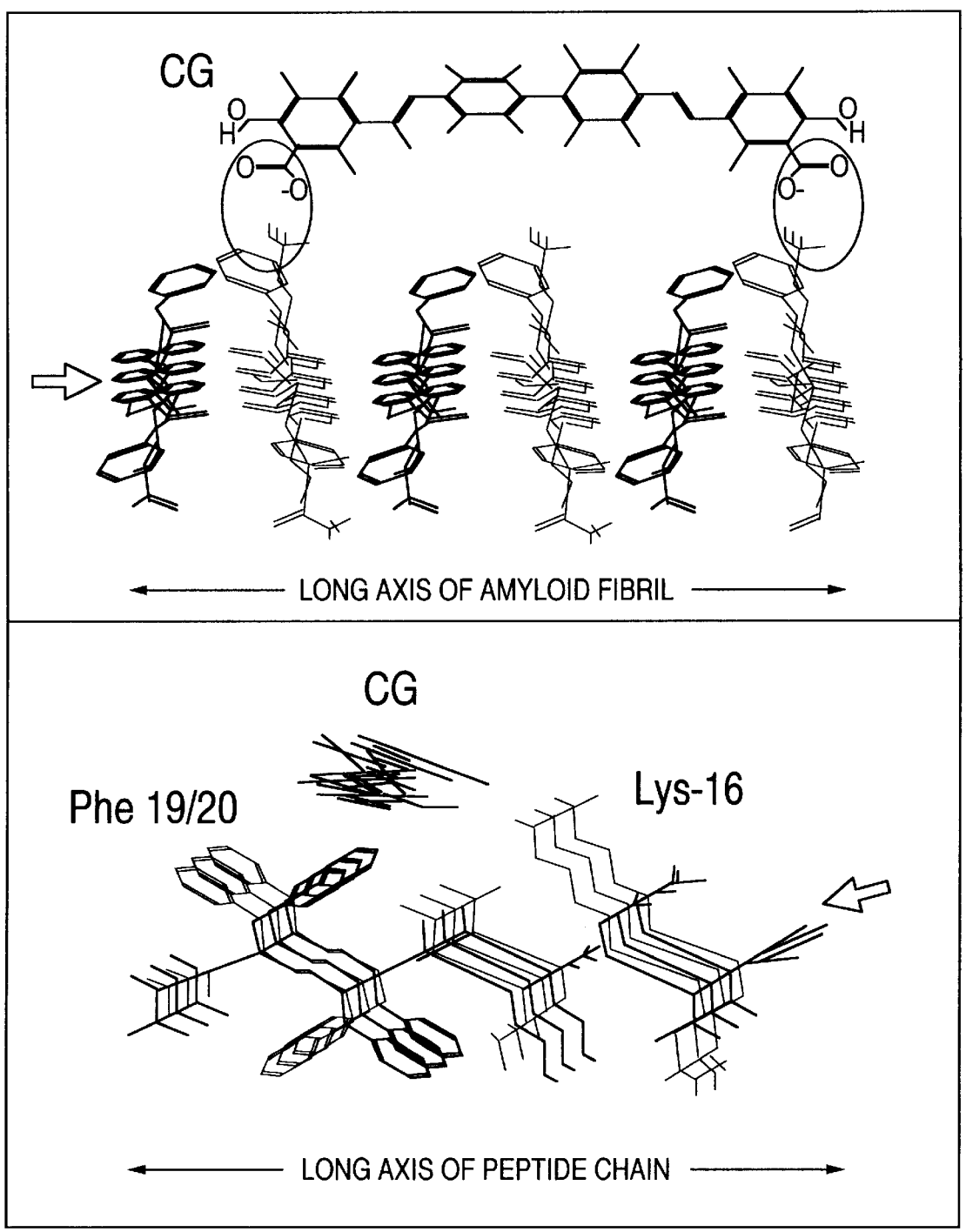

FIG. 7 is a graphic representation of a molecular model of the interaction between Chrysamine G and Aβ.

Figure 8:
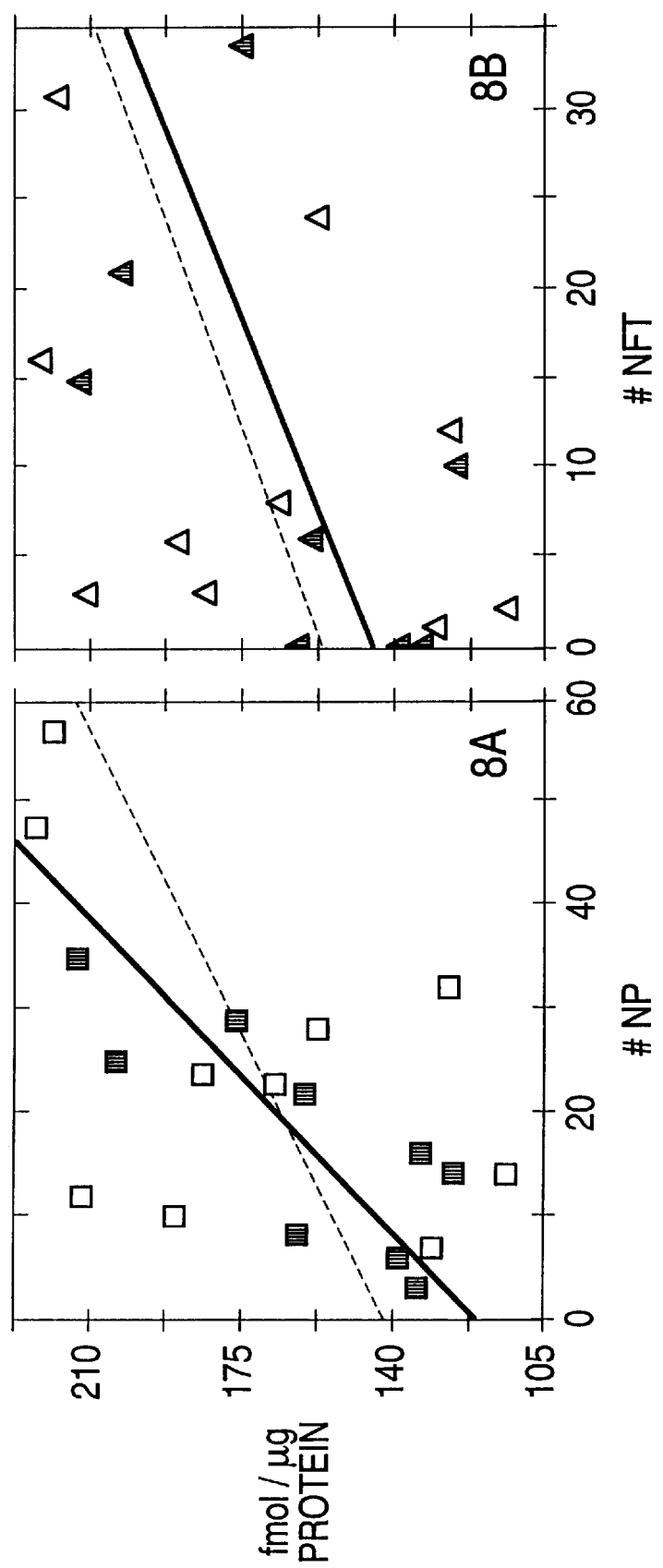

FIG. 8A is a graph illustrating the correlation between the amount of [$^{14}$C] Chrysamine G bound and the number of neuritic plaques (NP) in AD brain samples.

FIG. 8B is a graph illustrating the correlation between the amount of [$^{14}$C] Chrysamine G bound and the number of neurofibrillary tangles (NFT) in AD brain samples. In both FIGS. 8A and 8B, the x-axis represents the average NP or NFT count per field at x200 magnification in Bielschowsky stained sections of either the superior/middle frontal (n=10) or superior temporal cortex (n=10). The filled symbols and heavy lines indicate brains without amyloid angiopathy, the open symbols and dashed lines indicate brains with amyloid angiopathy. The y-axis represents total, absolute [$^{14}$C] Chrysamine G binding (fmol/μg protein) in homogenates of brain samples adjacent to those used for staining. Approximately 75 μg protein and 150 nM [$^{14}$C]Chrysamine G were used.

FIGS. 9A, 9B and 9C. The binding of Chrysamine G to various brain areas in samples of AD brain having more than 20 NPs/x200 magnification, referred to as "High Plaque AD Brains", is shown in FIG. 9A. The binding of Chrysamine G to brain areas in samples of AD brain having less than 20 NPs/x200 magnification, referred to as "Low Plaque AD Brains", is shown in FIG. 9B. The data points represent the ratio of [$^{14}$C]Chrysamine G binding in the designated brain area to [$^{14}$C]Chrysamine G binding in the cerebellum (CB) of the same brain. Horizontal bars represent the mean and error bars represent the standard error for control (circles), and AD brain (diamonds in 9A and 9B). Brain areas include the frontal pole (FP), head of caudate (CAU), superior/middle frontal (SMF), superior temporal (ST), inferior parietal (IP), and occipital (OC) cortex. Asterisks indicate significant differences compared to control (*p<0.05; **p<0.001). Two Down's syndrome brain samples are indicated in FIG. 9C. The diamonds in 9C represent a brain from a 23 year old Down's syndrome patient not yet symptomatic with AD. The triangles in 9C represent a 51 year old Down's syndrome patient who had developed AD as do the vast majority of Down's syndrome patients by their 40's.

Figure 10:
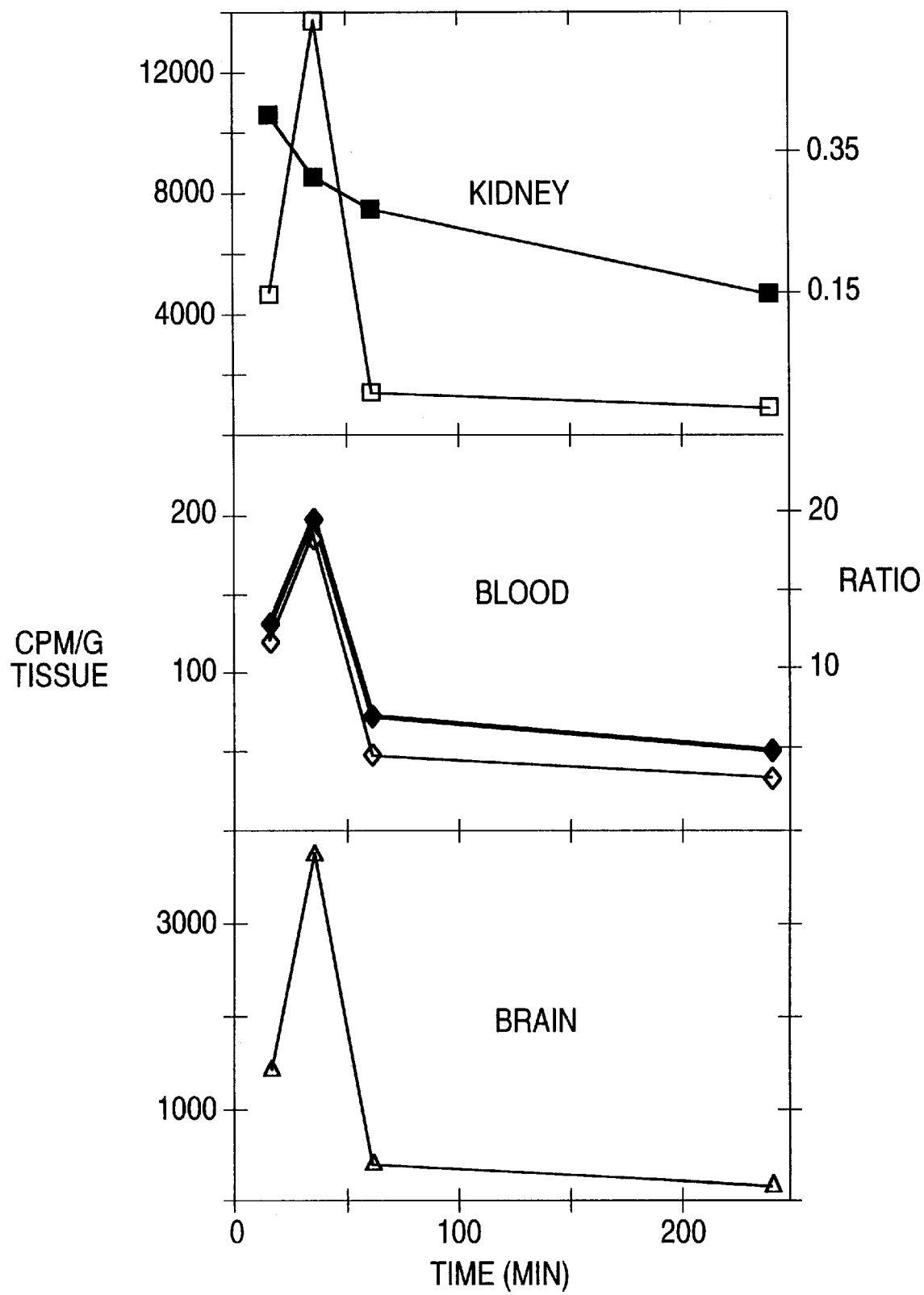

FIG. 10 is a graph illustrating the tissue levels of Chrysamine G in mice injected with [$^{14}$C]Chrysamine G in the lateral tail vein and sacrificed at the times indicated. The open symbols and thin lines represent absolute radioactivity in units of cpm/g tissue (left axis). The closed symbols and solid lines represent the ratio of brain radioactivity to that in kidney (top) or blood (middle). The ratios are plotted on the right axis.

Figure 11:
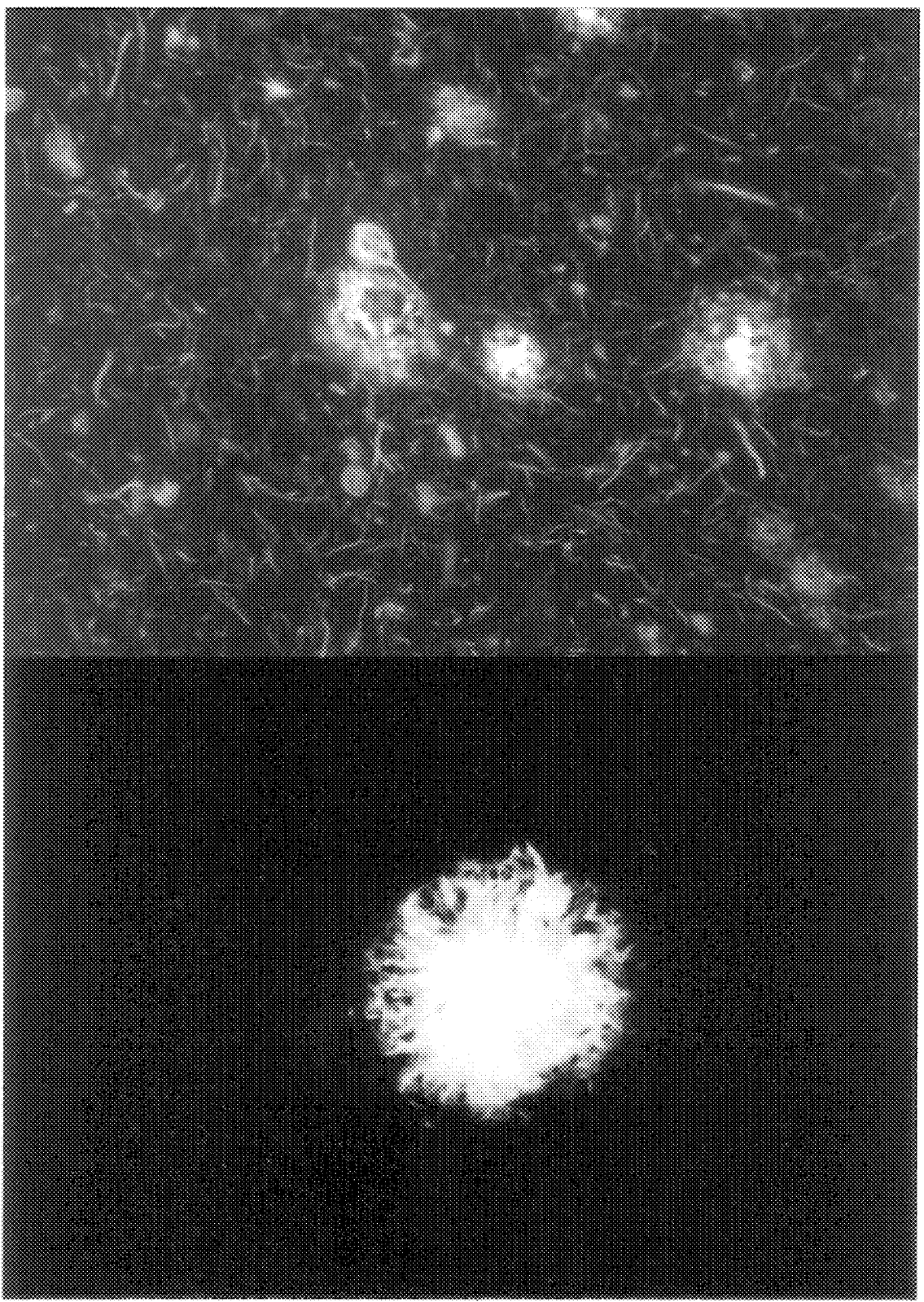

FIG. 11. TOP: Section from the inferior temporal lobe of AD brain stained with 1,4-bis(3-carboxy-4-hydroxyphenylethenyl)-benzene by the method of Stokes and Trickey, *J. Clin. Pathol.* 26: 241–242 (1973). Visible are a large number of neuritic plaques, a neurofibrillary tangle and frequent neuropil threads. Cerebrovascular amyloid also is intensely stained (not shown). The photomicrograph was obtained using fluorescence microscopy. BOTTOM: Section of transgenic mouse brain [Tg(HuAPP695.SWE)2576; Hsiao et al. *Science* 274: 99–102 (1996)] similarly stained with 1,4-bis(3-carboxy-4-hydroxyphenylethenyl)-benzene showing an intensely stained plaque.

Figure 12:
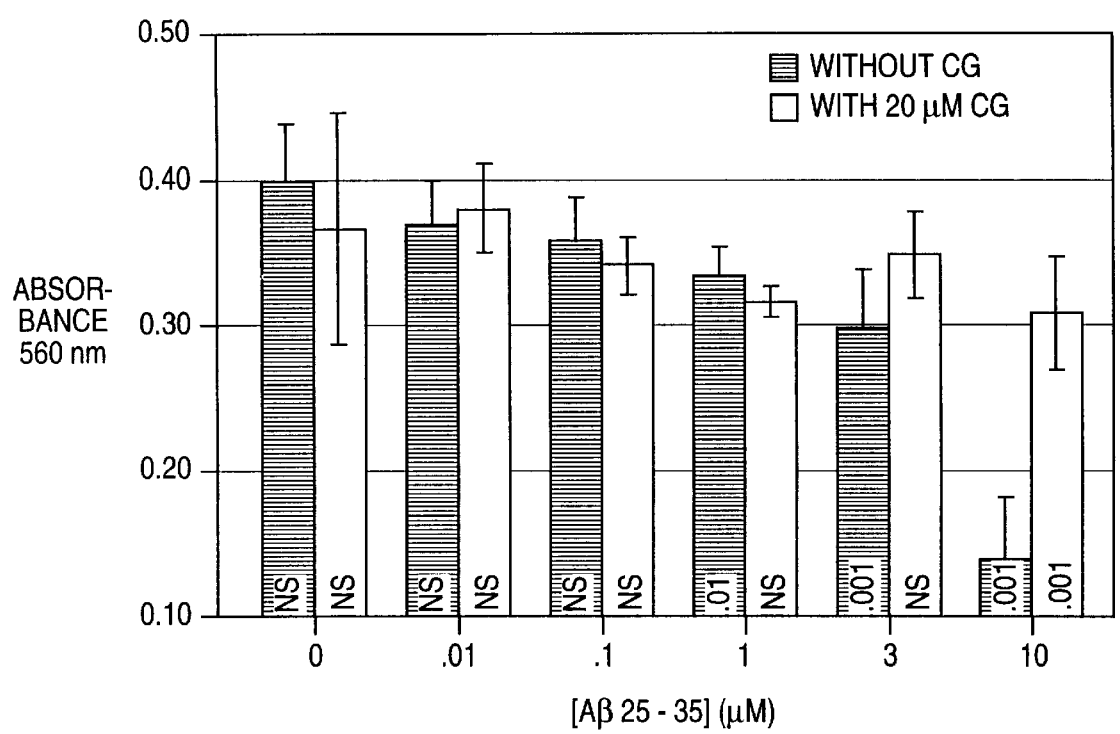

FIG. 12. A bar graph showing the effect of increasing concentrations of Aβ(25–35) in the presence and absence of Chrysamine G on the cellular redox activity of rat pheochromocytoma (PC-12) cells as measured by 3-[4,5-dimethylthiazol-2-yl]-2,5-diphenyltetrazolium bromide, MTT, reduction. The reduction product of MTT absorbs at 560 nm which is plotted on the vertical axis. The effect of Aβ(25–35) alone is shown in the filled bars and shows a dose dependent decrease in MTT reduction. Significant differences from control (no Aβ(25–35), no Chrysamine G) are shown in white inside the filled bars. The protective effect of 20 μM Chrysamine G is shown in the open bars. Significant differences between MTT reduction in the presence and absence of Chrysamine G are shown in black inside the open bars.

Figure 13:
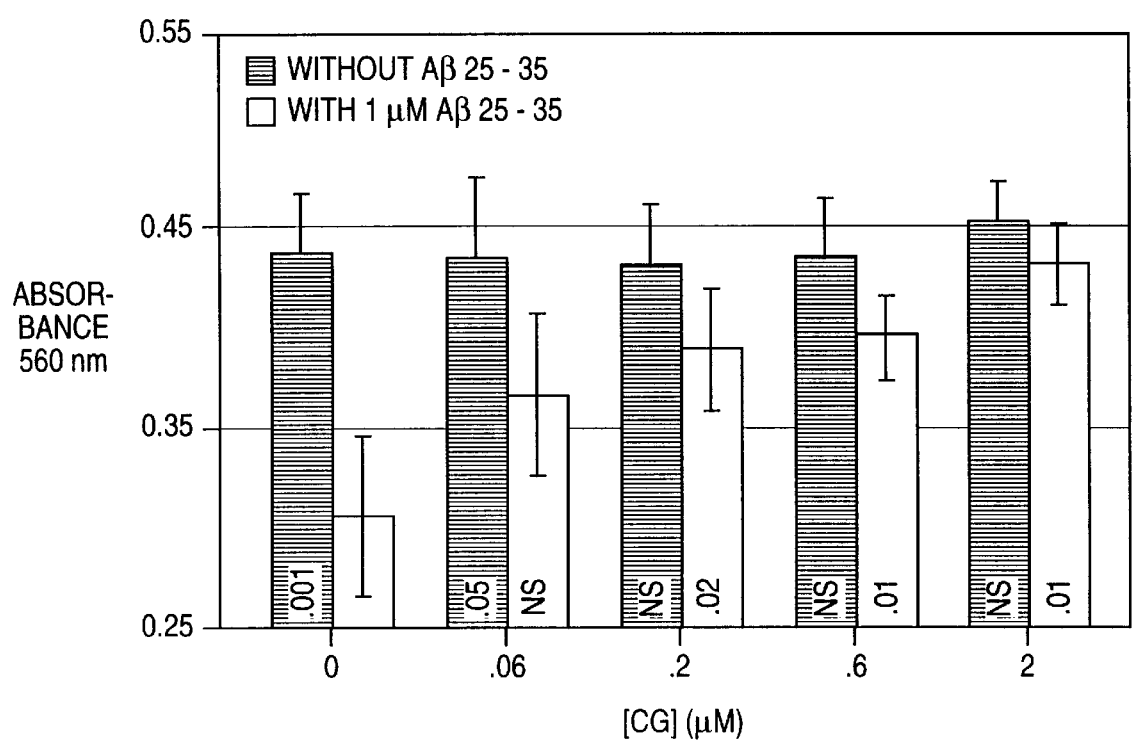

FIG. 13. A bar graph showing the protective effect of increasing concentrations of Chrysamine G against the Aβ(25–35)-induced reduction of cellular redox activity of rat pheochromocytoma (PC-12) cells as measured by 3-[4,5-dimethylthiazol-2-yl]-2,5-diphenyltetrazolium bromide, MTT, reduction. The reduction product of MTT absorbs at 560 nm which is plotted on the vertical axis. The effect of Chrysamine G in the absence of Aβ(25–35) is shown in the filled bars. There was no significant difference between control (no Aβ(25–35), no Chrysamine G) and any of the concentrations of Chrysamine G in the absence of Aβ(25–35). MTT reduction in the presence of 1 μM Aβ(25–35) and increasing concentrations of Chrysamine G is shown in the open bars. Significant differences in MTT reduction between the presence and absence of Aβ(25–35) at each concentration of Chrysamine G are shown in white inside the filled bars. Significant differences in MTT reduction between the Aβ(25–35) control (no Chrysamine G) and Aβ(25–35) plus increasing concentrations of Chrysamine G are shown in black inside the open bars.

Figure 14:
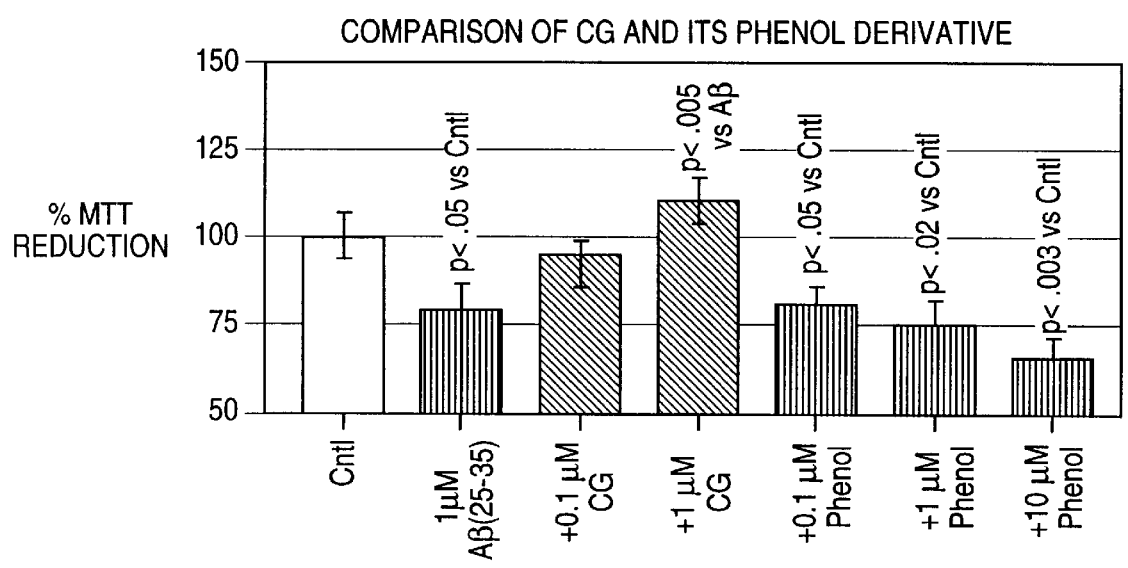

FIG. 14. Comparison of the effects of Chrysamine-G and the inactive phenol derivative on the toxicity induced by Aβ(25–35). 1 μM Aβ(25–35) was present in all experiments except control. Chrysamine-G showed protective effects at 0.1 and 1 μM, but the phenol derivative showed no protective effects, and perhaps enhanced the toxicity of Aβ.

DETAILED DESCRIPTION OF THE REFERRED EMBODIMENTS

Figure 1A:
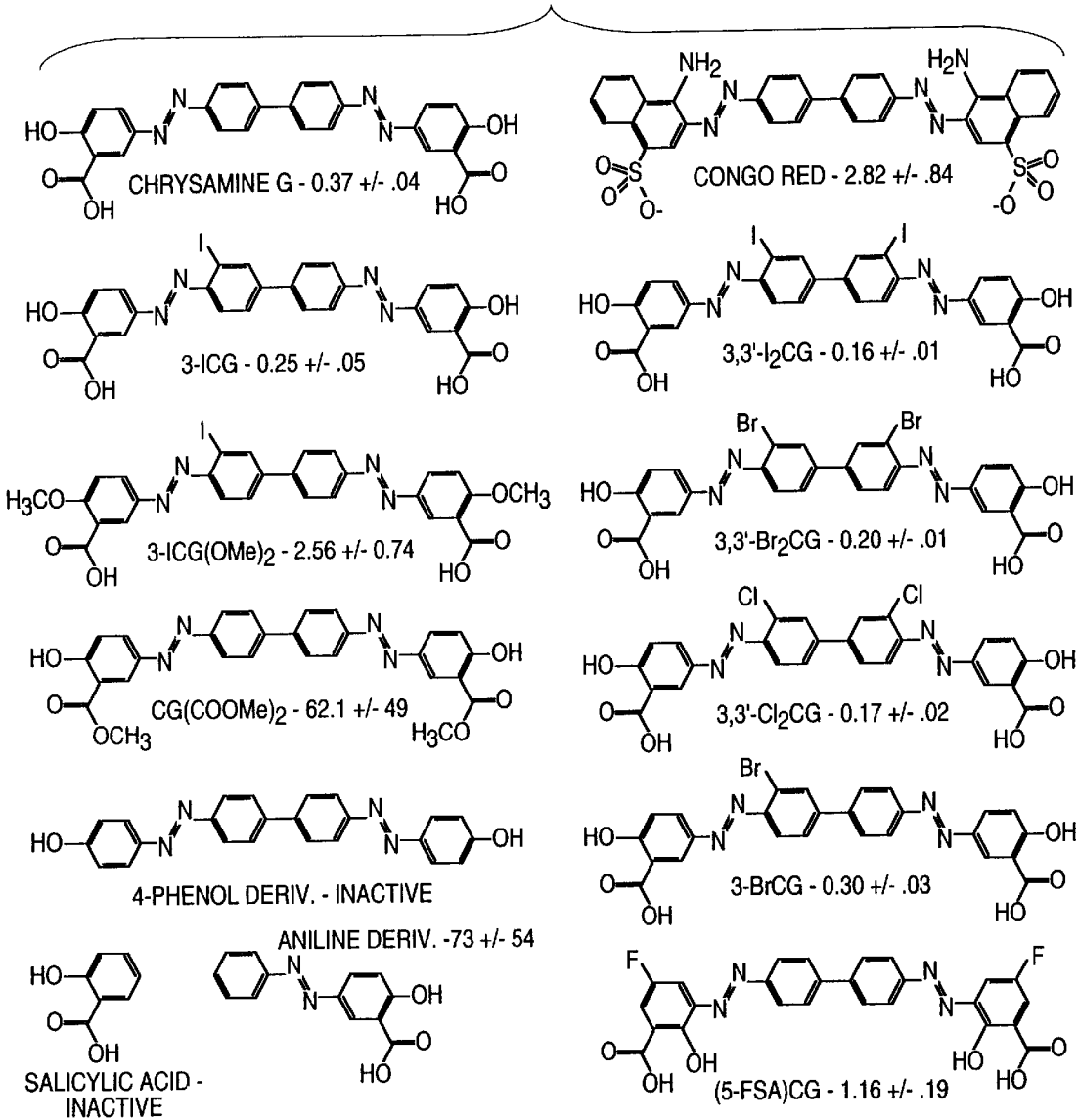
FIG. 1A illustrates the chemical structures of Chrysamine G and several Chrysamine G analogues or derivatives which have been synthesized and tested, including the 3-iodo derivative (3-ICG), the 3-iodo dimethoxy derivative (3-ICG (OMe)$_2$), the dimethyl ester derivative (CG(COOMe)$_2$), the phenol derivative, salicylic acid (SA), the aniline derivative (1/2 CG), Congo red, the 3,3'-diiodo derivative (3,3'-I$_2$CG), the 3,3'-dibromo derivative (3,3'-Br$_2$CG), the 3,3'-dichloro derivative (3,3'-Cl$_2$CG), the 3-bromo derivative (3-BrCG), and the 5-fluorosalicylic acid derivative ((5-FSA)CG). The numbers in the figure refer to each compound's $K_i$ (in μM) for inhibition of [$^{14}C$] Chrysamine G binding to the synthetic peptide, Aβ (10–43).
Figure 1B:
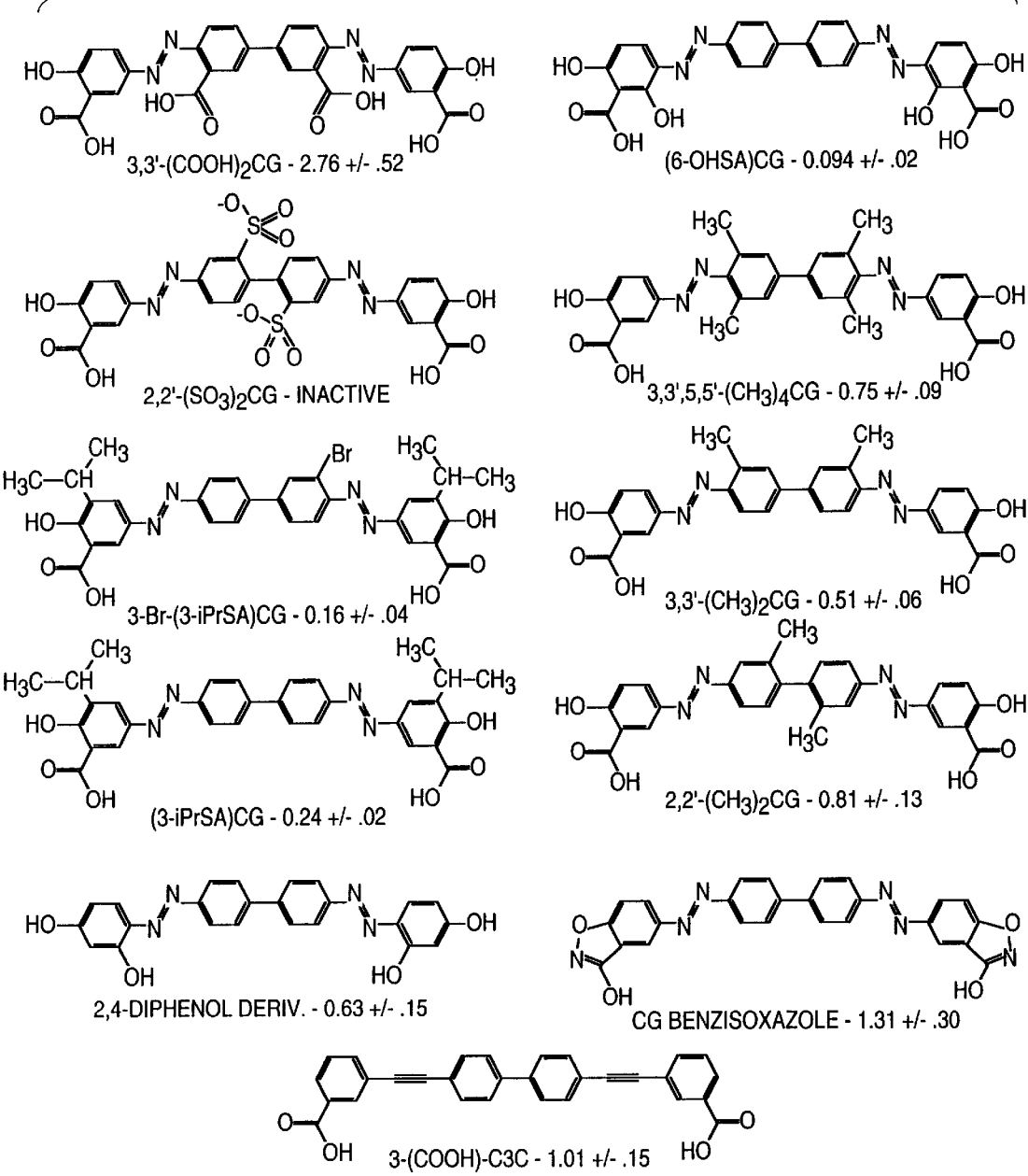
FIG. 1B illustrates the chemical structures of several Chrysamine G analogues or derivatives which have been synthesized and tested, including the 3,3'-dicarboxylic acid derivative (3,3'-(COOH)$_2$CG), the 2,2'-disulfonic acid derivative of Chrysamine G (2,2'-(SO$_3$)$_2$CG), the 3-bromo, 3-isopropylsalicylic acid derivative (3-Br-(3-iPrSA)CG), the 3-isopropylsalicylic acid derivative ((3-iPrSA)CG), the 2,4-diphenol derivative (2,4-Diphenol), the γ-resorcylic acid derivative ((6-OHSA)CG), the 3,3',5,5'-tetramethylbenzidine derivative (3,3',5,5'-(CH$_3$)$_4$CG), the 3,3'-dimethyl derivative (3,3'-(CH$_3$)$_2$CG), the 2,2'-dimethyl derivative(2,2'-(CH$_3$)$_2$CG), the benzisoxazole derivative (CG Benzisoxazole), and the 3-carboxy alkyne derivative (3-(COOH)-C3C). The numbers in the figure refer to each compound's $K_i$ (in μM) for inhibition of [$^{14}C$] Chrysamine G binding to the synthetic peptide, Aβ (10–43).

The present invention exploits the ability of alkyl, alkenyl and alkynyl Chrysamine G derivatives and radiolabeled derivatives thereof to cross the blood brain barrier in vivo and bind to Aβ deposited in plaques, to Aβ deposited in cerebrovascular amyloid, and to the amyloid consisting of the protein deposited in NFT. Chrysamine G is a Congo red derivative with the key structural difference being that the sulfonic acid moieties found in Congo red are replaced by carboxylic acid groups in Chrysamine G (FIG. 1). This structural alteration allows Chrysamine G to enter the brain better than Congo red and large macromolecules such as antibodies. Tubis et al., J. Am. Pharmaceut. Assn. 49: 422 (1960). Also, Chrysamine G may be a more specific marker for AD pathophysiology than antibodies, which would also label non-fibrillar Aβ deposits of uncertain pathological significance.

The alkyl, alkenyl and alkynyl Chrysamine G derivatives of the present invention have each of the following characteristics: (1) specific binding to synthetic Aβ in vitro, (2) binding to β-sheet fibril deposits in brain sections (3) ability to cross a non-compromised blood brain barrier in vivo.

The method of this invention determines the presence and location of amyloid deposits in an organ or body area, preferably brain, of a patient. The present method comprises administration of a detectable quantity of a pharmaceutical composition containing a compound of Formula I, as defined above, called a "detectable compound," or a pharmaceutically acceptable water-soluble salt thereof, to a patient. A "detectable quantity" means that the amount of the detectable compound that is administered is sufficient to enable detection of binding of the compound to amyloid. An "imaging effective quantity" means that the amount of the detectable compound that is administered is sufficient to enable imaging of binding of the compound to amyloid.

The invention employs amyloid probes which, in conjunction with non-invasive neuroimaging techniques such as magnetic resonance spectroscopy (MRS) or imaging (MRI), or gamma imaging such as positron emission tomography (PET) or single-photon emission computed tomography (SPECT), are used to quantify amyloid deposition in vivo. The term "in vivo imaging" refers to any method which permits the detection of a labeled compound of Formula I, as described above, of the present invention. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. A "subject" is a mammal, preferably a human, and most preferably a human suspected of having dementia.

For purposes of in vivo imaging, the type of detection instrument available is a major factor in selecting a given label. For instance, radioactive isotopes and $^{19}F$ are particularly suitable for in vivo imaging in the methods of the present invention. The type of instrument used will guide the selection of the radionuclide or stable isotope. For instance, the radionuclide chosen must have a type of decay detectable by a given type of instrument. Another consideration relates to the half-life of the radionuclide. The half-life should be long enough so that it is still detectable at the time of maximum uptake by the target, but short enough so that the host does not sustain deleterious radiation. The radiolabeled compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140–200 keV range. For PET detection, the radiolabel will be a positron-emitting radionuclide such as $^{19}F$ which will annihilate to form two 511 keV gamma rays which will be detected by the PET camera.

In the present invention, amyloid binding compounds/probes are made which are useful for in vivo imaging and quantification of amyloid deposition. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the alkyl, alkenyl and alkynyl Chrysamine G derivatives may be labeled with $^{19}F$ or $^{13}C$ for MRS/MRI by general organic chemistry techniques known to the art. See, e.g., March, J. "ADVANCED ORGANIC CHEMISTRY: REACTIONS, MECHANISMS, AND STRUCTURE (3rd Edition, 1985), the contents of which are hereby incorporated by reference. The alkyl, alkenyl and alkynyl Chrysamine G derivatives also may be radiolabeled with $^{18}F$, $^{11}C$, $^{75}Br$, or $^{76}Br$ for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391–450 (Raven Press, NY 1986) the contents of which are hereby incorporated by reference. The alkyl, alkenyl and alkynyl Chrysamine G derivatives also may be radiolabeled with $^{123}I$ for SPECT by any of several techniques known to the art. See, e.g., Kulkarni, Int. J. Rad. Appl. & Inst. (Part B) 18: 647 (1991), the contents of which are hereby incorporated by reference. In addition, the alkyl, alkenyl and alkynyl Chrysamine G derivatives may be labeled with any suitable radioactive iodine isotope, such as, but not limited to $^{131}I$, $^{125}I$, or $^{123}I$, by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art. See, Satyamurthy and Barrio J. Org. Chem. 48: 4394 (1983), Goodman et al., J. Org. Chem. 49: 2322 (1984), and Mathis et al., J. Labell. Comp. and Radiopharm. 1994: 905; Chumpradit et al., J. Med. Chem. 34: 877 (1991); Zhuang et al., J. Med. Chem. 37: 1406 (1994); Chumpradit et al., J. Med. Chem. 37: 4245 (1994). For example, a stable triazene or tri-alkyl tin derivative of alkyl, alkenyl and alkynyl Chrysamine G derivatives is reacted with a halogenating agent containing $^{131}I$, $^{125}I$, $^{123}I$, $^{76}Br$, $^{75}Br$, $^{18}F$ or $^{19}F$. Thus, the stable triazene and tri-alkyl tin derivatives of Chrysamine G and its analogues are novel precursors useful for the synthesis of many of the radiolabeled compounds within the present invention. As such, these triazene and tri-alkyl tin derivatives are one embodiment of this invention.

The alkyl, alkenyl and alkynyl Chrysamine G derivatives also may be radiolabeled with known metal radiolabels, such as Technetium-99m ($^{99m}$Tc). Modification of the substituents to introduce ligands that bind such metal ions can be effected without undue experimentation by one of ordinary skill in the radiolabeling art. The metal radiolabeled alkyl, alkenyl and alkynyl Chrysamine G derivative can then be used to detect amyloid deposits.

The methods of the present invention may use isotopes detectable by nuclear magnetic resonance spectroscopy for purposes of in vivo imaging and spectroscopy. Elements particularly useful in magnetic resonance spectroscopy include $^{19}$F and $^{13}$C.

Suitable radioisotopes for purposes of this invention include beta-emitters, gamma-emitters, positron-emitters, and x-ray emitters. These radioisotopes include $^{131}$I, $^{123}$I, $^{18}$F, $^{11}$C, $^{75}$Br, and $^{76}$Br. Suitable stable isotopes for use in Magnetic Resonance Imaging (MRI) or Spectroscopy (MRS), according to this invention, include $^{19}$F and $^{13}$C. Suitable radioisotopes for in vitro quantification of amyloid in homogenates of biopsy or post-mortem tissue include $^{125}$I, $^{14}$C, and $^{3}$H. The preferred radiolabels are $^{18}$F for use in PET in vivo imaging, $^{123}$I for use in SPECT imaging, $^{19}$F for MRS/MRI, and $^{3}$H or $^{14}$C for in vitro studies. However, any conventional method for visualizing diagnostic probes can be utilized in accordance with this invention.

The method could be used to diagnose AD in mild or clinically confusing cases. This technique would also allow longitudinal studies of amyloid deposition in human populations at high risk for amyloid deposition such as Down's syndrome, familial AD, and homozygotes for the apolipoprotein E4 allele. Corder et al., *Science* 261: 921 (1993). A method that allows the temporal sequence of amyloid deposition to be followed can determine if deposition occurs long before dementia begins or if deposition is unrelated to dementia. This method can be used to monitor the effectiveness of therapies targeted at preventing amyloid deposition.

Generally, the dosage of the detectably labeled alkyl, alkenyl and alkynyl Chrysamine G derivative will vary depending on considerations such as age, condition, sex, and extent of disease in the patient, contraindications, if any, concomitant therapies and other variables, to be adjusted by a physician skilled in the art. Dosage can vary from 0.001 mg/kg to 1000 mg/kg, preferably 0.1 mg/kg to 100 mg/kg.

Administration to the subject may be local or systemic and accomplished intravenously, intraarterially, intrathecally (via the spinal fluid) or the like. Administration may also be intradermal or intracavitary, depending upon the body site under examination. After a sufficient time has elapsed for the compound to bind with the amyloid, for example 30 minutes to 48 hours, the area of the subject under investigation is examined by routine imaging techniques such as MRS/MRI, SPECT, planar scintillation imaging, PET, and emerging imaging techniques, as well. The exact protocol will necessarily vary depending upon factors specific to the patient, as noted above, and depending upon the body site under examination, method of administration and type of label used; the determination of specific procedures would be routine to the skilled artisan. For brain imaging, preferably, the amount (total or specific binding) of the bound radioactively labelled Chrysamine G or Chrysamine G derivative or analogue is measured and compared (as a ratio) with the amount of labelled Chrysamine G or Chrysamine G derivative bound to the cerebellum of the patient. This ratio is then compared to the same ratio in age-matched normal brain.

The pharmaceutical compositions of the present invention are advantageously administered in the form of injectable compositions. A typical composition for such purpose comprises a pharmaceutically acceptable carrier. For instance, the composition may contain about 10 mg of human serum albumin and from about 0.5 to 500 micrograms of the labeled alkyl, alkenyl and alkynyl Chrysamine G derivative per milliliter of phosphate buffer containing NaCl. Other pharmaceutically acceptable carriers include aqueous solutions, non-toxic excipients, including salts, preservatives, buffers and the like, as described, for instance, in REMINGTON'S PHARMACEUTICAL SCIENCES, 15th Ed. Easton: Mack Publishing Co. pp. 1405–1412 and 1461–1487 (1975) and THE NATIONAL FORMULARY XIV., 14th Ed. Washington: American Pharmaceutical Association (1975), the contents of which are hereby incorporated by reference.

Examples of non-aqueous solvents are propylene glycol, polyethylene glycol, vegetable oil and injectable organic esters such as ethyl oleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the pharmaceutical composition are adjusted according to routine skills in the art. See, Goodman and Gilman's THE PHARMACOLOGICAL BASIS FOR THERAPEUTICS (7th Ed.).

Particularly preferred pharmaceutical compositions of the present invention are those that, in addition to specifically binding amyloid in vivo and capable of crossing the blood brain barrier, are also non-toxic at appropriate dosage levels and have a satisfactory duration of effect.

Molecular Modeling

Molecular modeling was done on an Evans and Sutherland PS-330 computer graphics system, running the computer modeling program MacroModel (Version 2.5 available from C. Still at Columbia University) to generate the Aβ peptide chains in the anti-parallel beta-sheet conformation. Kirschner et al., *Proc. Natl. Acad. Sci. U.S.A.* 83: 503 (1986). The amyloid peptides were used without further structural refinement. The Aβ peptides were aligned so that alternate chains were spaced 4.76 Å apart, characteristic of beta-sheet fibrils. Kirschner, supra. Chrysamine G was energy minimized and aligned with the fibril model to maximize contact with lysine-16 of Aβ(10–43) and the hydrophobic phenylalanine-19 and -20 region.

Characterization of Specific Binding to Aβ Synthetic Peptide: Affinity, Kinetics, Maximum Binding The characteristics of Chrysamine G and Chrysamine G derivative binding is first analyzed using synthetic Aβ peptide called Aβ(10–43). The 10–43 peptide was chosen because it has been shown that this peptide provides a model system containing all of the characteristic structural features of Aβ peptides. Hilbich et al., *J. Mol. Biol.* 218: 149 (1991). The 10–43 amino acid fragment of Aβ was synthesized with 9-fluorenylmethyl chloroformate (FMOC) chemistry by the Peptide Synthesis Facility of the University of Pittsburgh. The peptide was characterized by mass spectrometry and the major component had an $M_R$ of 3600 g/mole (calc. 3598). The peptide was further purified by the method of Hilbich et al. which, in brief, consisted of sequential size-exclusion chromatography on a Biogel P10 column (2×180 cm, 200–400 mesh, Biorad, Richmond, Calif.) in 70% formic acid followed by a second elution through a Biogel P4 column (2×180 cm, 200–400 mesh) in 1M acetic acid. Hilbich et al., *J. Mol. Biol.* 218: 149 (1991). The peptide was lyophilized and stored at −80° C. until used in the binding assays.

Amino acid sequence for Aβ(10–43) is as follows:

| 10  | 11  | 12  | 13  | 14  | 15  | 16  | 17  | 18  | 19  | 20  | 21  |
|-----|-----|-----|-----|-----|-----|-----|-----|-----|-----|-----|-----|
| Tyr | Glu | Val | His | His | Gln | Lys | Leu | Val | Phe | Phe | Ala |
| 22  | 23  | 24  | 25  | 26  | 27  | 28  | 29  | 30  | 31  | 32  | 33  |
| Glu | Asp | Val | Gly | Ser | Asn | Lys | Gly | Ala | Ile | Ile | Gly |
| 34  | 35  | 36  | 37  | 38  | 39  | 40  | 41  | 42  | 43  |     |     |
| Leu | Met | Val | Gly | Gly | Val | Val | Ile | Ala | Thr |     |     |

Binding Assay to Synthetic Aβ(10–43)

Binding assays were performed in 12×75 mm borosilicate glass tubes. Various concentrations of nonradioactive Chrysamine G derivatives were added in 10% ethanol/water. Ethanol was necessary to prevent the micelle formation which occurs with these diazo dye derivatives, since the micelles are trapped by the filter even in the absence of peptide. To the above solution, 25 μl of a 0.36 mg/ml suspension of Aβ(10–43) in $H_2O$ was added and 10% ethanol was added to bring the volume to 950 μl. After incubating for 10 min at room temperature, 50 μl of [$^{14}$C] Chrysamine G in 40% ethanol was added, resulting in a final concentration of [$^{14}$C]Chrysamine G of 100–125 nM depending on the preparation of [$^{14}$C]Chrysamine G used. The binding mixture was incubated for 30 min at room temperature. Bound and free radioactivity were separated by vacuum filtration through Whatman GF/B filters using a Brandel M-24R Cell Harvester (Gaithersburg, Md.) followed by two 3-ml washes with 10% ethanol at room temperature. Filters were equilibrated overnight in 4 ml Cytoscint®-ES scintillant (ICN Biomedicals, Inc., Irvine, Calif.) in 7.0 ml plastic scintillation vials before counting. In this and all binding assays, incubations were done at least in triplicate and the results expressed as mean ±standard deviation.

Kinetic Studies

Kinetics studies of [$^{14}$C]Chrysamine G binding to Aβ(10–43) were performed in 13×100 mm borosilicate glass tubes by the filtration assay described above. For the kinetics of association, 25 μl of 0.36 mg/ml Aβ(10–43) were placed in 475 μl of 10% ethanol and 4.5 ml of 125 nM [$^{14}$C] Chrysamine G was added to the solution at time zero. The mixture was rapidly vortexed and the binding reaction was stopped by vacuum filtration through Whatman GF/B filters using a Brandel M-24R Cell Harvester (Gaithersburg, Md.) followed by two 3-ml washes with 10% ethanol at room temperature at times of 5, 10, 20, 30, 45, 60, 75, 135, 240, and 300 sec.; bound radioactivity was determined as above.

For the kinetics of dissociation, 25 μl of 0.36 mg/ml Aβ(10–43) were placed in 450 μl of 10% ethanol followed by 25 μl of 2.5 μM [$^{14}$C]Chrysamine G in 40% ethanol. This mixture was vortexed and incubated for 30 min at room temperature. The mixture was diluted with 4.5 ml of 10 μM nonradioactive Chrysamine G in 10% ethanol at time zero, the mixture was rapidly vortexed, and the dissociation was stopped by filtration as above at times of 0.5, 1.5, 3, 5, and 15 min, and bound radioactivity was determined as above.

Characterization of Specific Binding to Alzheimer's Disease Brain

Binding of Chrysamine G to AD and Control Brain Homogenates

Autopsy brain samples were obtained from the Neuropathology Core of the Alzheimer's Disease Research Center of the University of Pittsburgh. Controls were defined as not meeting neuropathological criteria for AD (sufficient number of NPs or NFTs) according to the standards specified in a published NIA conference report. Khachaturian, *Arch. Neurol.* 42: 1097 (1985). Brain samples from eight control (ages 58–75), eleven AD (ages 61–84), and two Down syndrome brains (ages 23 and 51) were studied. There were six high-plaque (>20 NPs/×200 magnification) and five low-plaque (<20 NPs/×200 magnification) AD brains. Two controls were clinically demented but had no NPs or NFTs and received the diagnosis of "Dementia Lacking Distinctive Histology". Knopman *Dementia* 4: 132 (1993). Another control had dementia and olivopontocerebellar atrophy. The other controls had no clinical or histological evidence of neurologic disease. Autopsy samples were immediately frozen at −70° C. and stored at that temperature until homogenized. The numbers of NPs and NFTs were counted in sections of five separate but adjacent fields (×200 magnification) between cortical layers 2 and 4 in the cortex at the junction of superior and middle frontal gyri and superior temporal isocortex of all brains studied. A qualitative assessment of the presence of amyloid angiopathy in the superior/middle frontal cortex was made. The Bielschowsky silver impregnation method was used to identify NPs and NFTs and Congo red staining was used to identify cerebral amyloid angiopathy. Details of this procedure have been previously published. Moossy et al., *Arch. Neurol.* 45: 251 (1988). Samples used for CG binding to the superior/middle frontal or superior temporal cortex were adjacent on gross dissection to those used for NP and NFT counts.

Approximately 100 mg of tissue from the junction of the superior and middle frontal cortex, superior temporal cortex, frontal pole, head of the caudate, inferior parietal cortex, occipital cortex, or cerebellum were homogenized with a Polytron® tissue homogenizer (PT 10/35, Brinkman Instruments Inc., Westbury, N.Y.) for 30 sec at setting 6 in 10% ethanol at a concentration of 10–20 mg brain/ml. Not all areas were available from each brain. Aliquots of 25–150 μl tissue (about 25–300 μg of protein by the method of Lowry et al., *J. Biol, Chem.* 193: 265 (1951)) were incubated in 12×75 mm borosilicate glass tubes at room temperature with 10–750 nM [$^{14}$C]CG (26.8 Ci/mole) in a final volume of 1.0 ml of 10% ethanol for 30 min at room temperature. The standard conditions employed about 150 μg of protein and 75 nM [$^{14}$C]CG for the cerebellar ratio studies and about 75 μg of protein and 150 nM [$^{14}$C]CG for the correlative studies with NPs, NFTs, and amyloid angiopathy. Ethanol was necessary to prevent the micelle formation which occurs with diazo dye derivatives, since the micelles are trapped by the filter even in the absence of tissue. Bound and free radioactivity were separated by vacuum filtration through Whatman GF/B filters using a Brandel M-24R Cell Harvester (Gaithersburg, Md.) followed by two 3-ml washes with 10% ethanol at room temperature. Filters were equilibrated overnight in 4 ml Cytoscint®-ES scintillant (ICN Biomedicals, Inc., Irvine, Calif.) in 7.0 ml plastic scintillation vials before counting. Saturable (specific) binding was defined as total binding minus residual (non-saturable) binding in the presence of 20 μM unlabelled CG. In all binding assays, incubations were done at least in triplicate and the results expressed as mean ±standard error unless otherwise specified. Results were expressed either in absolute terms of fmol [$^{14}$C]CG bound/μg protein in a given brain area, or as a ratio of the fmol/μg protein in that brain area to the fmol/μg protein in the cerebellum of the same brain.

Octanol/Water Partitioning

Approximately 75 μM solutions of Chrysamine G or its analogues were prepared in 5.0 ml 1-octanol. Five ml of phosphate buffered saline (0.15 M NaCl, 5 mM potassium phosphate, pH 7.4) were added and the layers mixed by rapid vortexing. The mixture was then centrifuged at 1,000 g to facilitate the formation of two clear phases. The layers were separated using a separatory funnel and 600 μl of each layer was diluted with 400 μl of ethanol and the absorbance measured at 389 nm for Chrysamine G or the $\lambda_{max}$ for each analogue. Concentrations were determined after correction for the molar absorptivity differences in the two solvents and the partition coefficient expressed as the concentration in the octanol layer divided by the concentration in the aqueous layer. Experiments were done in triplicate.

Imaging the Binding of Chrysamine G to Amyloid Deposits in Alzheimer's Disease Brain For visual demonstration of CG derivative binding to tissue, 8 micron paraffin sections of an AD brain with heavy deposits of cerebrovascular amyloid were stained with 1,4-bis(3-carboxy-4-hydroxyphenylethenyl)-benzene by a modification of the method of Stokes and Trickey, *J. Clin. Pathol.* 26: 241–242 (1973) with 1 mM 1,4-bis(3-carboxy-4-hydroxyphenylethenyl)-benzene substituted for Congo red, but the procedure was otherwise identical. Stained slides were examined using fluorescence microscopy.

Determining Compound's Ability to Cross the Blood Brain Barrier

Mouse studies

Female Swiss-Webster mice were injected in the lateral tail vein with approximately 0.03 μCi/g of [$^{14}$C]Chrysamine G in a 0.9% NaCl solution. Mice were sacrificed by cervical dislocation at intervals of 15 min, 35 min, 1 hr, 4 hr, and 24 hr after injection. The carotid blood, brain, liver, and kidneys were rapidly obtained, weighed, and homogenized in distilled/deionized H$_2$O using a ground glass homogenizer. An aliquot was weighed into an 18.0 ml plastic scintillation vial (Beckman Poly-Q-Vial) and counted after addition of 10.0 ml of scintillation cocktail (Cytoscint®-ES (ICN)) and overnight equilibration. The [$^{14}$C]Chrysamine G content of the tissues was expressed as cpm/mg tissue.

Experiments in which radioactivity was extracted from tissues were performed as above except 0.05 μCi/g of [$^{14}$C]Chrysamine G was injected and the mice were sacrificed at 60 min. Brain and liver were then removed and extracted with a Folch procedure. Folch et al., *J. Biol. Chem.* 226: 447 (1957). In both tissues, over 95% of the extracted radioactivity was contained in the organic layer. The organic layer was evaporated to dryness, resuspended in a minimal amount of 10% methanol/90% ACN, and injected onto a silica column (Prep Nova Pak HR Silica, 7.8×300 mm, Waters, Milford, Mass.) and eluted isocratically with the same solvent. Under these conditions, 99% of the radioactivity is eluted in the solvent front, but most lipids are retained longer, making the fraction eluting in the solvent front suitable for injection onto the reverse-phase C4 column system described above. The entire solvent front was collected, dried, and resuspended in 10% ACN/90% sodium phosphate buffer (5 mM, pH 6) and injected, along with authentic non-radioactive Chrysamine G, onto the C4 column. One minute fractions were collected and counted after addition of 10 ml of Cytoscint®-ES.

In yet another embodiment, the invention relates to a pharmaceutical composition and method for preventing cell degeneration and toxicity associated with fibril formation in certain "amyloidosis associated" conditions such as Alzheimer's Disease, Down's Syndrome and Type 2 diabetes mellitus, hereditary cerebral hemorrhage amyloidosis (Dutch), amyloid A (reactive), secondary amyloidosis, familial Mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish), familial amyloid cardiomyopathy (Danish), isolated cardiac amyloid, (systemic senile amyloidosises), AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-I (familial amyloidotic polyneuropathy-Iowa), AApo-A-II (accelerated senescence in mice), fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele. This method involves administering a pharmaceutical composition comprising Chrysamine G, or one of the above described derivatives thereof, to a subject suspected of having or at high risk of developing such amyloidosis associated condition.

Because certain diazo compounds could be carcinogenic, the therapeutic compounds of the present invention include only non-toxic, non-carcinogenic compounds. That is, the present invention addresses the problems with potential carcinogenicity by using only alkyl, alkenyl and alkynyl compounds which do not contain groups that could be metabolized to carcinogenic benzidine compounds.

Any potential problems with lower bioavailability also is avoided by the use of alkyl, alkenyl and alkynyl derivatives of the azo compounds. These compounds are not substrates for reduction by bacterial or mammalian azo reductases.

Indeed, compounds of the present invention intended for therapeutic use are advantageous over existing compounds because they contain an 1,4-bis(3-carboxy-4-hydroxyphenylethenyl)-benzene linkage which is not a substrate for bacterial azo-reductases in the intestines.

In vitro studies have shown that Aβ neurotoxicity requires fibril formation and is inhibited by Congo red. Specifically, it has been shown that the amyloid fibril-binding dye Congo red inhibits fibrillar Aβ neurotoxicity by inhibiting fibril formation or by binding preformed fibrils. Lorenzo et al., *Proc. Natl. Acad. Sci. USA* 91: 12243–12247 (1994). Congo red also has been shown to inhibit pancreatic islet cell toxicity of diabetes-associated amylin, another type of amyloid fibril. Lorenzo et al., supra. See also, Burgevin et al. *NeuroReport* 5: 2429 (1994); Pollack et al., *J. Neurosci. Letters* 184: 113–116 (1995); Pollack et al. *Neuroscience Letters* 197: 211 (1995). These data indicate that amyloid-binding compounds such as alkyl, alkenyl and alkynyl derivatives of Chrysamine G, which are similar to Congo red but which, unlike Congo red, enter the brain well, would be effective in preventing cell degeneration and toxicity associated with fibril formation in amyloidosis associated conditions.

In Example 8 and FIGS. 12 and 13, it is shown that Chrysamine G has effects very similar to those previously reported for Congo red in having a dose-dependent, protective effect in rat pheochromocytoma. Therefore, these in vitro assays provide a means for selecting compounds for use in pharmaceutical compositions for the prevention of cell degeneration and toxicity associated with fibril formation.

Compounds such as Chrysamine G and the above described derivatives thereof, are tested pursuant to the present invention, for in vivo efficacy in preventing amyloid fibril formation or associated cellular degeneration, as measured by the formation of dystrophic neurites, synapse loss, neurofibrillary tangle formation and gliosis, in an animal model, such as the "senile animal" model for cerebral amyloidosis, Wisniewski et al., *J. Neuropathol. & Exp. Neurol.* 32: 566 (1973), the mouse model of familial Mediterranean fever (Neurochem., Inc. Kingston, Ontario, Canada) and the transgenic mouse model of Alzheimer-type neuropathology, Games et al., *Nature* 373: 523–527 (1995); Hsiao et al. *Science* 274: 99–102 (1996). In the familial Mediterranean fever model, the animals develop systemic amyloidosis. In an in vivo assay according to this invention, serial necropsies in animals treated and untreated with the compounds of the present invention to evaluate the inhibition of amyloid formation are compared. In the animal models for cerebral amyloid formation, in addition to following amyloid formation serially, the presence of amyloid-associated neurodegeneration, as measured by the formation of dystrophic neurites, synapse loss, neurofibrillary tangle formation and gliosis, also is assessed in serial necropsies in animals treated and untreated with the compounds of the present invention.

According to the present invention, a pharmaceutical composition comprising Chrysamine G or derivatives thereof, is administered to subjects in whom amyloid or amyloid fibril formation, cell degeneration and toxicity are anticipated. In the preferred embodiment, such subject is a human and includes, for instance, those who are at risk of developing cerebral amyloid, including the elderly, nondemented population and patients having amyloidosis associated diseases and Type 2 diabetes mellitus. The term "preventing" is intended to include the amelioration of cell degeneration and toxicity associated with fibril formation. By "amelioration" is meant the prevention of more severe forms of cell degeneration and toxicity in patients already manifesting signs of toxicity, such as dementia.

The pharmaceutical composition for purposes of preventing cell degeneration and toxicity associated with fibril formation in amyloidosis associated diseases comprises Chrysamine G or a derivative thereof described above and a pharmaceutically acceptable carrier. In one embodiment, such pharmaceutical composition comprises serum albumin, Chrysamine G or Chrysamine G derivative and a phosphate buffer containing NaCl. Other pharmaceutically acceptable carriers include aqueous solutions, non-toxic excipients, including salts, preservatives, buffers and the like, as described, for instance, in REMINGTON'S PHARMACEUTICAL SCIENCES, 15th Ed., Easton: Mack Publishing Co., pp. 1405–1412 and 1461–1487 (1975) and THE NATIONAL FORMULARY XIV., 14th Ed. Washington: American Pharmaceutical Association (1975), and the UNITED STATES PHARMACOPEIA XVIII. 18th Ed. Washington: American Pharmaceutical Association (1995), the contents of which are hereby incorporated by reference.

Examples of non-aqueous solvents are propylene glycol, polyethylene glycol, vegetable oil and injectable organic esters such as ethyl oleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. See, Goodman and Gilman's THE PHARMACOLOGICAL BASIS FOR THERAPEUTICS (7th Ed.).

According to the invention, such pharmaceutical composition could be administered orally, in the form of a liquid or solid, or injected intravenously or intramuscularly, in the form of a suspension or solution. By the term "pharmaceutically effective amount" is meant an amount that prevents cell degeneration and toxicity associated with fibril formation. Such amount would necessarily vary depending upon the age, weight and condition of the patient and would be adjusted by those of ordinary skill in the art according to well-known protocols. In one embodiment, a dosage would be between 0.1 and 100 mg/kg per day, or divided into smaller dosages to be administered two to four times per day. Such a regimen would be continued on a daily basis for the life of the patient. Alternatively, the pharmaceutical composition could be administered intramuscularly in doses of 0.1 to 100 mg/kg every one to six weeks.

In yet another embodiment, the invention relates to a method of detecting amyloid deposits in biopsy or post-mortem tissue. The method involves incubating formalin-fixed tissue with a solution of a compound of Formula I, described above. Preferably, the solution is 25–100% ethanol, (with the remainder being water) saturated with the compound of Formula I. Upon incubation, the compound stains or labels the amyloid deposit in the tissue, and the stained or labelled deposit can be detected or visualized by any standard method. Such detection means include microscopic techniques such as bright-field, fluorescence, laser-confocal and cross-polarization microscopy.

In yet another embodiment, the invention relates to a method of quantifying the amount of amyloid in biopsy or post-mortem tissue. This method involves incubating a labelled alkyl, alkenyl and alkynyl derivative of Chrysamine G, preferably the compounds of Formula I, or a water-soluble, non-toxic salt thereof, with homogenate of biopsy or post-mortem tissue. The tissue is obtained and homogenized by methods well known in the art. The preferred label is a radiolabel, although other labels such as enzymes, chemiluminescent and immunofluorescent compounds are well known to skilled artisans. The preferred radiolabel is $^{125}$I, $^{14}$C or $^{3}$H, the preferred label substituent of Formula I is at least one of $R_1$–$R_7$, $R_{10}$–$R_{27}$. Tissue containing amyloid deposits will bind to the labeled alkyl, alkenyl and alkynyl derivatives of Chrysamine G. The bound tissue is then separated from the unbound tissue by any mechanism known to the skilled artisan, such as filtering. The bound tissue can then be quantified through any means known to the skilled artisan. See Example 3. The units of tissue-bound radiolabeled Chrysamine G derivative are then converted to units of micrograms of amyloid per 100 mg of tissue by comparison to a standard curve generated by incubating known amounts of amyloid with the radiolabeled Chrysamine G derivative.

In yet another embodiment, the invention relates to a method of distinguishing an Alzheimer's diseased brain from a normal brain involving obtaining tissue from (i) the cerebellum and (ii) another area of the same brain, other than the cerebellum, from normal subjects and from subjects suspected of having Alzheimer's disease. See Example 3. Such tissues are made into separate homogenates using methods well known to the skilled artisan, and then are incubated with a radiolabeled alkyl, alkenyl and alkynyl Chrysamine G derivative. The amount of tissue which binds to the radiolabeled alkyl, alkenyl and alkynyl Chrysamine G derivative is then calculated for each tissue type (e.g. cerebellum, non-cerebellum, normal, abnormal) and the ratio for the binding of non-cerebellum to cerebellum tissue is calculated for tissue from normal and for tissue from patients suspected of having Alzheimer's disease. These ratios are then compared. If the ratio from the brain suspected of having Alzheimer's disease is above 90% of the ratios obtained from normal brains, the diagnosis of Alzheimer's disease is made.

EXAMPLE 1

The Synthesis of Chrysamine G and Derivatives Thereof

Synthesis of Chrysamine G

The synthesis of Chrysamine G (i.e., 4,4'-bis(3-carboxy-4-hydroxyphenylazo)-biphenyl) requires the following reaction steps. These reaction steps will be referred to as the "Chrysamine G Synthesis" general procedure. Benzidine●2HCl (28.9 mg, 0.11 mmole, Sigma Chemical Company, St. Louis, Mo.) was added to 1.5 ml of 1:1 DMSO:distilled/deionized $H_2O$ in a 50 cc round bottom flask. Each of the reaction steps were carried out at 0° C. unless otherwise specified. Twenty-nine μl of concentrated HCl were added, resulting in a clear solution after stirring. To the benzidine solution, a solution of 15.5 mg (0.22 mmole) of $NaNO_2$ in 300 μl of 1:1 DMSO/$H_2O$ was added drop-wise, resulting in a pH of about 2–3. The reaction mixture was stirred for 45 min, and then to this tetra-azotized benzidine mixture was added drop-wise over a 10 min period to 24.8 mg (0.18 mmole) of methyl salicylate (Aldrich) dissolved in 2.0 ml of 100% DMSO containing 250 mg/ml $Na_2CO_3$ in suspension, keeping the pH about 10.5. The resulting mixture was stirred for 1 hr at 0° C., and then overnight at room temperature.

After this time, the pH was adjusted to about 7 and the mixture was extracted with three 50 ml portions of chloroform. The combined chloroform extracts were washed with three 50 ml portions of $H_2O$, and then taken to dryness yielding the dimethyl ester of Chrysamine G (i.e., 4,4'-bis (3-methoxycarbonyl-4-hydroxyphenylazo)-biphenyl), which was further purified by recrystallization from chloroform/hexane. The ester was then hydrolysed by dissolution in about 100 ml of 1:1 ethanol:$H_2O$ containing four equivalents of NaOH and refluxed for three hours. Evaporation of the ethanol followed by lyophilization of the $H_2O$ yielded the tetra-sodium salt of Chrysamine G. The free acid of Chrysamine G was formed by dissolving the tetra-sodium salt in $H_2O$, washing once with chloroform to remove any unhydrolysed dimethyl ester, lowering the pH to about 2 and extracting with three 50 ml portions of ethyl acetate. The combined ethyl acetate extracts were washed with three 50 ml portions of $H_2O$ and taken to dryness.

Under these conditions, there was no remaining methyl salicylate, salicylic acid, or benzidine, and only trace amounts of the mono-substituted product, 4-hydroxy-4'-(3-carboxy-4-hydroxyphenylazo)-biphenyl by reverse-phase HPLC using a C4 column (Vydac 214-TP510) using a solvent system of sodium phosphate buffer (5 mM, pH 6):acetonitrile (ACN) 90:10, isocratically, for 10 min and then increased to 50% ACN over the next 20 min at a flow rate of 3.5 ml/min. The column eluant was monitored at 290 and 365 nm with a dual wavelength, diode array detector (Perkin Elmer 235C). Under these conditions, Chrysamine G eluted at 17.6 min.

The structure of Chrysamine G and derivatives was confirmed by proton NMR at 500 MHz in DMSO-$d_6$ with TMS as the internal standard. The peak assignments for the tetra-sodium salt of Chrysamine G were as follows with SA referring to protons at the specified ring position on the salicylic acid moiety and BZ referring to protons on the benzidine moiety: SA-3, doublet J=8.73 Hz at 6.75 parts per million (ppm); SA-4, doublet of doublets J=8.73 and 2.72 Hz at 7.82 ppm; BZ-2/6, doublet J=8.44 Hz at 7.91 ppm; BZ-3/5, doublet J-8.44 Hz at 7.95 ppm; and SA-6, doublet J-2.72 Hz at 8.28 ppm. The UV/visible spectrum in 40% ethanol showed a $\lambda_{max}$ at 389 nm. The molar absorptivity of Chrysamine G was determined by calculating the concentration of Chrysamine G through comparison of peak areas to an internal standard by NMR and then immediately running the UV/vis spectrum of an aliquot of the NMR sample diluted in 40% ethanol. The molar absorptivity in 40% ethanol at 389 nm was $5.5\times10^4$ AU/(cm●M).

[$^{14}$C]Chrysamine G was synthesized by a modification of the above procedure. The tetra-azotization of benzidine was performed as described above except in 100% $H_2O$. Fifty μl of 2.5 M $Na_2CO_3$ in $H_2O$ were added to 50 μCi of crystalline salicylic acid-carboxy-$^{14}$C (Sigma) in a 0.5 ml conical glass vial. Sixty μl of the tetra-azotized benzidine mixture was added to the conical vial, vortexed and kept at 0° C. for 1 hr. To prevent formation of the mono-substituted benzidine by-product, 12.5 μl of 250 mM non-radioactive salicylic acid (Sigma) in 2.5 M $Na_2CO_3$ was added to the reaction mixture and maintained for 1 hr at 0° C. The vial was kept overnight at room temperature. The entire mixture was dissolved in a minimal amount of 35% ACN and injected onto the C4 column as described above. The peak corresponding to the Chrysamine G standard was collected and lyophilized. A specific activity of 26.8 Ci/mole was calculated by determining the absorbance at 389 nm and then counting the radioactivity in an aliquot of the same sample. The [$^{14}$C]Chrysamine G was stored in 40% ethanol. When the purified [$^{14}$C]Chrysamine G was re-injected onto the C4 column and eluted isocratically with 21% ACN at 3.5 ml/min, >98% of the radioactivity co-eluted with authentic Chrysamine G at 10.4 min. Many of the Chrysamine G derivatives were synthesized using this "Chrysamine G Synthesis" general procedure, with the exceptions noted below. Structures of the derivatives were verified by NMR. FIG. 1 shows the chemical structure of Chrysamine G and several derivatives.

Synthesis of Alkenyl (CH=CH) derivatives of Chrysamine-G 4,4'-biphenyldicarboxylic acid (Aldrich) is converted by reduction with LiAlH$_4$ to 4,4'-bis(hydroxymethyl)biphenyl, which, in turn, is converted to 4,4'-bis(iodomethyl)biphenyl by reaction with NaI and BF$_3$-etherate in ACN. The iodo compound is heated to 90° C. for one hour with excess triethyl phosphite to produce tetraethyl 4,4'-biphenyldimethylphosphonate. Similar treatment of 1,4-napthalene-dicarboxylic acid (Aldrich) or 9,10-anthracene-dicarboxylic acid (Aldrich) yields the respective tetraethyl phoshonates. After recrystallization from hexane, the phosphonate is dissolved in DMF and treated with a ten-fold excess of sodium methoxide, followed by two equivalents of 5-formylsalycylic acid in DMF. After stirring at room temperature for 24 hrs, the reaction mixture is poured into water. Acidification of the water to pH 5.0 with HCl causes precipitation of the flourescent product, 4,4'-bis(3-carboxy-4-hydroxyphenylethenyl)-biphenyl, which can be selectively extracted into ethyl acetate from any mono-substituted by-product. Similar treatment of tetraethyl p-xylenediphosphonate (TCI America) with 5-formylsalicylic acid, or its derivatives, gives 1,4-bis(3-carboxy-4-hydroxyphenylethenyl)-benzene. Likewise 1,4-bis(3-carboxy-4-hydroxyphenylethenyl)-naphthalene or 9,10-bis(3-carboxy-4-hydroxyphenylethenyl)-anthracene is obtained by treating the appropriate phosphonate with 5-formylsalicylic acid. Other derivative are obtained by the use of other formylsalicylic acid congeners, formyl benzoic acids, or hydroxy- or methoxybenzaldehydes.

When backbone linkers other than those listed above are desired, the appropriate dicarboxylic acid (such as 2-bromoterephthalic acid (Aldrich)) is reduced to the diol, converted to the iodide, and then to the tetraethyl diphosphonate as described above. When side groups other than salicylic acid are desired, the appropriate phenol (which will usually also contain an acidic functionality as well) is first iodinated ortho or para (depending on the presence of other substituents) to the phenol and then formylated at the iodo-position by standard methods.

Synthesis of Alkyl-Substituted Alkenyl (CR'=CR') derivatives of Chrysamine-G 4,4'-biphenyldicarboxylic acid (Aldrich) or 1,4-benzenedicarboxylic acid (Aldrich) is first converted by reduction with LiAlH$_4$ to the bis(hydroxymethyl) compound, which, in turn, is converted to the dicarboxaldehyde by treatment with BaMnO$_4$ in ethyl acetate. This dialdehyde is reacted with R'MgX (where R' is a lower alkyl group and X is Br or I) via the Grignard reaction to produce HOCR'H—Ph—Ph—CR'H—OH or HOCR'H—Ph—CR'H—OH. The alkyl-substituted bis(hydroxymethyl) compound is converted to the alkyl-substituted bis(iodomethyl) compound by reaction with NaI and BF$_3$-etherate in ACN. The iodo compound is heated to 90° C. for about one hour with excess triethyl phosphite to produce the alkyl-subsitiuted tetraethyl dimethylphosphonate. Similar treatment of 1,4-naphthalene-dicarboxylic acid (Aldrich) or 9,10-anthracene-dicarboxylic acid (Aldrich) yields the respective alkyl-substituted tetraethyl dimethylphosphonates.

Alkyl-substituted aklenyl compounds of three varieties, namely AR—CR'=CR'—Q, AR—CR'=CH—Q or Ar—CH=CR'—Q (where R' is a lower alkyl group and Q is as defined in Formula I), can then be synthesized. AR—CR'=CR'—Q compounds can be made by reacting an alkyl-substituted tetraethyl dimethylphosphonate with a suitable aryl ketone such as 5-acetylsalicyclic acid (Crescent Chemical Co., Inc., Hauppage N.Y.). AR—CR'=CH—Q compounds can be made by reacting an alkyl-substituted tetraethyl dimethylphosphonate with a suitable aldehyde such as 5-formylsalicyclic acid (Aldrich). AR—CH=CR'—Q compounds can be made by reacting tetraethyl dimethylphosphonate with a suitable aryl ketone such as 5-acetylsalicyclic acid (Crescent Chemical Co., Inc., Hauppage N.Y.). The reaction conditions are identical to those used to make the alkenyl (CH=CH) derivatives described above.

Synthesis of Alkynyl (C≡C) Derivatives of Chrysamine G

5-Iodosalicylic acid (Aldrich Chemical Company, Milwaukee, Wis.) is converted to the methyl ester by reaction with methanol, trimethyl orthoformate and sulfuric acid. The 5-iodosalicylic acid methyl ester thus obtained is reacted with (trimethylsilyl)acetylene (Aldrich Chemical Company, Milwaukee, Wis.) in the presence of palladium. The trimethylsilyl group is removed and two equivalents of the resultant 5-acetylenylsalicylic acid methyl ester is reacted with 4,4'-dibromobiphenyl (Aldrich Chemical Company, Milwaukee, Wis.) in the presence of palladium as above. The resultant alkynyl analogue of Chrysamine G, 4,4'-bis(3-methoxycarbonyl-4-hydroxyphenylacetylenyl)-biphenyl is prepared by hydrolysis of the ester as described above.

Alternative Synthesis of Alkynyl (C≡C) and Vinyl (CH=CH) Derivatives of Chrysamine G 5-Bromosalicylic acid (Aldrich Chemical Company, Milwaukee, Wis.) is converted to the methyl ester/methyl ether by reaction with methyl iodide in the presence of K$_2$CO$_3$, as described above. The 2-methoxy-5-bromobenzoic acid methyl ester thus obtained is reacted with (trimethylsilyl)acetylene (Aldrich Chemical Company, Milwaukee, Wis.) in the presence of palladium. The trimethylsilyl group is removed and two equivalents of the resultant 2-methoxy-5-acetylenylbenzoic acid methyl ester is reacted with 4,4'-dibromobiphenyl (Aldrich Chemical Company, Milwaukee, Wis.) in the presence of palladium as above. The resultant alkynyl analogue of Chrysamine G, 4,4'-bis(3-carboxy-4-methoxyphenylacetylenyl)-biphenyl is prepared by hydrolysis of the ester as described above. This alkynyl analogue is reduced by conventional methods to form the vinyl analogue of Chrysamine G.

Synthesis of Alkyl (CH$_2$—CH$_2$) Derivatives of Chrysamine G

Either the alkenyl or alkynl derivatives described above are hydrogenated by standard methods using hydrogen gas and a platinum or palladium catalyst.

Synthesis of Di-fluoro Alkenyl Chrysamine G Derivative

The 5-fluoro derivative, 1,4-bis(2-hydroxy-3-carboxy-5-fluorophenylethenyl)-benzene), is synthesized by substituting 3-formyl-5-fluorosalicylic acid for 5-formyl-salicylic acid. [$^{18}$F]aryl fluorides derivatives of Chrysamine G can be prepared by substituting $^{18}$F-labeled precursors such as [$^{18}$F]LiBF$_4$, in the Schiemann reaction, via triazene decomposition with Cs [$^{18}$F], or via nucleophilic $^{18}$F-for-X substitution, where X=tosyl, triflate, NO$_2$, $^+$N(CH$_3$)$_3$, or halogen. See Fowler, J. and Wolf, A. in POSITRON EMISSION TOMOGRAPHY AND AUTORADIOGRAPHY (Phelps, M., Mazziota, J., and Schelbert, H. eds.) 391–450 (Raven Press, NY, 1986) and Kilbourn, M. Fluorine-18 labeling of radiopharmaceuticals. (Natl. Acad. Press, Washington, D.C.) (1990).

Synthesis of Aromatic Fluoroalkyl and Fluoroalkoxy Derivatives

Aromatic fluoroalkyl derivatives are synthesized employing the method of Bishop et al., *J. Med. Chem.* 34: 1612 (1991) in which Claisen rearrangement of the appropriate O-allyl ethers forms an aromatic allyl derivative which can be further functionalized to yield the fluoroethyl or fluoropropyl derivatives. Alternatively, an aromatic iodide can be readily converted to an aromatic alkyne consisting of two to five carbon atoms in length using the palladium-assisted coupling methodology of Sonogashira et al., *Tetrahedron Letters* 4467–4470 (1975). Subsequent derivatization of the alkyne yields the fluoroalkyl derivative. Fluoroalkoxy derivatives may be prepared by the method of Chumpradit et al., *J. Med. Chem.* 36: 21 (1993) in which alkylation of the appropriate phenol with the appropriate 1-bromo (or iodo or sulfonyloxy)-omega-fluoroalkane yields the corresponding fluoroalkoxy derivative.

Radiofluorination of Aromatic Alkylsulfonyloxy and Alkoxysulfonyloxy Derivatives Radiofluorination to yield the aromatic [18F]fluoroalkyl and [$^8$F]fluoroalkoxy derivatives is performed by the method of Mathis et al., *Nucl. Med. Biol.* 19: 571 (1992) in which aromatic alkyl- or alkoxysulfonyloxy (e.g. alkoxytosylate) derivatives are substituted with [$^{18}$F]fluoride to yield aromatic [$^{18}$F]fluoralkyl and [$^{18}$F]fluoroalkoxy compounds.

Radio-Iodination and Radio-Bromination by the Tri-Alkyl Tin Route

Synthesis of Tri-Alkyl Tin Derivatives

The general structure of the alkenyl tri-alkyl tin derivative of Chrysamine G is shown in FIG. 2B. In general, one tri-alkyl tin group will be substituted at the 3-position on one side of the biphenyl moiety, but other positions, including the salicylic acid or heterocyclic moiety are also potential targets. These tri-alkyl tin derivatives are stable immediate precursors for preparation of the radioiodinated and radiobrominated compounds to be used in humans. More specifically, these tri-alkyl tin derivatives are used to prepare the halogenated radioactive compounds applicable for use in in vivo imaging of amyloid.

General Procedures for the Synthesis of Tri-Alkyl Tin Derivatives

Tri-alkyl tin derivatives are prepared from the appropriate arylhalides, [(C$_6$H$_5$)$_3$P]$_3$Pd(0), and hexaalkylditin by previously published procedures including Kosugi, M., et al., *Chem. Lett.* 1981: 829; Heck, R. *Pure and Appl. Chem.* 1978: 691; Echavarren, A. and Stille, J. *J. Am. Chem. Soc.* 1987: 5478; Mitchell, T. J. *Organometallic Chem.* 1986: 1; and Stille, J. *Pure and Applied Chem.* 1985: 1771. These derivatives also can be obtained by the use of n-BuLi and trialkyl tin chloride by the procedure of Mathis et al., *J. Labell. Comp. and Radiopharm.* 1994: 905.

Synthesis of the 3-trialkyl tin derivative of 4,4'-bis(3-methoxycarbonyl-4-hydroxyphenylazo)-biphenyl 3-Bromo or 3-iodo-4,4'-bis(3-methoxycarbonyl-4-hydroxyphenylazo)-biphenyl or its dimethyl ether are prepared by synthesis of 3-bromo- or 3-iodobenzidine (see above), tetra-azotization and coupling to methyl salicylate as for the synthesis of Chrysamine G, and methylation of the phenol as described above when the methoxy compound is desired. Under an argon atmosphere, 1 mmol of the phenolic ester or the methoxy ester, [(C$_6$H$_5$)$_3$P]$_3$Pd(0) (0.1 to 0.2 mmol), hexabutylditin or hexamethyl ditin (1.25 mmol), and dioxane (25 ml) is heated at 70° C. for 16 hrs. The reaction mixture is cooled and the solvent is evaporated. Tri-alkyl tin halide is removed with aqueous KF. The organics are extracted with ethyl acetate, dried over magnesium sulfate, filtered, and the solvent is evaporated under reduced pressure. The residue is purified on silica gel to obtain 3-trialkyltin-4,4'-bis(3-methoxycarbonyl-4-hydroxyphenylazo)-biphenyl.

Radio-Iodination or Radio-Bromination of Tri-Alkyl Tin Derivatives

The tributyl or trimethyl tin derivatives are radio-iodinated with Na[$^{125}$I] or Na[$^{123}$I] or radio-brominated with Na[$^{75}$Br] or Na[$^{76}$Br] by published procedures such as Mathis et al., *J. Labell. Comp. and Radiopharm.* 1994: 905; Chumpradit et al., *J. Med. Chem.* 34: 877 (1991); Zhuang et al., *J. Med. Chem.* 37: 1406 (1994); Chumpradit et al., *J. Med. Chem.* 37: 4245 (1994). In general, 0.5 mg of tri-alkyl tin compound, 0.2 ml of anhydrous acetonitrile, 10 μl of 2M H$_3$PO$_4$, 2–100 μl of a solution of high specific activity (>2000 Ci/mmol) Na[$^{125}$I] or Na[$^{123}$I] (or Na[$^{75}$Br] or Na[$^{76}$Br]) in pH 9–12 NaOH, and dichloramine-T (DCT) (20 μl of 2.5 mg/ml DCT in acetonitrile) are placed in a 1 ml Reacti-Vial. The vial is capped and the mixture is stirred at room temperature in the dark. The reaction is monitored by HPLC and after 30 min is quenched with 50 μl of 2 M Na$_2$S$_2$O$_3$. The product is purified by standard chromatographic techniques. Mathis et al., *J. Labell. Comp. and Radiopharm.* 1994: 905. Similarly, low specific activity $^{18}$F derivatives are prepared by analogous procedures.

General Procedures for the Preparation of Non-Radioactive I, Br, Cl, F and —SH Derivatives In general, 3- or 4-amino derivatives of 5-formylsalicylic acid, or the corresponding derivatives of the heterocyclic analogues of salicylic acid shown in FIG. 2, are converted to the corresponding diazo compounds with sodium nitrite and HCl or H$_2$SO$_4$. The iodine derivatives are directly prepared by forming the diazonium iodide which is then converted into the aryl iodide, or by way of the triazene intermediates. See, e.g., Greenbaum, F. *Am. J. Pharm.* 108: 17 (1936), Satyamurthy, N. and Barrio, J., *J. Org. Chem.* 48: 4394 (1983) and Goodman, M. et al., *J. Org. Chem.* 49: 2322 (1984). Aryl bromides and chlorides are prepared from the diazo compounds by treatment with CuCl or CuBr according to the Sandmeyer reaction or via the triazene as for the iodine derivatives. Aryl fluorides are prepared by treating the diazonium compounds with NaBF$_4$, HBF$_4$, or NH$_4$BF$_4$ according to the Schiemann reaction or via triazene decomposition similar to the iodine derivatives. Aryl thiols are prepared from the diazonium compounds by treatment with sulfur-containing nucleophiles such as HS$^-$, EtO—CSS$^-$, and S$_2^{2-}$. Alternatively, aryl thiols can be prepared by replacement of aryl halides with sulfur containing nucleophiles. These reactions are described in March, J., ADVANCED ORGANIC CHEMISTRY: REACTIONS, MECHANISMS, AND STRUCTURE (3rd Edition, 1985).

General Procedures for the Preparation of Radioactive C, F and Tc Derivatives In addition to the above procedures, high specific activity radiolabeling with $^{99m}$Tc for SPECT or with the positron-emitting radionuclides $^{11}$C, $^{18}$F, $^{75}$Br and $^{76}$Br is accomplished according to literature-based methods well known in the art. Some of the potential specific methods are described below, but there are other well-known methods which will be apparent to those skilled in the art and are described in Fowler, J. and Wolf, A. Positron emitter-labeled compounds in POSITRON EMISSION TOMOGRAPHY AND AUTORADIOGRAPHY (Phelps, M., Mazziota, J., and Schelbert, H. eds.) p 391–450 (Raven Press, NY) (1986), Coenen, H. et al., *Radiochimica Acta* 34: 47 (1983), and Kulkarni, *Int. J. Rad. Appl. & Inst.* (Part B) 18: 647 (1991), the contents of which are hereby incorporated by reference.

$^{99m}$Tc derivatives are prepared by complexation with the aryl thiols. Radiolabeling with $^{11}$C can be readily done via N-methylation, O-methylation as described above substituting [$^{11}$C]methyl iodide, [$^{11}$C]alkylation, or [$^{11}$C] carboxylation of suitable alkyl, alkenyl, or alkynyl Chrysamine G analogues. [$^{18}$F]aryl fluorides derivatives can be prepared by substituting $^{18}$F-labeled precursors such as [$^{18}$F]LiB$_4$ in the Schiemann reaction described above, via triazene decomposition with Cs[$^{18}$F], or via nucleophilic $^{18}$F-for-X substitution, where X=tosyl, triflate, NO$_2$, $^+$N(CH$_3$)$_3$, or halogen. Radiobromination using $^{75}$Br and $^{76}$Br can be accomplished using either electrophilic (Br$^+$) or nucleophilic (Br$^-$) substitution techniques analogue to radioiodination techniques, see Coenen, H., supra.

Synthesis of the 3-hydroxy-1,2-benzisoxazole derivative and related derivatives (see FIG. 2C)

2,6-Dihydroxybenzoic acid (γ-resorcylic acid) methyl ester (TCI America, Portland, Oreg.) is converted to the hydroxamic acid by the use of hydroxylamine hydrochloride according to the method of Böshagen (Chem. Ber 100: 954–960; 1967). The hydroxamic acid is converted to the corresponding 3-hydroxy-1,2-benzisoxazole with the use of SOCl$_2$ and then triethylamine, also by the method of Böshagen (Chem. Ber 100: 954–960; 1967). This compound is then converted to the formyl derivative and coupled to the appropriate tetraethyl diphosphonate (which in some cases may be brominated) as described above under the synthesis of alkenyl derivatives. The bromo derivatives can then converted to the tri-alkyl tin and iodo-derivatives as described above.

Alternatively, 5-formyl salicylic acid is coupled to the appropriate tetraethyl diphosphonate as usual and the resulting 4,4'-bis(3-methoxycarbonyl-4-hydroxyphenylethenyl)-benzene is converted first to the dimethyl ester and then to the hydroxamic acid and finally the benzisoxazole by the method of Böshagen as described above. A third type of 3-hydroxy-1,2-benzisoxazole is synthesized from several isomeric dihydroxy benzenedicarboxylic acids including 4,6-dihydroxy-1,3-benzenedicarboxylic acid, 3,6-dihydroxyphthalic acid, and 2,5-dihydroxyterephthalic acid (Aldrich Chem. Co., Milwaukee, Wis.). After formylation and coupling to the appropriate tetraethyl diphosphonate by standard procedures, followed by conversion to the dimethyl esters, the dihydroxy/diesters are converted to dihydroxy/dihydroxamic acids by reaction with hydroxylamine by the method of Böshagen described above. Conversion to the double benzisoxazole is effected by treatment with SOCl$_2$ and triethylamine, again, by the method of Böshagen described above.

Synthesis of the phthalimide or isoindole-1,3(2H)-dione derivative (see FIG. 2D)

3-Hydroxyphthalimide made from 3-hydroxyphthalic anhydride (Aldrich Chemical Company, Milwaukee, Wis.) is converted to the formyl derivative and coupled to the appropriate tetraethyl diphosphonate (which in some cases may be brominated) as described above under the synthesis of alkenyl derivatives. The bromo derivatives can then converted to the tri-alkyl tin and iodo-derivatives as described above.

Synthesis of the phthalhydrazide or 2,3-benzodiazine-1,4(2H,3H)-dione derivative (see FIG. 2E)

3-Hydroxyphthalhydrazide made from the reaction of 3-hydroxyphthalic anhydride (Aldrich Chemical Company, Milwaukee, Wis.) with hydrazine is converted to the formyl derivative and coupled to the appropriate tetraethyl diphosphonate (which in some cases may be brominated) as described above under the synthesis of alkenyl derivatives. The bromo derivatives can then converted to the tri-alkyl tin and iodo-derivatives as described above.

Synthesis of the 2,3-benzoxazine-1,4(3H)-dione derivative (see FIG. 2F)

3-Hydroxyphthalic anhydride (Aldrich Chemical Company, Milwaukee, Wis.) is converted to the 2,3-benzoxazine with the use of hydroxylamine. The benzoxazine derivative is then converted to the formyl derivative and coupled to the appropriate tetraethyl diphosphonate (which in some cases may be brominated) as described above under the synthesis of alkenyl derivatives. The bromo derivatives can then converted to the tri-alkyl tin and iodo-derivatives as described above.

Synthesis of the (2H)1,3-benzoxazine-2,4(3H)-dione derivative (see FIG. 2G)

This compound is synthesized by the method of Effenberger et al., (*Chem. Ber.* 105: 1926–1942; 1972). Briefly, 4-hydroxybenzaldehyde (Aldrich) is coupled with the appropriate tetraethyl diphosphonate via the same procedure used for formylsalicylic acid derivatives. This adduct is then converted to the carbamate by reaction with ethoxycarbonylisocyanate (O=C=N—CO—O—Et) in the presence of triethylamine. This substituted carbamate (or N-ethoxycarbonyl-carbamic acid-phenyl ester) is converted to the benzoxazinedione by heating in diphenyl ether. The benzoxazinedione is then converted to the tri-alkyl tin and iodo-derivatives, as described above.

Synthesis of the (3H)2-benzazine-1,3(2H)-dione derivative (see FIG. 2H)

3-Hydroxyphenylacetic acid (Aldrich Chemical Company, Milwaukee, Wis.) is formylated, converted to the amide and then coupled with the appropriate tetraethyl diphosphonate via the same procedure used for formylsalicylic acid derivatives. This adduct is then converted to the N-(3-hydroxyphenylacetoxy)-carbamic acid ethyl ester derivative by reaction with ethyl chloroformate. This substituted carbamate is converted to the benzazinedione by heating in diphenyl ether. The benzazinedione is then converted to the tri-alkyl tin and iodo-derivatives, as described above.

Synthesis of the 1,8-Naphthalimide derivative (See FIG. 2I)

4-Amino-1,8-naphthalimide is converted to the formyl derivative and coupled to the appropriate tetraethyl diphosphonate (which in some cases may be brominated) as described above under the synthesis of alkenyl derivatives. The bromo derivatives can then converted to the tri-alkyl tin and iodo-derivatives as described above.

Synthesis of Tetrazole and Oxadiazole Derivatives
(See FIGS. 2J and 2K)

2-Cyanophenol (Aldrich Chemical Company, Milwaukee, Wis.) is converted to the tetrazole by reaction with sodium or aluminum azide according to the method of Holland and Pereira *J. Med. Chem.* 10: 149 (1967) and Holland U.S. Pat. No. 3,448,107. Briefly, 2-cyanophenol or alkenyl cyanophenol derivatives of Chrysamine G (made by coupling 4-formyl-2-cyanophenol with the appropriate tetraethyl diphosphonate) (1 mmol) in 40 ml DMF is treated with sodium azide (10 mmol) and triethylamine hydrochloride (10 mmol) under argon. The mixture is stirred at 120° C. for 2 hrs after which the mixture is cooled and worked up in a manner analogous to that described above for Chrysamine G.

The oxadiazoles are synthesized by treatment of the tetrazoles prepared as above with an acid anhydride (such as acetic anhydride). An alternate method is that of Bamford et al., *J. Med. Chem.* 38: 3502 (1995). In this procedure, hydrazide alkenyl derivatives of Chrysamine G or salicylic acid (obtained by treatment of the respective esters with hydrazine) are treated with methyl isothiocyanate in the presence of dicyclohexylcarbodiimide.

Synthesis of Chrysamine G Derivatives for Use as Controls

The aniline derivative is synthesized by substituting two equivalents of aniline (Fisher Chemical Co., Fair Lawn, N.J.) for each equivalent of benzidine. The 2,2'-disulfonic acid derivative is synthesized by substituting benzidine-2, 2'-disulfonic acid (Pfaltz & Bauer, Inc., Waterbury, Conn.) for benzidine. The phenol derivative is synthesized by substituting one equivalent of phenol for each equivalent of salicylic acid. Congo red (Aldrich certified grade) is obtained commercially.

EXAMPLE 2

Chrysamine G and Chrysamine G Derivatives Bind Specifically to Aβ

Binding to Synthetic Aβ(10–43)

Chrysamine G binds well to synthetic Aβ(10–43) peptide in vitro. FIG. 4A shows a Scatchard analysis of the binding of Chrysamine G to Aβ(10–43). The higher affinity component has a $K_D$ of 0.257 μM and a $B_{max}$ of 3.18 nmoles Chrysamine G/mg Aβ(10–43). The lower affinity component is less well defined by these data, but appears to have a $K_D$ of 4.01 μM and a $B_{max}$ of 18.7 nmoles Chrysamine G/mg Aβ(10–43). The low affinity component represents the binding of Chrysamine G at high concentrations to a distinct, low-affinity site, not the binding to an impurity in the preparation. The amount of Chrysamine G injected in vivo is so low that there is not any binding to the low-affinity component. At very low concentrations, the ratio of high-to-low affinity binding is very large.

The amount of Chrysamine G binding is linear with peptide concentration over the range employed, as shown in FIG. 5.

Kinetics of Binding

Kinetic studies showed a fairly rapid association (FIG. 6A), essentially complete by 1 min, at a [Chrysamine G]=112 μM with a $t_{1/2}$ of 8.9±1.8 sec and a somewhat less rapid dissociation (FIG. 6C), $t_{1/2}$=55±9.4 sec [dissociation rate constant $(k_{-1})$=1.26×10$^{-2}$ sec$^{-1}$]. FIG. 6B shows a transformation of the association kinetic data according to the method of Bennett and Yamamura. Bennett, J. P. and Yamamura, H. I. in NEUROTRANSMITTER RECEPTOR BINDING (N.Y.: Raven Press 1985) pp. 61–89. The linear portion of the association curve in FIG. 6A is transformed into the line of FIG. 6B, in which $\ln[B_{eq}/(B_{eq}-B_t)]$ is plotted versus time, where $B_{eq}$ is the amount of Chrysamine G bound at equilibrium (4 min) and $B_t$ is the amount bound at time=t. The slope of this line equals $k_{observed}$ and $k_1$= $(k_{observed}-k_{-1})$/[Chrysamine G], where $k_{-1}$ is the dissociation rate constant determined from the data in FIG. 6C. The curve in FIG. 6C follows the equation:

$$A_t = A_0 e^{-k_{-1}t}$$

where $A_t$ is the amount of Chrysamine G remaining bound at time=t, $A_0$ is the amount of Chrysamine G bound at time=0, t is the time in min, and $k_{-1}$ is the dissociation rate constant. From this analysis, the association rate constant $(k_1)$ is calculated to be 3.75×10$^4$ M$^{-1}$ sec$^{-1}$ giving a $K_D=k_{-1}/k_1$=0.34 μM, in good agreement with the Scatchard analysis.

Chrysamine G Derivatives Can Inhibit the Binding of Chrysamine G to Aβ

$K_i$ values for the inhibition of [$^{14}$C]Chrysamine G binding to Aβ(10–43) by the Chrysamine G analogues are shown under the chemical structures in FIG. 1 and several displacement curves are shown in FIG. 3. $K_i$ is defined as IC$_{50}$/(1+ [L]/$K_D$), where [L] is the concentration of [$^{14}$C]Chrysamine G in the assay (0.100–0.125 μM) and $K_D$ is 0.26 μM, the $K_D$ of Chrysamine G determined by the Scatchard analysis above. Chrysamine G itself gives a $K_i$ of 0.37±0.04 μM, a value very consistent with those obtained from the Scatchard and kinetic analyses. Congo red gives a $K_i$ of 2.82±0.84 μM. The difluoro derivative of Chrysamine G, (5-FSA)CG, (FIG. 1) is one-third as potent as Chrysamine G itself ($K_i$= 1.16±0.19 μM). The activity of the difluoro Chrysamine G derivative suggests that an $^{18}$F difluoro Chrysamine G derivative works for PET imaging and an $^{19}$F difluoro Chrysamine G derivative works for MRS/MRI imaging of brain.

The 3-ICG is slightly more potent than Chrysamine G. The activity of the 3-ICG derivative suggests that an $^{123}$I difluoro Chrysamine G derivative works for SPECT imaging. Methylating the phenol of 3-ICG decreases the affinity by a factor of 10 in 3-IGC(OMe)$_2$. Methylating the carboxylate group effected an even greater (about 200-fold) decrease in affinity in CG(COOMe)$_2$. Removing the acid moiety entirely, as in the phenol derivative, completely destroyed binding affinity.

These results suggest that the acid moiety of Chrysamine G analogues plays the major role in binding to Aβ and that the phenol moiety plays an facilitating role. The effect of the phenol could occur through hydrogen bonding to the acid which could serve to stabilize the structural orientation of the acid moiety. The presence of a phenol in the ortho position could also alter the charge distribution of the acid either through hydrogen bonding or through changes in the charge distribution of the aromatic system as a whole. Alternatively, the phenol could directly participate in binding to the amyloid via a bi-dentate attachment of both the phenol and the acid to the amyloid binding site. Adding a second phenol ortho to the carboxylate as in the resorcylic acid derivative, (6-OHSA)CG, produces the highest affinity compound in this series having a $K_i$ of 0.094±0.02 μM.

Increasing the lipophilicity of the biphenyl backbone appears to increase the affinity somewhat. The di-halo derivatives, 3,3'-I$_2$CG, 3,3'-Br$_2$CG, and 3,3'-Cl$_2$CG, all have very similar K$_i$ values which are about half that of Chrysamine G.

Distorting the dihedral angle between the phenyl rings of the biphenyl group by substitution at the 2-position markedly diminishes affinity. This is demonstrated by the inactivity of the 2,2'-di-sulfonic acid derivative of Chrysamine G, 2,2'-(SO$_3$)$_2$CG. Since the 3,3' di-carboxylic derivative, 3,3'-(COOH)$_2$CG, shows only a 7-fold loss of activity from Chrysamine G, it is unlikely that the additional acidic moieties are the sole cause for the loss of activity in the 2,2'-disulfonic acid. This 2,2'-derivative is unique in that the bulky sulfonate groups in the 2-position force the biphenyl group out of planarity. Molecular modelling studies showed that the dihedral angle between the two biphenyl benzene rings in the 2,2'-disulfonic acid derivative is 83°. This angle is approximately 35–40° in Chrysamine G and all of the other active derivatives.

In an attempt to explore the importance of the bidentate nature of the functional groups of Chrysamine G, the binding of an aniline derivative which represents one-half of a Chrysamine G molecule (FIG. 1) was studied. An approximation of the energy of binding can be calculated from the equation:

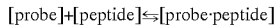

$$\Delta G = -RT \ln K_{eq}$$

where ΔG is the energy of the binding reaction, R is the molar gas constant [8.31441 J/(mole·° K)], T is temperature in ° K and K$_{eq}$ is the equilibrium constant for the reaction:

[probe]+[peptide]⇌[probe-peptide]

and K$_{eq}$=1/K$_D$≈1/K$_i$. Using the value of 0.26μM for the K$_D$ of Chrysamine G, the energy of binding is roughly 38 KJ/mole. If the aniline derivative binds with one-half of this energy, the expected energy of binding would be about 19 KJ/mole. From the K$_i$ of 73 μM for the aniline derivative, the energy of binding is 23 KJ/mole which is in acceptable agreement with the predicted value. The importance of the hydrophobic region of Chrysamine G and the aniline derivative is demonstrated by the total lack of binding activity of salicylic acid itself.

The affinity of Chrysamine G for Aβ appears to be several fold greater than the affinity of Congo red for this peptide. The binding is reversible with a dissociation constant of approximately 250–400 nM, whether measured by Scatchard analysis, kinetic methods, or inhibition of binding. Owing to the non-crystalline, poorly soluble nature of amyloid fibrils, the structure of Congo red or Chrysamine G complexes with amyloid has never been defined by precise structural techniques such as x-ray crystallography or multi-dimensional NMR. Models of Congo red interactions with amyloid have been proposed. Cooper, Lab. Invest. 31: 232 (1974); Romhanyi, Virchows Arch. 354: 209 (1971). This work suggests that Congo red does not bind to a single amyloid peptide molecule, but binds across several Aβ molecules oriented by virtue of the beta-sheet fibril. Klunk et al., J. Histochem. Cytochem. 37: 1273 (1989).

FIG. 7 shows a schematic of this model, generated using MacroModel 2.5, in which Chrysamine G spans 5 peptide chains in an anti-parallel beta-sheet conformation. The peptides are used without further structural refinement. The peptides are aligned so that alternate chains were spaced 4.76 Å apart, characteristic of beta-sheet fibrils. Alternate peptide chains are drawn in black and white. Chrysamine G (black) is energy minimized and aligned with the fibril model to maximize contact with lysine-16 (light grey ovals in top figure) and the hydrophobic phenylalanine 19/20 region (bottom). The two views are of the same model at approximately 90° from one another. The white arrows indicate the direction taken to obtain the alternate view.

The 19.1 Å spacing between the carboxylic acid moieties of Chrysamine G matches well with the distance of 19.0 Å across the 5 chains (4×4.76 Å between adjacent chains shown by Kirschner et al., Proc. Natl. Acad. Sci. U.S.A. 83: 503 (1986)). If the native structure of Aβ involves a hairpin loop structure as Hilbich et al., suggest (Hilbich et al., J. Mol. Biol. 218: 149 (1991)), then chains 1 and 2, 3 and 4, 5 and 6, etc., would be folded halves of the same molecule, but the model would otherwise be the same. Also important to note is the necessity for positively charged amino acid residues in this model, such as lysine-16 in Aβ. Previous work has shown that Congo red binding correlates well with the number of positively charged amino acids in a sample of amyloid fibrils. Klunk et al., J. Histochem. Cytochem. 37: 1273 (1989). The bidentate nature of the model in FIG. 7 and the importance of hydrophobic interactions is supported by the decrease in affinity of the mono-dentate aniline analogue of Chrysamine G and the inactivity of salicylic acid as well as the increased potency of the more lipophilic compounds having two halogens on the benzidine moiety (see FIG. 1). The importance of the nearly planar biphenyl group is suggested by the inactivity of the 2,2'-disulfonic acid derivative.

EXAMPLE 3

Chrysamine G Distinguishes Alzheimer's Disease Brain from Normal Brain

Characterization of the Binding of Chrysamine G to AD Brain

Scatchard analyses of the binding of Chrysamine G and Chrysamine G derivatives to AD brain samples were performed in an effort to understand the increased binding of Chrysamine G to AD brain. (FIG. 4B, Table 1). Under the conditions employed, control and AD brain showed a single binding component. The K$_D$ in AD brain was 16% lower than control but the difference was not significant (p=0.29). The B$_{max}$ in AD brain was 36% higher than the B$_{max}$ in control brain, but, again, the difference did not reach significance (p=0.09). Therefore, the increased binding in AD brain appears to be mainly due to the presence of more of the same binding component which exists in control brain, rather than the presence of a unique component.

TABLE 1

Comparison of binding Parameters in AD and control brain

| | K$_D$ (μM) | B$_{max}$ (pmol/μg prot) |
|---|---|---|
| Control (n = 6) | 0.47 ± .049 | 0.576 ± .092 |
| AD(n = 5) | 0.39 ± .048 | 0.784 ± .061 |

The binding of CG to AD brain significantly correlated with numbers of NPs in the association cortices of the brain. FIG. 8A shows the correlation of [$^{14}$C]CG binding with numbers of NPs in the superior/middle frontal and superior temporal cortex of AD brain. The correlation with NPs was significant whether controls were included (r=0.69; p=0.001) or if the AD brains were considered alone (r=0.59;

p=0.007). FIG. 8B shows a similar correlation with NFT counts. As with NPs, the correlation with NFTs was significant whether controls were included (r=0.60; p=0.001) or if the AD brains were considered alone (r=0.50; p=0.026). The correlation with NFTs is not surprising since CG is a derivative of Congo red, which stains NFTs. The number of NPs was significantly correlated with the number of NFTs (r=0.82; p=0.0001).

Only qualitative data on the presence or absence of amyloid angiopathy was available for the brains used in this study, so similar correlations could not be performed between CG binding and cerebrovascular amyloid levels. The presence of amyloid angiopathy does appear to be a confounding variable in the correlation of CG binding with NP counts. FIG. 8A shows the improved correlation of CG binding to NP counts in brains without amyloid angiopathy (r=0.79; p=0.01) compared to those brains with cerebrovascular amyloid deposits (r=0.49; p=0.15). A similar improvement was not found in the correlation to NFT counts.

The $K_D$ for [$^{14}$C]Chrysamine G binding to AD brain is similar to that found for [$^{14}$C]Chrysamine G binding to synthetic Aβ in vitro, suggesting that binding in brain homogenates also may represent interaction with Aβ. The correlation of Chrysamine G binding to NFTs may indicate that Chrysamine G binds to these structures in brain homogenates as well. Alternatively, since the number of NFTs correlates closely with the number of NPs, the correlation of [$^{14}$C]Chrysamine G binding to NFTs may just be an epiphenomenon of Chrysamine G binding to NPs.

The useful Chrysamine G derivatives or analogues provided herein have binding affinities that are at least in the range of 0.01 to 10.0 $\mu$M $K_D$, as measured by binding to either synthetic Aβ peptide or Alzheimer's Disease brain tissue; higher affinity compounds having binding affinities in the range of 0.0001 to 0.01 $\mu$M are also useful in the method of the present invention.

Considering the above, Chrysamine G binding may not be specific for Aβ. Instead, Chrysamine G binding may reflect the total amyloid "load" of the brain, comprised of aggregated deposits of Aβ in neuritic plaques and cerebrovascular amyloid. Deposits of phosphorylated tau protein in NFTs may contribute to Chrysamine G binding as well. Goedert, M. et al., *PNAS* 85: 4051 (1988). NFTs also are composed of anti-parallel beta-sheet fibrils similar in quaternary structure to fibrils of Aβ. Kirschner et al., *Proc. Natl. Acad. Sci. U.S.A.* 83: 503 (1986).

Total and Relative Chrysamine G Binding Distinguishes AD from Normal Brain

In vitro binding assays such as those described above and below are widely used in the art as models to screen compounds for in vivo binding in brain and to predict success in subsequent in vivo imaging studies. See, Young, A. et al., *Receptor Assays: In Vitro and In Vivo.* in POSITRON EMISSION TOMOGRAPHY AND AUTORADIOGRAPHY (Phelps, M., Mazziota, J., and Schelbert, H. eds.) pp. 73–111 (1986). The labeled Chrysamine G and Chrysamine G derivatives of the invention also may be used in the in vitro binding assays described above and below to quantitate amyloid deposits in biopsy or post-mortem specimens.

Saturable (specific) binding of [$^{14}$C]Chrysamine G was observed both in AD brain and control brain homogenates and constituted 60–80% of total binding in AD brain. Non-saturable binding was very similar in AD and control brain. Both saturable and total binding were greater in AD brain than in control. Despite the lower sensitivity obtained when using total binding, this parameter is more predictive of success in in vivo studies which are the ultimate goal of this invention. Also for the purpose of extension to in vivo studies, it is advantageous if Chrysamine G binding in cortical areas is normalized to a brain area in which Chrysamine G binding is very similar in both AD and control brain. This obviates the need to calculate the absolute quantity bound which is difficult to do in vivo. We examined binding in the cerebellum as a potential control area because classical NPs are exceedingly rare in this brain area (Joachim et al., *Am. J. Pathol.* 135: 309 (1989)).

The average amount of [$^{14}$C]Chrysamine G bound to control cerebellum is nearly identical to the amount bound to AD cerebellum (Table 2), supporting the use of cerebellum as an internal control. Therefore, the cerebellar ratio (CBR) accurately reflects the absolute quantity of [$^{14}$C] Chrysamine G bound and offers the advantage of providing an internal control for each brain. Binding is greater in AD brain whether expressed in absolute terms of fmol/$\mu$g protein (Table 2) or as a ratio to the binding in the cerebellum of the same brain (Table 3). The CBR is the more sensitive measure and shows less variability between brains. The use of total binding and CBRs greatly facilitates extension of these ex vivo results to in vivo studies. Accordingly, the results below are expressed in these terms whenever appropriate.

TABLE 2

Comparison of total binding in AD and control brain*.

| Brain Area | Control (fmol/$\mu$g protein) | AD (fmol/$\mu$g protein) | p Value |
|---|---|---|---|
| Cerebellum | 75 ± 13 (n = 8) | 73 ± 9 (n = 11) | p = 0.91 |
| Frontal Pole | 58 ± 8 (n = 6) | 124 ± 16 (n = 10) | p < 0.006 |
| Superior/Middle Frontal | 54 ± 10 (n = 8) | 130 ± 21 (n = 11) | p < 0.005 |
| Superior Temporal | 66 ± 17 (n = 8) | 121 ± 14 (n = 11) | p < 0.02 |
| Head of Caudate | 73 ± 11 (n = 4) | 123 ± 22 (n = 7) | p = 0.14 |
| Inferior Parietal | 76 ± 13 (n = 8) | 137 ± 19 (n = 11) | p < 0.03 |
| Occipital | 64 ± 16 (n = 8) | 95 ± 12 (n = 11) | p = 0.15 |

*High- and low-plaque AD brains combined.

TABLE 3

Comparison of total binding in AD and control brain as a ratio to cerebellum*.

| Brain Area | Control (CBR) | AD (CBR) | p Value |
|---|---|---|---|
| Frontal Pole | 0.87 ± .04 (n = 6) | 1.87 ± .25 (n = 10) | p < 0.004 |
| Superior/Middle Frontal | 0.73 ± .02 (n = 8) | 1.84 ± .18 (n = 11) | p < 0.001 |
| Superior Temporal | 0.86 ± .08 (n = 8) | 1.63 ± .17 (n = 11) | p < 0.002 |
| Head of Caudate | 0.95 ± .04 (n = 4) | 1.76 ± .31 (n = 7) | p < 0.04 |
| Inferior Parietal | 0.90 ± .08 (n = 8) | 1.93 ± .20 (n = 11) | p < 0.001 |
| Occipital | 0.77 ± .13 (n = 8) | 1.44 ± .20 (n = 11) | p < 0.02 |

*The CBR for each sample is obtained by dividing the absolute value of [$^{14}$C] Chrysamine G binding in that sample by the absolute value of [$^{14}$C] Chrysamine G binding in the cerebellar sample from that same brain. The values in the table are the average CBRs from each brain area (± SEM). High- and low-plaque AD brains combined.

FIGS. 9A and 9B shows the binding of [$^{14}$C]Chrysamine G to six brain areas normalized to the cerebellum of the same brain. The binding of Chrysamine G to AD brain areas in AD brains having more than 20 NPs/×200 magnification, "High Plaque AD Brains", is shown in FIG. 9A. The binding of Chrysamine G to AD brain areas in AD brains having less than 20 NPs/×200 magnification, "Low Plaque AD Brains", is shown in FIG. 9B. In all brain areas, the binding to AD brain is significantly greater than the binding to control (see Table 3). In superior/middle frontal cortex, there is no overlap between control and any of the AD samples. In all brain areas except the occipital cortex, there is no overlap between control and the AD samples having >20 NPs/×200 magnification. In brain areas with the least deposition of classical NPs, such as the occipital cortex (and cerebellum), the greatest overlap between AD and control was observed.

FIG. 9C shows the data from two patients who had Down's syndrome. Down's syndrome patients all develop deposits of Aβ by their fourth decade and many develop AD. Wisniewski et al., *Neurology* 35: 957 (1985); Schapiro et al., *Neurobiol. Aging* 13, 723 (1992). Both of these patients showed [$^{14}$C]Chrysamine G binding above the control range. Since the younger patient (23 years old) had amyloid deposits but was not yet clinically demented, FIG. 9C suggests that Chrysamine G can detect differences from control in non-demented patients destined to develop AD long before the dementia is clinically evident.

The compounds and method of the invention provide two useful measurements for differentiating AD brain from normal brain; either (1) total Chrysamine G binding (Table 2) or (2) the ratio of Chrysamine G binding in a given brain area to binding in the cerebellum of the same brain (Table 3). These measurements furnish two great advantages for in vivo quantitation of AD neuritic plaques. First, by providing a means to measure total Aβ binding, rather than specific Aβ binding, the instant invention can quantify Aβ deposition without having to expose the subject to a second injection of radioactive material in order to measure non-specific binding. Because of this, the data are expressed as total binding only. In all of the experiments presented, specific binding data yields even greater differences between AD and control brain.

Figure 9:
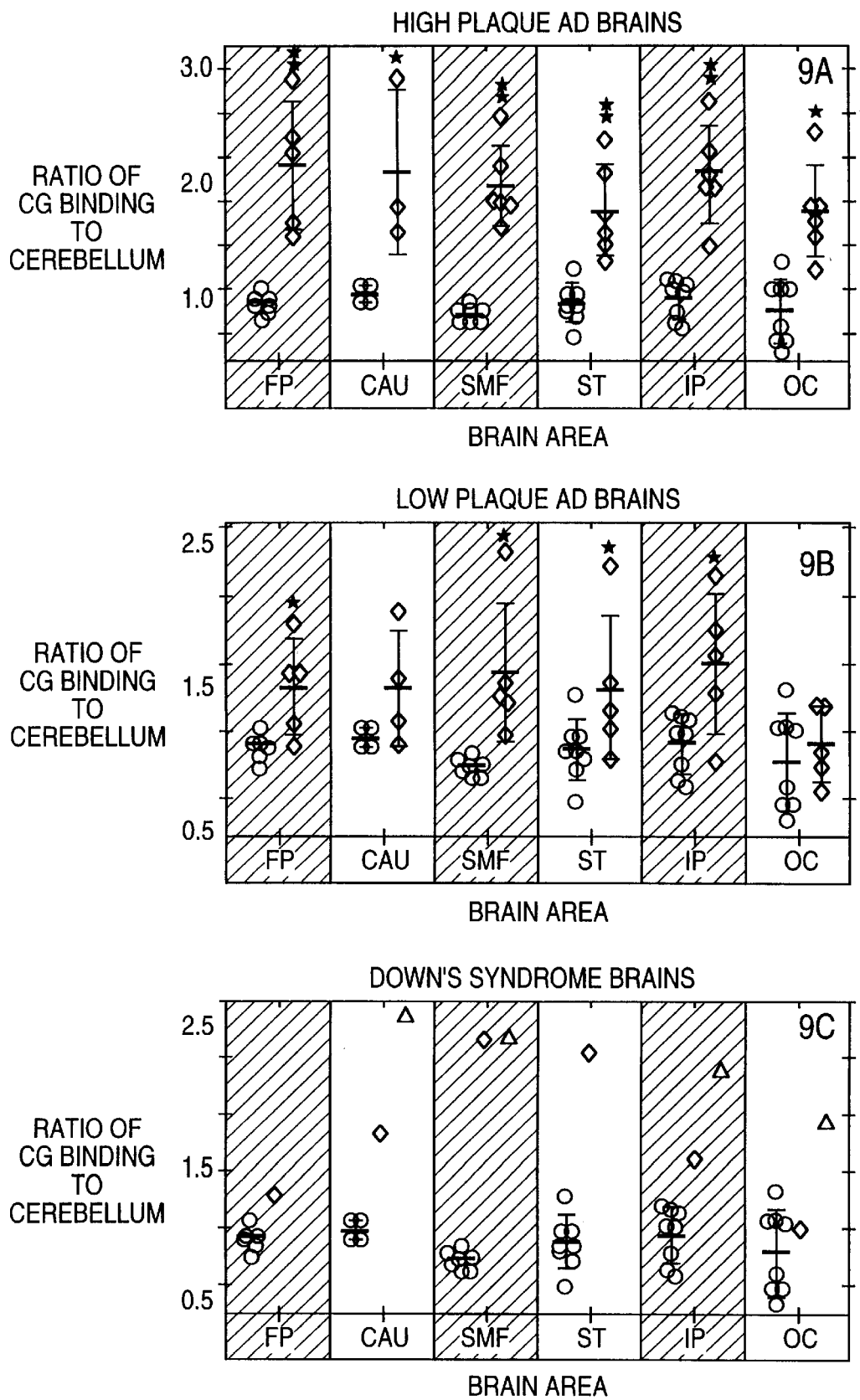

Second, variations in brain uptake of Chrysamine G derivatives will affect the absolute concentration of Chrysamine G in brain. Some mechanism will be necessary, therefore, to account for these variations between subjects. Each patient can serve as his/her own control by finding a brain area that shows little Aβ deposition (i.e., an experimental "blank"). Since classical NPs are exceedingly rare in the cerebellum (Joachim et al., *Am. J. Pathol.* 135: 309 (1989)), Chrysamine G binding to the cerebellum was used as a control for each brain studied. The results were expressed in terms of the ratio of Chrysamine G binding in a given brain area to binding in the cerebellum of the same brain (FIG. 9 and Table 3).

For the purposes of in vivo quantitation of amyloid in AD, the effect of brain atrophy should be considered. Therefore, when using the Chrysamine G and Chrysamine G derivative probes in vivo to quantitate amyloid, brain atrophy can be corrected based on MRI volume measurements. MRI volume measurements performed in conjunction with the method of the invention are analogous to those routinely employed in the art. See, Pearlson, G. and Marsh, L. MAGNETIC RESONANCE IMAGING IN PSYCHIATRY in *Annual Review of Psychiatry* (Vol. 12) Oldham, J. et al., eds. p. 347–381 (1993). Therefore a method for determining the total radioactivity per volume of brain area would use the following equation:

$$\frac{\text{total SPECT or PET signal from brain area ``A''}}{\text{MRI determined brain volume (excluding CSF) in brain area ``A''}}$$

Designating this measurement as the signal/volume for brain area "A" or $S/V_A$ means that the cerebellar ratio would be expressed as:

$$\text{Ratio}_A = \frac{S/V_A}{S/V_{CB}}$$

where $S/V_{CB}$ is the signal/volume in the cerebellum of the same subject during the same imaging study. This ratio from any brain area other than cerebellum from a patient suspected of having AD or other pathological condition characterized by the deposition of amyloid could then be compared to the normal range of the analogous ratio from the same brain area of a group of age-matched normal control subjects. The ratio of the binding to brain areas with high deposits of neuritic plaques to the cerebellum can be used as the parameter to distinguish Alzheimer from control subjects.

EXAMPLE 4

The Octanol-Water Partition Coefficients of Chrysamine G, Chrysamine G Derivatives, and Congo Red The octanol-water partition coefficient is a measure of the relative lipophilicity of a compound. The more lipophilic a compound, the more likely it is to cross the blood-brain barrier. See, Goodman and Gilman's THE PHARMACOLOGICAL BASIS FOR THERAPEUTICS (7th Ed.). The octanol/water partition coefficient of Chrysamine G is 60.22±3.97 and that of Congo red is 0.665±0.037 (p<0.001). This suggests that Chrysamine G is approximately 90 times more lipophilic than Congo red and therefore is theoretically more likely to cross the mammalian blood-brain barrier. The octanol/water partition coefficients for the 3-iodo and 3,3'-diiodo derivatives of Chrysamine G (FIG. 1) are 72.53±7.4 and 112.9±7.3, respectively. These octanol/water partition coefficients show that these derivatives, which are non-radioactive analogues of some of the radiolabeled Chrysamine G derivatives to be used for in vivo studies, are up to 170 times more lipophilic than Congo red and up to twice as lipophilic as Chrysamine G. This suggests they will enter the brain much better than either Congo red or Chrysamine G.

EXAMPLE 5

The Ability of Chrysamine G and Chrysamine G Derivatives to Cross the Blood-Brain Barrier and Metabolism of Chrysamine G Use of the amyloid probes to diagnose AD in vivo requires them to be able to cross the blood-brain barrier and gain access to parenchymal amyloid deposits.

The ability of Chrysamine G to cross the blood-brain barrier was studied in Swiss-Webster mice. After i.v. injection, the brain/blood ratio measured at 15 min was over 10:1 and approached 20:1 by 35 min (FIG. 10). The radioactivity in brain stayed nearly constant over this period, but decreased in the blood and increased in the liver. The brain/kidney ratio was highest at 15 min (over the time points sampled) and approached 0.5. When brain and liver were extracted 60 min after i.v. injection of [$^{14}$C] Chrysamine G, >95% of the recovered radioactivity co-eluted with authentic Chrysamine G on reverse phase HPLC, indicating no significant metabolism of Chrysamine G over this period of time.

Chrysamine G does get into normal mouse brain, and the brain/blood ratio is high. The radioactivity in brain remained relatively constant over the first 30 min while decreasing in blood and increasing in liver. This suggests that the high brain/blood ratio is more a result of efficient removal of Chrysamine G from the blood by the liver than to further accumulation in the brain. At 60 min, essentially all of the radioactivity found in the brain and liver proved to be unchanged Chrysamine G. Congo red does not cross the blood-brain barrier well. Tubis et al., *J. Amer. Pharm. Assn.* 49: 422 (1960). Most of the Congo red is cleared by the liver and spleen and the brain/kidney ratio achieved in guinea pigs is approximately 0.07. Tubis et al., supra. Chrysamine G also is cleared by the liver, but has greater entry into the brain.

In vivo animal testing provides yet a further basis for determining dosage ranges, efficacy of transfer through the blood barrier and binding ability. Particularly preferred for this purpose are the transgenic mouse model of Games et al., (*Nature* 373: 523 (1995)) or Hsiao et al. *Science* 274: 99–102 (1996) and the "senile animal" model for cerebral amyloidosis; i.e., animals such as the transgenic mice or aged dogs or monkeys, which are known to develop variable numbers of Alzheimer-type cerebral neuritic plaques, see Wisniewski et al., *J. Neuropathol. & Exp. Neurol.* 32: 566 (1973), Selkoe et al., *Science* 235: 873 (1987), are tested for binding and detection efficacy. This in vivo assay requires control-biopsy or necropsy monitoring to confirm and quantify the presence of amyloid deposits.

Other suitable animal models for use in testing the compositions and methods of the present invention are produced transgenically. For instance, Quon et al., *Nature*, 352: 239–241 (1991) used rat neural-specific enolase promoter inhibitor domain to prepare transgenic mice. See also, Wirak et al., *Science*, 253: 323–325 (1991). Still other models have been produced by Intracranial administration of the β/A4 peptide directly to animals (Tate et al., *Bull. Clin. Neurosci.*, 56: 131–139 (1991).

It is noted that none of the in vivo animal models may turn out to be extremely good models for AD neuropathology. Instead, they may more closely model the amyloid deposition of normal aging. This is particularly true of the aged-mammal models. All of these models show a preponderance of diffuse plaques as discussed above for the aged dog model. While there is some cerebrovascular amyloid, there are few neuritic plaques, except in the Games et al. and Hsiao et al. transgenic mouse models. The other transgenic mouse models often show only diffuse plaques. Therefore, while these models may be useful for studying distribution of the probes in the brain, there is a fairly low probability that these models would show the same quantitative differences that would be expected to be seen in AD brain based on the in vitro studies of Chrysamine G binding to AD brain described above.

Evaluating the Ability of Alkyl, Alkenyl or Alkynyl Chrysamine G Derivatives to Cross the Human Blood-Brain Barrier A dose of approximately 10 mCi of an appropriately radiolabeled derivative of Chrysamine G with a specific activity of approximately 500 Ci/mole or higher is injected intravenously into normal subjects and patients suspected of having AD and monitored by SPECT or PET imaging to analyze the detectability of the derivative in brain relative to other organs and to define the time course of detectability in the brain. A dose which can be reliably detected is defined as a "imaging effective dose."

Evaluation of Alkyl, Alkenyl or Alkynyl Chrysamine G Derivatives to Distinguish AD from Age-Matched Controls in Humans An imaging-effective dose of an appropriately, radioactively labeled derivative of Chrysamine G is injected into a subject suspected of having brain amyloid deposition due to pathological conditions such as AD. After a period of 15 minutes to 24 hours, the radioactive signal from brain is detected by SPECT or PET. Radioactivity is simultaneously detected in all brain areas included in the field of view of the detector. This field of view will be set up so as to include large portions of the cerebellum, superior temporal cortex, superior/middle frontal cortex, and intervening brain regions. An MRI scan will be performed prior to the study so that corrections can be made for brain atrophy in the areas of interest by methods discussed in Example 3. The $S/V_A$, $S/V_{CB}$, and $Ratio_A$ variables discussed in Example 3 will be calculated and compared to analogous normative ratios obtained previously from age-matched normal control subjects.

EXAMPLE 6

Histologic Localization of the Binding of an Alkenyl Chrysamine G Derivative to Amyloid The top frame of FIG. 11 demonstrates a human AD brain stained by 1,4-bis(3-carboxy-4-hydroxyphenylethenyl)-benzene. The staining method was that of Stokes and Trickey, *J. Clin. Pathol.* 26: 241–242 (1973) with 1,4-bis (3-carboxy-4-hydroxyphenylethenyl)-benzene substituted for Congo red. This staining is much more intense than that observed with Chrysamine G, Congo red, or Thioflavin S. Numerous amyloid plaques and neuropil threads can be readily identified as well as a neurofibrillary tangle. The bottom photomicrograph in FIG. 11 shows a section of trangenic mouse brain [Tg(HuAPP695.SWE)2576; Hsiao et al. *Science* 274: 99–102 (1996)] stained with 1,4-bis(3-carboxy-4-hydroxyphenylethenyl)-benzene. The dense amyloid plaques is intensely stained. Cerebrovascular amyloid also is intensely stained in both human and mouse brain (data not shown).

EXAMPLE 7

Assessing the Toxicity of Alkyl, Alkenyl or Alkynyl Chrysamine G Derivatives

At doses of 10 and 100 mg/kg non-radioactive Chrysamine G administered intraperitoneally, no notable behavioral effects or toxicity were observed in mice for periods up to 72 hrs. The doses of [$^{14}$C] Chrysamine G administered were on the order of 1 mg/kg.

Chrysamine G appeared to show little acute toxicity based on attempts to establish an $LD_{50}$. Even when the maximum volume that can be injected into a mouse without harming it just from fluid volume effects (approx. 0.025 ml/g) of a saturated solution of Chrysamine C was injected into mice (100 mg/kg), there were no behavioral changes noted for at least 72 hrs, the longest period tested. Doses required for detection of radiolabeled derivatives by SPECT or PET would be orders of magnitude below this dose.

Congo red has been safely injected into humans in quantities much greater than would be used for the radioactive Chrysamine G derivatives. The $LD_{50}$ for Congo red has been shown to be 190 mg/kg mouse (Tubis et al., *J. Amer. Pharm. Assoc.* 49: 422 (1960)), which is similar to the >100 mg/kg $LD_{50}$ shown for Chrysamine G. Thus, these two chemically similar compounds cause similar low toxicities in mice.

Other alkyl, alkenyl or alkynyl Chrysamine G derivatives can similarly be tested for toxicity in mice and other higher mammals by injecting a wide range of concentrations and studying the animals for various signs of toxicity by methods well known in the art. See, Goodman and Gilman's THE PHARMACOLOGICAL BASIS FOR THERAPEUTICS (7th Ed.).

EXAMPLE 8

Assessing the Ability of Chrysamine G to Protect Against Aβ (25–35)-Induced Toxicity Protection from Aβ (25–35)-induced Toxicity in PC-12 cells Rat pheochromocytoma cells (PC-12) were grown in RPMI 1640 media with 10% fetal bovine serum. Approximately 5,000 exponentially growing cells were plated in 96-well plates in a volume of 100 μl of media and allowed to incubate at 37° C. overnight. The Aβ (25–35), which had been pre-aggregated at 37° C. for 7 days, was pre-incubated with Chrysamine G (CG) or related compounds in aqueous solution prior to addition of 20 μl to achieve the final concentrations given (0.01 to 10 μM Aβ (25–35) and 0.03 to 20 μM CG). The cells were incubated for 24 hrs prior to the addition of 13.3 μl of 5 mg/ml MTT (3,(4,5-dimethylthiazol-2-yl)2,5-diphenyltetrazolium bromide) in sterile phosphate buffered saline. After 4.5 hrs at 37° C., 100 μl of extraction buffer (20% w/v SDS in 50% DMF/water; pH adjusted to 4.7 with 2.5% of 80% acetic acid and 2.5% 1N HCl) was added and the plates were incubated overnight. Hansen et al., *J. Immunol.* Methods 119: 203 (1989). Color development was then measured at 560 nm. Maximum viability was defined as the absorbance of control wells to which only the 20 μl of distilled, deionized H2O was added. Maximum toxicity was defined by wells in which the cells were lysed by addition of 0.1% (final concentration) of Triton X-100.

Incubation of PC12 cells with Aβ (25–35) results in a concentration-dependent decrease in the ability of these cells to reduce MTT (FIG. 12). FIG. 12 shows the effect of increasing concentrations of Aβ (25–35) in the presence and absence of Chrysamine G on the cellular redox activity of PC12 cells as measured by MTT reduction. The reduction product of MTT absorbs at 560 nm which is plotted on the vertical axis. The effect of Aβ (25–35) alone is shown in the filled bars and shows a dose dependent decrease in MTT reduction. Significant differences from control (no Aβ, no Chrysamine G) are shown in white numbers inside the filled bars. The protective effect of 20 μM Chrysamine G is shown in the open bars. Significant differences between MTT reduction in the presence and absence of Chrysamine G are shown in black numbers inside the open bars.

FIG. 13 demonstrates the protective effect of increasing concentrations of Chrysamine G against the Aβ (25–35)-induced reduction of cellular redox activity of PC12 cells. The effect of Chrysamine G in the absence of Aβ (25–35) is shown in the filled bars. There was no significant difference between control (no Aβ, no Chrysamine G) and any of the concentrations of Chrysamine G in the absence of Aβ (25–35). MTT reduction in the presence of 1 μM Aβ (25–35) and increasing concentrations of Chrysamine G is shown in the open bars. Significant differences in MTT reduction between the presence and absence of Aβ (25–35) at each concentration of Chrysamine G are shown in white numbers inside the filled bars. Significant differences in MTT reduction between the Aβ (25–35) control (no Chrysamine G) and Aβ (25–35) plus increasing concentrations of Chrysamine G are shown in black numbers inside the open bars.

As has previously been reported, Congo red protects against the Aβ-induced toxicity at concentrations over 2 μM, achieving complete protection by 20 μM. Burgevin et al. *NeuroReport* 5: 2429 (1994); Lorenzo and Yankner, Proc. Natl. Acad. Sci. 91: 12243 (1994); Pollack et al., *Neuroscience Letters* 184: 113 (1995); Pollack et al. *Neuroscience Letters* 197: 211 (1995). Chrysamine G shows a protective effect which is dependent on both the concentration of Aβ (25–35) (FIG. 12) as well as the concentration of Chrysamine G (FIG. 13). The protective effect of Chrysamine G is evident at 0.2 μM, a concentration very close to the Ki of Chrysamine G for binding to synthetic Aβ, 0.37 μM (FIG. 1). Chrysamine G appears to be more potent than Congo red, showing effects in the range of 0.1 to 1.0 μM. This is consistent with the Ki values for binding to synthetic Aβ of 0.37 μM for Chrysamine G and 2.8 μM for Congo red (FIG. 1).

In another experiment (FIG. 14), the effect of Chrysamine G and the phenol derivative (see FIG. 1), which does not bind Aβ, was examined in cells incubated with 1 μM Aβ (25–35). Chrysamine G showed protective effects at 0.1 and 1 μM, but the phenol derivative showed no protective effects, and perhaps enhanced the toxicity of Aβ.

These results suggest that the lipophilic derivative of Congo red, Chrysamine G, prevents Aβ-induced cytotoxicity in cell culture at concentrations very similar to those at which it binds Aβ. This protection shows structural specificity since the phenol derivative which does not bind to synthetic Aβ also does not prevent Aβ-induced cytotoxicity. Since Chrysamine G partitions into the brain well, these results provide evidence that Chrysamine G and Aβ-binding derivatives of Chrysamine G have therapeutic potential in the treatment of AD.

The mechanism of the protective effect of Chrysamine G is unknown at present. Two broad possibilities exist. First, Chrysamine G could interfere with the aggregation of Aβ. Second, Chrysamine G could interfere with the effects (direct or indirect) of Aβ on the target cells. Congo red does inhibit aggregation of Aβ as well as protect against the toxic effects of aggregated Aβ. Lorenzo and Yankner, *Proc. Natl. Acad. Sci.* 91: 12243 (1994). Interference with aggregation is unlikely in the above experiment since the Aβ was pre-aggregated prior to incubation with Chrysamine G. Thus, inhibition of aggregation could prove to be an important therapeutic effect of Chrysamine G but is not a likely explanation for the protective effects of Chrysamine G against pre-aggregated Aβ. The model of Chrysamine G binding to Aβ described in FIG. 7, displays how Chrysamine G could "coat" the surface of Aβ. This may change how the fibrillar deposits are recognized by cell-surface receptors or other macromolecules such as complement proteins and interfere with the toxic effects of Aβ which may be mediated by these macromolecules. It is likely that Chrysamine G and Congo red exert multiple effects, both before and after the aggregation of Aβ. This is advantageous from a therapeutic point of view since patients are likely to present at a time when there are pre-existing Aβ aggregates as well as ongoing amyloid deposition.

What is claimed is:

1. A method of inhibiting cell degeneration and toxicity associated with fibril formation in an amyloidosis-associated condition, said method comprising the step of administering to a subject having or suspected of having such condition a pharmaceutically effective amount of Chrysamine G or a derivative thereof, wherein said derivative of Chrysamine G is an amyloid binding compound of Formula I or a water soluble, non-toxic salt thereof:

(I)

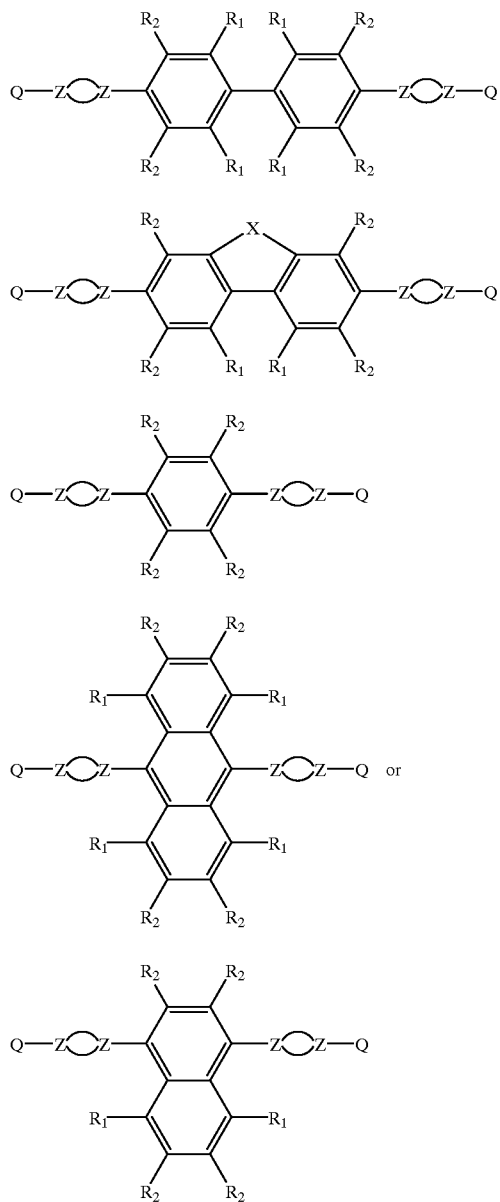

wherein:

is either C≡C, CR'=CR', or CR'$_2$—CR'$_2$ (where R' represents H or a lower alkyl group);

X is C(R")$_2$ (wherein R" is each independently is H, F, Cl, Br, I, a lower alkyl group, (CH$_2$)$_n$OR' where n=1, 2, or 3, CF$_3$, CH$_2$—CH$_2$F,O—CH$_2$—CH$_2$F, CH$_2$—CH$_2$—CH$_2$F, O—CH$_2$—CH$_2$—CH$_2$F, CN, (C=O)—R', N(R')$_2$, NO$_2$, (C=O)N(R')$_2$ O(CO)R', OR', SR', COOR', R$_{Ph}$, CR'=CR'—R$_{Ph}$, CR'$_2$—CR'$_2$—R$_{Ph}$ (where R$_{Ph}$ represents an unsubstituted or substituted phenyl group with the phenyl substitutents being chosen from any of the non-phenyl substitutents defined for R", a tri-alkyl tin, a tetrazole or oxadiazole of the form:

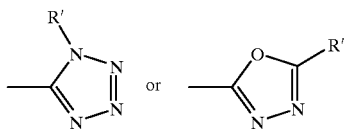

wherein R' is H or a lower alkyl group)

or X is CR'=CR', N=N, C=O, O, NR' (where R' represents H or a lower alkyl group), S, or SO$_2$;

each R$_1$ and R$_2$ independently is H, F, Cl, Br, I, a lower alkyl group, (CH$_2$)$_n$OR' where n=1, 2, or 3, CF$_3$, CH$_2$—CH$_2$F, O—CH$_2$—CH$_2$F, CH$_2$—CH$_2$—CH$_2$F, O—CH$_2$—CH$_2$—CH$_2$F, CN, (C=O)—R', N(R')$_2$, NO$_2$, (C=O)N(R')$_2$O (CO)R', OR', SR', COOR', a tri-alkyl tin, R$_{Ph}$, CR'=CR'—R$_{Ph}$, CR'$_2$—CR'$_2$—R$_{Ph}$ (where R$_{Ph}$ represents an unsubstituted or substituted phenyl group with the phenyl substituents being chosen from any of the non-phenyl substituents defined for R$_1$ and R$_2$, a tetrazole or oxadiazole of the form:

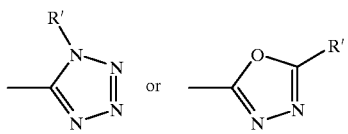

(wherein R' is H or a lower alkyl group), or a triazene of the form:

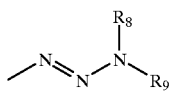

wherein R$_8$ and R$_9$ are lower alkyl groups) or

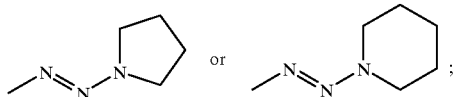

each Q is independently selected from one of the following structures:

IA, IB, IC, ID, IE, IF and IG, wherein

IA has the following structure:

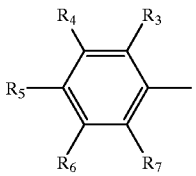
(IA)

wherein:

each of $R_3$, $R_4$, $R_5$, $R_6$, or $R_7$ independently is defined the same as $R_1$ above;

IB has the following structure:

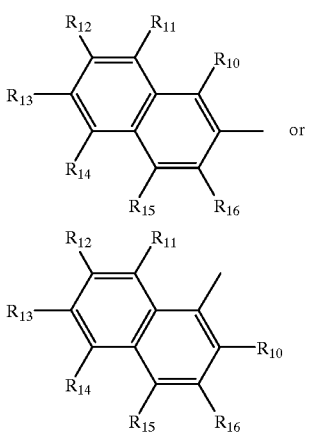
(IB)

or wherein:

each of $R_{10}$, $R_{11}$, $R_{12}$, $R_{13}$, $R_{14}$, $R_{15}$, or $R_{16}$ independently is defined the same as $R_1$, above;

IC has the following structure:

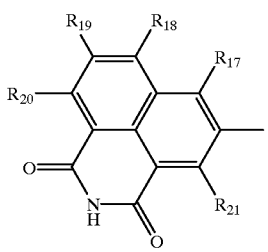
(IC)

wherein:

each of $R_{17}$, $R_{18}$, $R_{19}$, $R_{20}$, or $R_{21}$ independently is defined the same as $R_1$ above;

ID has the following structure:

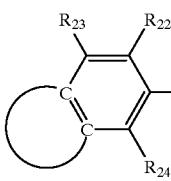 or 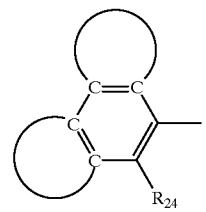
(ID)

wherein:

each of $R_{22}$, $R_{23}$, or $R_{24}$ independently is defined the same as $R_1$ above and

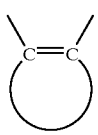

represents a heterocyclic ring of one of the six following formulas:

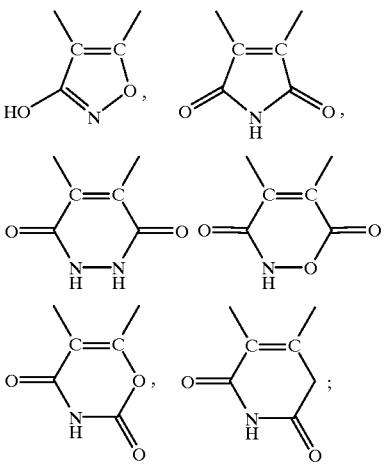

IE has the following structure:

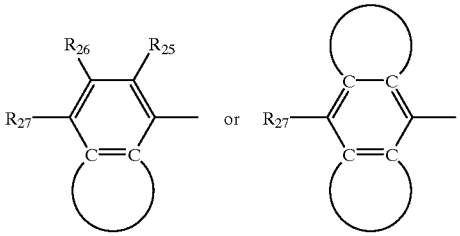
(IE)

wherein:

each of $R_{25}$, $R_{26}$, or $R_{27}$ independently is defined the same as $R_1$ above and 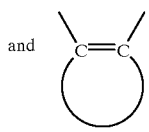

represents a heterocyclic ring of one of the six following formulas:

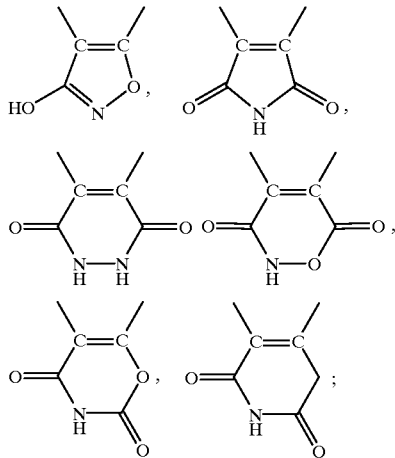

IF has the following structure:

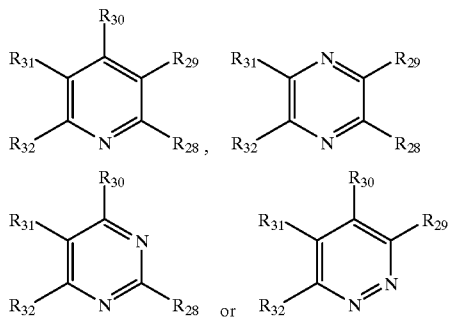

wherein:
exactly one of $R_{28}$, $R_{29}$, $R_{30}$, $R_{31}$, or $R_{32}$ is the

link defined for Formula I above and each other $R_{28}$, $R_{29}$, $R_{30}$, $R_{31}$ or $R_{32}$ independently is defined the same as $R_1$ above;

IG has the following structure:

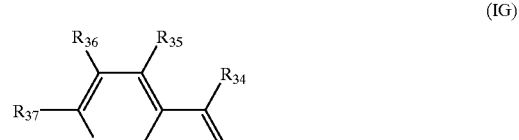

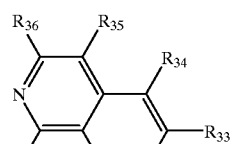

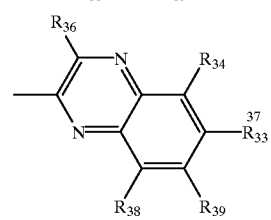

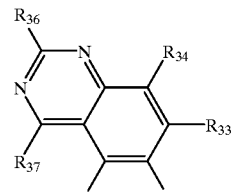

or

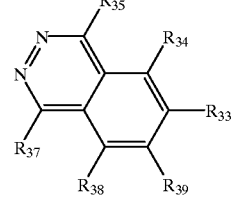

wherein:
exactly one of $R_{33}$, $R_{34}$, $R_{35}$, $R_{36}$, $R_{37}$, $R_{38}$, or $R_{39}$ is the Z Z link defined for Formula I above and each other $R_{33}$, $R_{34}$, $R_{35}$, $R_{36}$, $R_{37}$, $R_{38}$, or $R_{39}$ independently is defined the same as $R_1$ above.

2. The method of claim 1, wherein said amyloidosis-associated condition is selected from the group consisting of Alzheimer's Disease, Down's Syndrome, Type 2 diabetes mellitus, hereditary cerebral hemorrhage amyloidosis (Dutch), AIAPP or amylin insulinoma, and Asor or Pr P-27 (scrapie, Creutzfeld Jacob disease, Gertsmann-Straussler-Scheinker syndrome, bovine spongiform encephalitis).

* * * * *